United States Patent
Bergstein

(10) Patent No.: US 9,873,743 B2
(45) Date of Patent: Jan. 23, 2018

(54) IL3Rα ANTIBODY CONJUGATES AND USES THEREOF

(71) Applicant: Stemline Therapeutics, Inc., New York, NY (US)

(72) Inventor: Ivan Bergstein, New York, NY (US)

(73) Assignee: Stemline Therapeutics, Inc., New York, NY (US)

(*) Notice: Subject to any disclaimer, the term of this patent is extended or adjusted under 35 U.S.C. 154(b) by 0 days.

(21) Appl. No.: 15/342,668

(22) Filed: Nov. 3, 2016

(65) Prior Publication Data

US 2017/0152321 A1 Jun. 1, 2017

Related U.S. Application Data

(63) Continuation of application No. 14/632,178, filed on Feb. 26, 2015, now Pat. No. 9,518,119, which is a continuation of application No. 13/439,453, filed on Apr. 4, 2012, now Pat. No. 8,992,910, which is a continuation of application No. 12/082,940, filed on Apr. 14, 2008, now Pat. No. 8,163,279.

(60) Provisional application No. 60/923,499, filed on Apr. 13, 2007.

(51) Int. Cl.
| | |
|---|---|
| C12P 21/02 | (2006.01) |
| C07K 16/28 | (2006.01) |
| C12N 9/10 | (2006.01) |
| C12P 21/06 | (2006.01) |
| C12N 15/64 | (2006.01) |
| C12N 5/16 | (2006.01) |
| C07K 14/705 | (2006.01) |
| A61K 39/395 | (2006.01) |

(52) U.S. Cl.
CPC ........ *C07K 16/2866* (2013.01); *C12N 9/1077* (2013.01); *C12Y 204/02036* (2013.01); *C07K 2317/56* (2013.01); *C07K 2317/565* (2013.01); *C07K 2317/622* (2013.01); *C07K 2317/92* (2013.01); *C07K 2317/94* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 4,340,535 A | 7/1982 | Voisin et al. | |
| 5,489,516 A | 2/1996 | Broudy et al. | |
| 6,733,743 B2 | 5/2004 | Jordan | |
| 7,651,678 B2 | 1/2010 | Jordan | |
| 2003/0039611 A1 | 2/2003 | Jordan | |
| 2004/0197337 A1 | 10/2004 | Jordan | |
| 2010/0093003 A1 | 4/2010 | Jordan | |

FOREIGN PATENT DOCUMENTS

WO WO 97/24373 7/1997

OTHER PUBLICATIONS

Aldinucci et al., 2002, "Expression of Functional Interleukin-3 Receptors on Hodgkin and Reed-Sternberg Cells"Am J Pathol 160:585-596.
Aldinucci et al., 2005, "The role of interleukin-3 in classical Hodgkin's disease" Leukemia & Lymph. 46(3): 303-311.
Bendall, 2010, "New and emerging drug targets for the treatment of hematological malignancies". Curr Drug Targets. 11(7):767-768.
Brooks et al., 2012, "A novel antibody conjugate that targets interleukin-3 receptor alpha (CD123), possesses pre-clinical antitumor activity against Hodgkin's lymphoma," ASH Meeting, Poster 2768.
Chan et al., 1996, "Reactivity of murine cytokine fusion toxin, diphtheria toxin390-murine interleukin-3 (DT390-mIL-3), with bone marrow progenitor cells," Blood, 88:1445-1456.
Clayberger, 1992, "Interleukin 3 Is a Growth Factor for Human Follicular B Cell Lymphoma" J. Exp. Med. 9(175): 371-376.
Cochlovius et al., 2003, *Therapeutic Antibodies*: After years of promise, magic bullets appear to be on the upswing.Modern Drug Discovery 33-38.
Diefenbach et al., 2011, "Lymphoma-pre-clinical-chemotherapy and biologic agents," Poster III; Poster 3737.
Djokic et al., 2009 "Overexpression of CD123 correlates with the hyperdiploid genotype in acute lymphoblastic leukemia" Haematol. 94:1016-1019.
Du et al., 2007, "New Immunotoxins Targeting CD123, as a stem cell antigen, on acute myeloid leukemia cells." J. Immunotherap. 30(6): 607-613.
Feldman et al., 1998, "Anti-TNF alpha therapy is useful in rheumatoid arthritis and Crohn's disease: analysis of the mechanism of action predicts utility in other diseases."Transplant Proc 30:4126-4126.
Florian et al., 2006, "Detection of molecular targets on the surface of CD34 /CD38—stem cells in various myeloid malignancies"Leukemia. & Lymph. ; 47(2): 207-222.

(Continued)

*Primary Examiner* — Bridget E Bunner
*Assistant Examiner* — Fozia Hamud
(74) *Attorney, Agent, or Firm* — Goodwin Procter LLP

(57) ABSTRACT

The present invention provides antibodies that bind to the IL-3 receptor alpha subunit alpha (Il3Rα) chain, and compositions comprising such antibodies. The present invention provides methods for inhibiting or reducing an IL3Rα-expressing cell population, the methods comprising contacting a population of IL3Rα-expressing cells (e.g., cancer cells and/or cancer stem cells) with an antibody that binds to IL3Rα. The present invention also provides antibody conjugates comprising an antibody that binds to an IL3Rα chain linked to a cytotoxic agent or anticellular agent and compositions comprising such conjugates. The present invention also provides methods for preventing, treating and/or managing a disorder associated with IL3Rα-expressing cells (e.g., a hematological cancer), the methods comprising administering to a subject in need thereof an antibody that binds to IL3Rα.

37 Claims, 13 Drawing Sheets

(56) References Cited

OTHER PUBLICATIONS

Figure 6A:
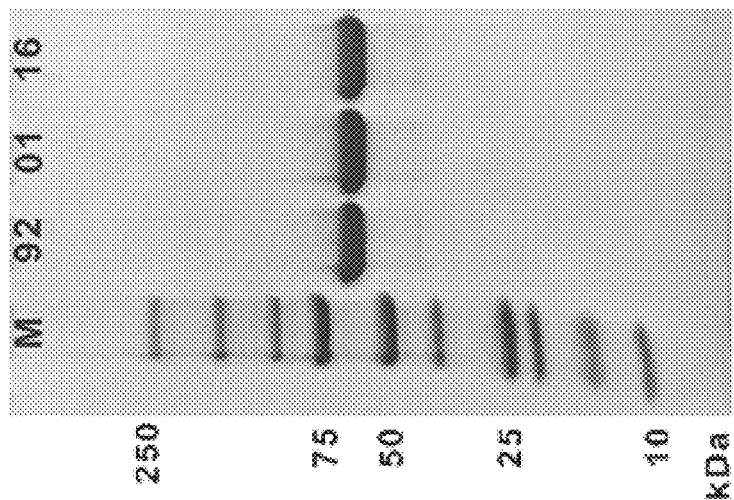

Graf et al., 2004, "Expression and prognostic value of hemopoietic cytokine receptors in acute myeloid leukemia (AML): implications for future therapeutical strategies" Eur J Haematol. 72: 89-106.

Hogge et al., 2004, "Variant diphtheria toxin-interleukin-3 fusion proteins with increased receptor affinity have enhanced cytotoxicity against acute myeloid leukemia progenitors." Clin. Cancer Res. 12:1284-1291.

Jordan et al.,1999, "The interleukin-3 receptor alpha chain is highly expressed on primitive acute myelogenous leukemia," Blood, 94:67A.

Jordan et al., 2000, "The interleukin-3 receptor alpha chain is a unique marker for human acute myelogenous leukemia stein cells"Leukemia 14, 1777-1784.

Koubek et al., 1999, "Occurrence of cytokine receptors on different lymphoid leukaemic cells," Eur. J. Hematol., 63:1-10.

Lhermitie et al., 2006, "Most immature T-ALLs express Ra-IL3 (CD123): possible target for DT-IL3 therapy" Leukemia 20, 1908-1910.

Moretti et al., 2001 "CD123 (interleukin 3 receptor alpha chain)." J Biol Regul Homeost Agents. Jan.-Mar.;15(1):98-100.

Munoz et al., 2001, "Interleukin-3 receptor α chain (CD123) is widely expresssed in hematologic malignancies." Haematol.; 86:1261-1269.

Reiter and Pastan, 1996, "Antibody engineering of recombinant Fv immunotoxins for improved targeting of cancer: disulfide-stabilized Fv immunotoxins". Clin Cancer Res. 2(2):245-252.

Rosenblum et al., 1999, "Recombinant immunotoxins directed against the c-erb-2/HER2/neu oncogene product: in vitro cytotoxicity, pharmacokinetics, and in vivo efficacy studies in xenograft models," Clin. Cancer Res., 5:865-874.

Sun et al., 1996, "Monoclonal antibody 7G3 recognizes the N-terminal domain of the human interleukin-3 (IL-3) receptor alpha-chain and functions as a specific IL-3 receptor antagonist," Blood, 87:83-92.

Testa et al., 2002,"Elevated expression of IL-3Ralpha in acute myelogenous leukemia is associated with enhanced blast proliferation, increased cellularity, and poor prognosis." Blood 100:2980-2988.

Testa, el al 2005, "Diphtheria toxin fused to variant human interleukin-3 induces cytotoxicity of blasts from patients with acute myeloid leukemia according to the level of interleukin-3 receptor expression." . Blood. 106(7):2527-2529.

Tweardy et al., 1992, "Modulation of myeloid proliferation and differentiation by monoclonal antibodies directed against a protein that interacts with the interleukin-3 receptor," Blood, 80:359-366.

26292 VH domain

CAGATCCAGTTGGTGCAGTCTGGACCTGAGCTGAAGAAGCCTGGAGAGACAGTC
AAGATCTCCTGCAAGACTTCTGGATATGTCTTCACAAACTATGGAATGAACTGGG
TGAAACAGGCTCCAGGAAAGGGTTTCAAGTGGATGGGCTGGATGAACACCAACA
CTGGAGAGCCAACATCTCTTGAAGACTTCAAGGGACGGTTTGCCTTCTCTTTGGA
AACCTCTGCCAGCACTGCCTATTTGCAGATCAACAACCTCAAAAATGACGACACG
GCTACATATTTCTGTGCAAGATCGGGGGGTTACGACCCCATGGACTACTGGGGTC
AAGGAACCTCAGTCACCGTCTCCTCA

Figure 1A

26292 VH domain

QVQLQQPGAELVRPGASVKLSCKASGYTFT<u>SYWMN</u>WVKQRPDQGLEWIG<u>RIDPYDSETHYNQ</u>
                                       CDR1                                    CDR2

<u>KFKD</u>KAILTVDKSSSTAYMQLSSLTSEDSAVYYCAR<u>GNWDDY</u>WGQGTTLTVSS
                                      CDR3

Figure 1B

26292 VL domain

GATGTCCAGATAACCCAGTCTCCATCTTATCTTGCTGCATCTCCTGGAGAAACCA
TTACTATTAATTGCAGGGCAAGTAAGAGCATTAGCAAAGATTTAGCCTGGTATCA
AGAGAAACCTGGGAAAACTAATAAGCTTCTTATCTACTCTGGATCCACTTTGCAA
TCTGGAATTCCATCAAGGTTCAGTGGCAGTGGATCTGGTACAGATTTCACTCTCA
CCATTAGTAGCCTGGAGCCTGAAGATTTTGCAATGTATTATTGTCAACAACATAA
TAAATATCCGTACACGTTCGGAGGGGGGACCAAGCTGGAAATAAAA

Figure 1C

26292 VL domain

DVQITQSPSYLAASPGETITINC<u>RASKSISKDLA</u>WYQEKPGKTNKLLIY<u>SGSTLQS</u>GIPSRF
                                       CDR1                                                 CDR2

SGSGSGTDFTLTISSLEPEDFAMYYC<u>QQHNKYPYT</u>FGGGTKLEIK
                             CDR3

Figure 1D

32703 VH domain

CAGGTCCAACTGCAGCAGCCTGGGGCTGAACTTGTGAAGCCTGGGGCTCCAGTG
AAGCTGTCCTGCAAGGCTTCTGGCTACACCTTCACCAACTACTGGATGAACTGGA
TTAAACAGAGGCCTGGACGAGGCCTCGAGTGGATTGGAAGGATTGATCCCTCCG
ATAGTGAAAGTCACTACAATCAAAAGTTCAAGGACAAGGCCACACTGACTGTTG
ACAAATCCTCCAATACAGCCTACATCCAACTCAGCAGTCTGACATCTGAGGACTC
TGCGGTCTATTACTGTGCAAGATATGATTACGACGATACTATGGACTACTGGGGT
CAAGGAACCTCAGTCACCGTCTCCTCA

Figure 2A

32703 VH domain

QVQLQQPGAELVKPGAPVKLSCKASGYTFT<u>NYWMN</u>WIKQRPGRGLEWIG<u>RIDPSDSESHYNQ</u>
                                   CDR1                                                    CDR2

K<u>FKD</u>KATLTVDKSSNTAYIQLSSLTSEDSAVYYCAR<u>YDYDDTMDY</u>WGQGTSVTVSS
                                                   CDR3

Figure 2B

32703 VL domain

GATATTGTGATGACTCAGGCTGCACCCTCTGTCCCTGTCACTCCTGGAGAGTCCG
TATCCATCTCCTGCAGGTCTAATAAGAGTCTCCTGCATAGTAATGGCAACACTTA
CTTGTATTGGTTCCTGCAGAGGCCAGGCCAGTCTCCTCAGCTCCTGATATATCGG
ATGTCCAACCTTGCCTCAGGAGTCCCAGACAGGTTCAGTGGCAGTGGGTCAGGA
ACTGCTTTCACACTGAGAATCAGTAGAGTGGAGGCTGAGGATGTGGGTGTTTATT
ACTGTATGCAACATCTAGAATATCCGTACACGTTCGGAGGGGGGACCAAGCTGG
AAATAAAA

Figure 2C

32703 VL domain

DIVMTQAAPSVPVTPGESVSISC<u>RSNKSLLHSNGNTYLY</u>WFLQRPGQSPQLLIY<u>RMSNLASG</u>
            CDR1                CDR2

VPDRFSGSGSGTAFTLRISRVEAEDVGVYYC<u>MQHLEYPYT</u>FGGGTKLEIK
               CDR3

Figure 2D

32701 VH domain

CAGATCCAGTTGGTGCAGTCTGGACCTGAGCTGAAGAAGCCTGGAGAGACAGTC
AAGATCTCCTGCAAGACTTCTGGATATGTCTTCACAAACTATGGAATGAACTGGG
TGAAACAGGCTCCAGGAAAGGGTTTCAAGTGGATGGGCTGGATGAACACCAACA
CTGGAGAGCCAACATCTCTTGAAGACTTCAAGGGACGGTTTGCCTTCTCTTTGGA
AACCTCTGCCAGCACTGCCTATTTGCAGATCAACAACCTCAAAAATGACGACACG
GCTACATATTTCTGTGCAAGATCGGGGGGTTACGACCCCATGGACTACTGGGGTC
AAGGAACCTCAGTCACCGTCTCCTCA

Figure 3A

32701 VH domain

QIQLVQSGPELKKPGETVKISCKTSGYVFT<u>NYGMN</u>WVKQAPGKGFKWMG<u>WMNTNTGEPTSLE</u>
                                     CDR1                                   CDR2

<u>DFKG</u>RFAFSLETSASTAYLQINNLKNDDTATYFCAR<u>SGGYDPMDY</u>WGQGTSVTVSS
                                      CDR3

Figure 3B

32701 VL domain

GACATTGTGCTGACCCAATCTCCAGCTTCTTTGGCTGTGTCTCCAGGGCAGAGGG
CCACCATATCCTGCAGAGCCAGTGAAAGTGTTGATAATTATGGCAATACTTTTAT
GCACTGGTACCAGCAGAAACCAGGACAGCCACCCAAACTCCTCATCTATCGTGC
ATCCAACCTAGAATCTGGGATCCCTGCCAGGTTCAGTGGCAGTGACTCTAGGACA
GACTTCACCCTCACCATTAATCCTGTGGAGGCTGATGATGTTGCAACCTATTACT
GTCAGCAAAGTAAAGAGGATCCTCCACGTTCGGTGCTGGGACTAAGCTGGAGC
TGAAA

Figure 3C

32701 VL domain

DIVLTQSPASLAVSPGQRATISC<u>RASESVDNYGNTFMH</u>WYQQKPGQPPKLLIY<u>RASNLES</u>GI
                                  CDR1                                                        CDR2

PARFSGSDSRTDFTLTINPVEADDVATYYC<u>QQSKEDPPT</u>FGAGTKLELK
                                CDR3

Figure 3D

32716 VH domain

CAGATCCAGTTGGTGCAGTCTGGACCTGAGCTGAAGAAGCCTGGAGAGACAGTC
AAGATCTCCTGCAAGGCTTCTGGGTATATTTTCACAAACTATGGAATGAACTGGG
TGAAGCAGGCTCCAGGAAAGAGTTTTAAGTGGATGGGCTGGATAAACACCTACA
CTGGAGAGTCAACATATAGTGCTGACTTCAAGGGACGGTTTGCCTTCTCTTTGGA
AACCTCTGCCAGCACTGCCTATTTGCATATCAACGACCTCAAAAATGAGGACACG
GCTACATATTTCTGTGCAAGATCGGGGGGTTACGACCCCATGGACTACTGGGGTC
AAGGAACCTCAGTCACCGTCTCCTCA

Figure 4A

32716 VH domain

QIQLVQSGPELKKPGETVKISCKASGYIFTNYGMNWVKQAPGKSFKWMGWINTYTGESTYSA
           CDR1            CDR2

DFKGRFAFSLETSASTAYLHINDLKNEDTATYFCARSGGYDPMDYWGQGTSVTVSS
                   CDR3

Figure 4B

32716 VL domain

GACATTGTACTGACCCAATCTCCAGCTTCTTTGGCTGTGTCTCTAGGGCAGAGGG
CCACCATATCCTGCAGAGCCAGTGAAAGTGTTGATAATTATGGCAATACTTTTAT
GCACTGGTACCAGCAGAAACCAGGACAGCCACCCAAACTCCTCATCTATCGTGC
ATCCAACCTAGAATCTGGGATCCCTGCCAGGTTCAGTGGCAGTGGGTCTAGGACA
GACTTCACCCTCACCATTAATCCTGTGGAGGCTGATGATGTTGCAACCTATTACT
GTCAGCAAAGTAATGAGGATCCTCCCACGTTCGGTGCTGGGACCAAGCTGGAGC
TGAAA

Figure 4C

32716 VL domain

DIVLTQSPASLAVSLGQRATISC<u>RASESVDNYGNTFMH</u>WYQQKPGQPPKLLIY<u>RASNLES</u>GI
                                CDR1                                                     CDR2

PARFSGSGSRTDFTLTINPVEADDVATYYC<u>QQSNEDPPT</u>FGAGTKLELK
                                   CDR3

Figure 4D

Figures 5A-5B

FIG. 7A
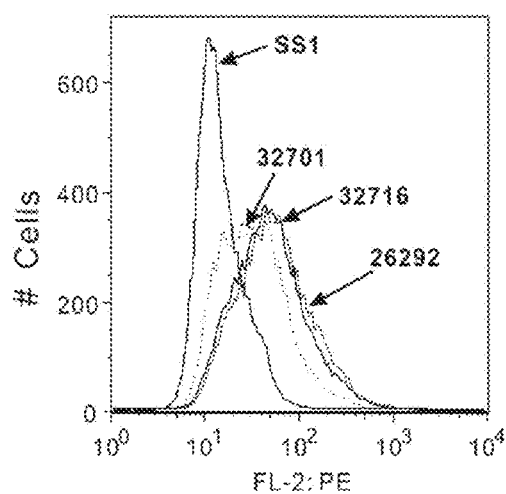
FIG. 7B
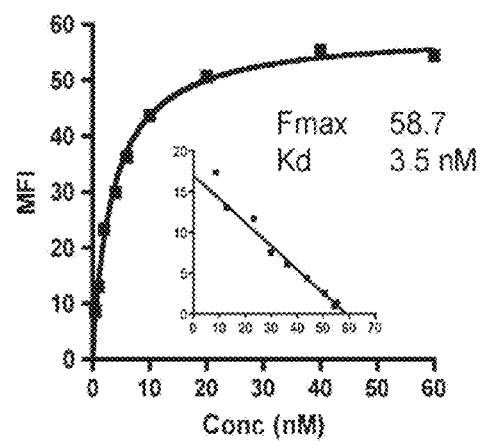
FIG. 7C
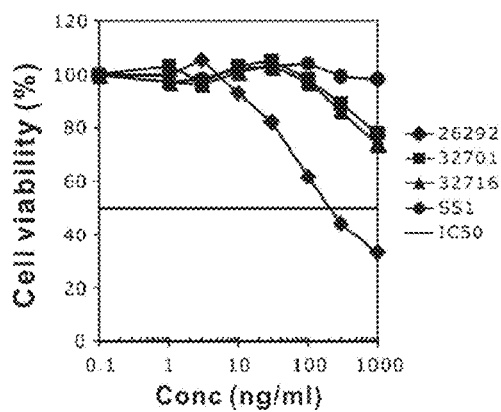
FIG. 7D
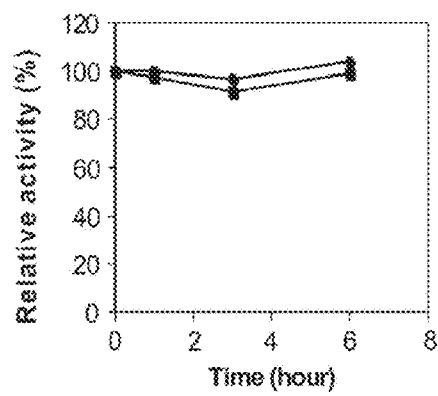
Figures 7A-7D

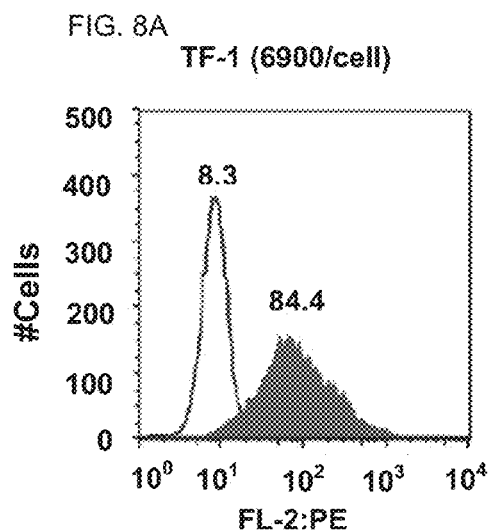
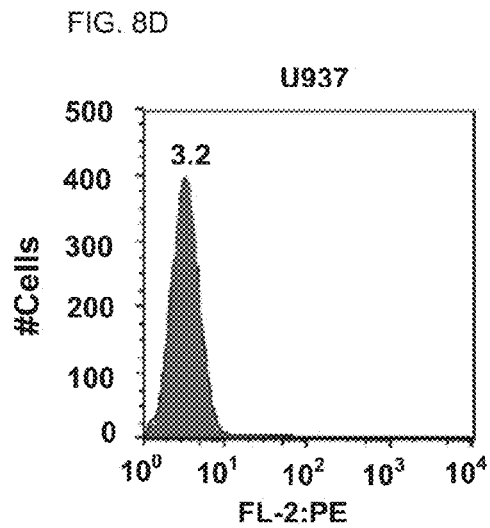
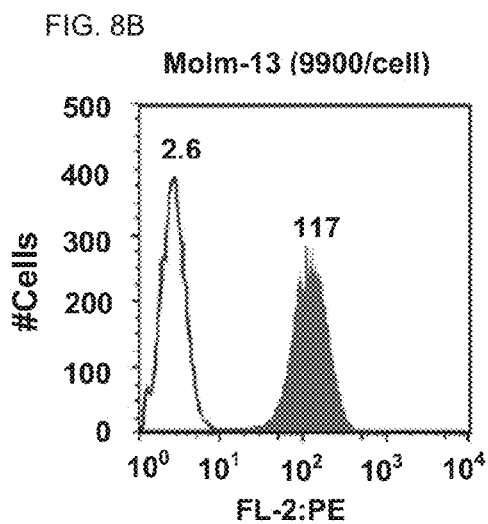
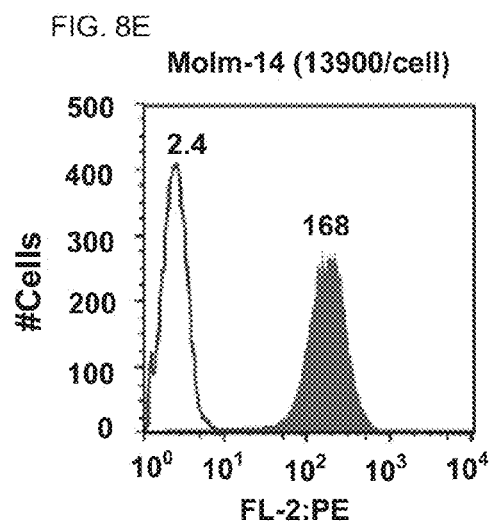
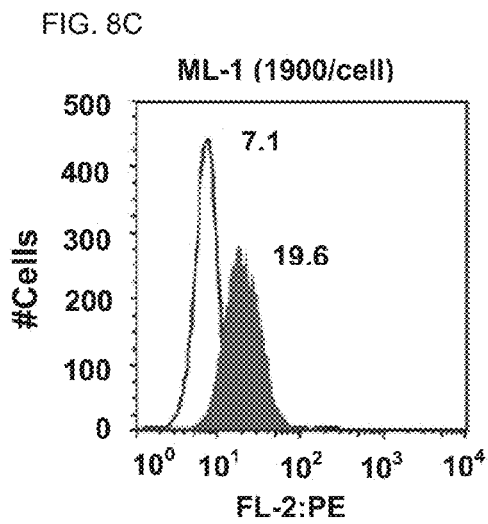
Figure 8 A-E

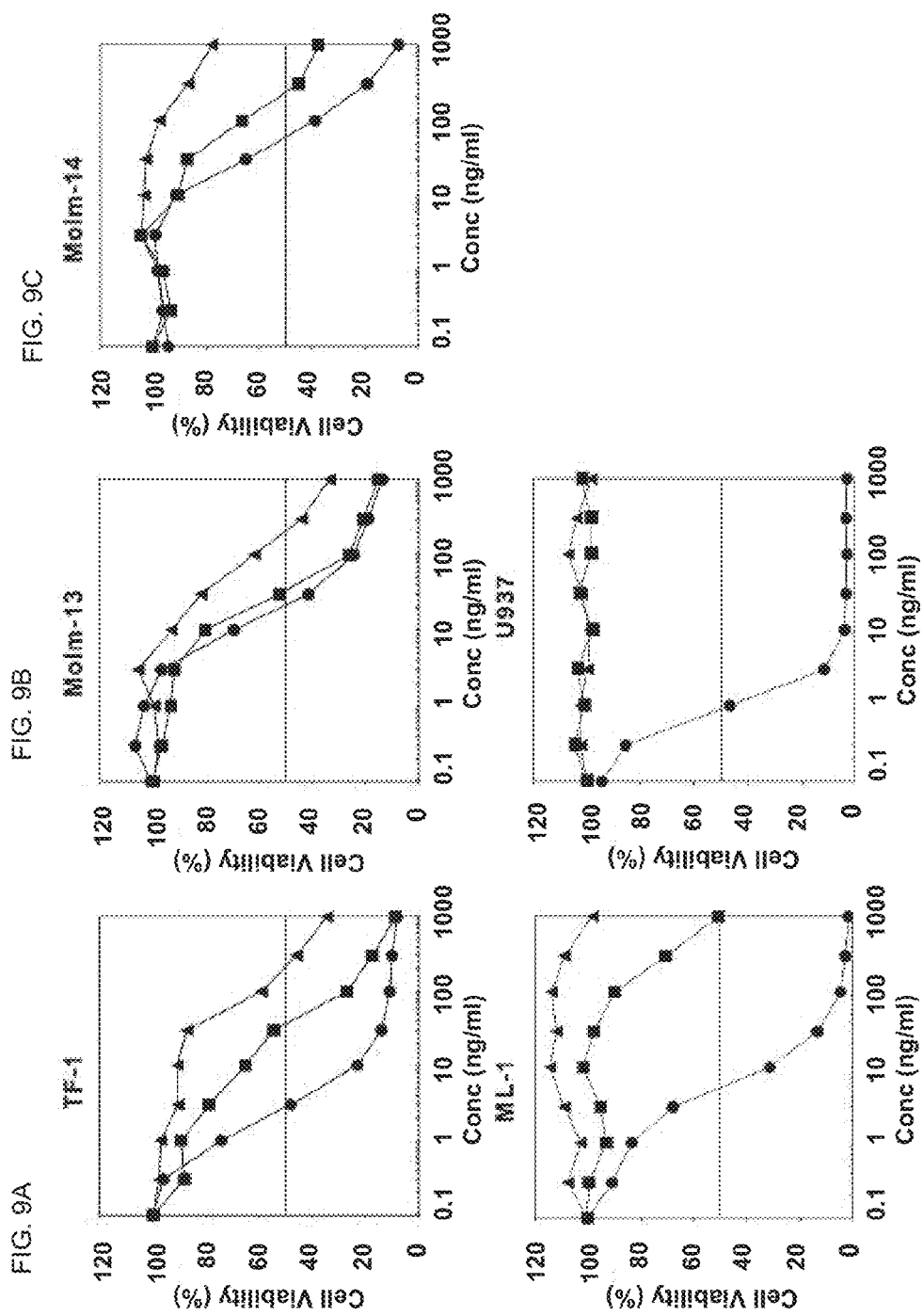
Figure 9 A-E

IL3Rα ANTIBODY CONJUGATES AND USES THEREOF

This application is a continuation of U.S. application Ser. No. 13/439,453, filed Apr. 4, 2012, which is a continuation of U.S. application Ser. No. 12/082,940, filed Apr. 14, 2008, now U.S. Pat. No. 8,163,279, which claims the benefit of U.S. Provisional Application No. 60/923,499 filed Apr. 13, 2007, the disclosure of each of which is incorporated herein by reference in its entirety.

1. FIELD OF THE INVENTION

The present invention provides methods for inhibiting or reducing an IL-3 receptor alpha subunit alpha (IL3Rα)-expressing cell population, the methods comprising contacting a population of IL3Rα-expressing cells (e.g., cancer cells and/or cancer stem cells) with an antibody that binds to IL3Rα. The present invention also provides methods for preventing, treating and/or managing a disorder associated with IL3Rα-expressing cells (e.g., a hematological cancer), the methods comprising administering to a subject in need thereof an antibody that binds to IL3Rα.

2. BACKGROUND OF THE INVENTION

2.1 Cancer Therapy

Cancer is one of the most significant health conditions. The American Cancer Society's *Cancer Facts and Figures*, 2003, predicts over 1.3 million Americans will receive a cancer diagnosis this year. In the United States, cancer is second only to heart disease in mortality accounting for one of four deaths. In 2002, the National Institutes of Health estimated total costs of cancer totaled $171.6 billion, with $61 billion in direct expenditures. The incidence of cancer is widely expected to increase as the US population ages, further augmenting the impact of this condition. The current treatment regimens for cancer established in the 1970s and 1980s, have not changed dramatically. These treatments, which include chemotherapy, radiation and other modalities including newer targeted therapies, have shown limited overall survival benefit when utilized in most advanced stage common cancers since, among other things, these therapies primarily target tumor bulk.

More specifically, conventional cancer diagnosis and therapies to date have attempted to selectively detect and eradicate neoplastic cells that are largely fast-growing (i.e., cells that form the tumor bulk). Standard oncology regimens have often been largely designed to administer the highest dose of irradiation or a chemotherapeutic agent without undue toxicity, i.e., often referred to as the "maximum tolerated dose" (MTD) or "no observed adverse effect level" (NOAEL). Many conventional cancer chemotherapies (e.g., alkylating agents such as cyclophosphamide, antimetabolites such as 5-Fluorouracil, and plant alkaloids such as vincristine) and conventional irradiation therapies exert their toxic effects on cancer cells largely by interfering with cellular mechanisms involved in cell growth and DNA replication. Chemotherapy protocols also often involve administration of a combination of chemotherapeutic agents in an attempt to increase the efficacy of treatment. Despite the availability of a large variety of chemotherapeutic agents, these therapies have many drawbacks (see, e.g., Stockdale, 1998, "Principles Of Cancer Patient Management" in Scientific American Medicine, vol. 3, Rubenstein and Federman, eds., ch. 12, sect. X). For example, chemotherapeutic agents are notoriously toxic due to non-specific side effects on fast-growing cells whether normal or malignant; e.g. chemotherapeutic agents cause significant, and often dangerous, side effects, including bone marrow depression, immunosuppression, and gastrointestinal distress, etc.

Other types of traditional cancer therapies include surgery, hormonal therapy, immunotherapy, anti-angiogenesis therapy, targeted therapy (e.g., therapy directed to a cancer target such as Gleevec® and other tyrosine kinase inhibitors, Velcade®, Sutent®, et al.), and radiation treatment to eradicate neoplastic cells in a patient (see, e.g., Stockdale, 1998, "Principles of Cancer Patient Management," in Scientific American: Medicine, vol. 3, Rubenstein and Federman, eds., ch. 12, sect. IV). All of these approaches can pose significant drawbacks for the patient including a lack of efficacy (in terms of long-term outcome (e.g. due to failure to target cancer stem cells) and toxicity (e.g. due to non-specific effects on normal tissues)). Accordingly, new therapies for improving the long-term prospect of cancer patients are needed.

2.2 Cancer Stem Cells

Cancer stem cells comprise a unique subpopulation (often 0.1-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e. those cancer cells that comprise the tumor bulk), cancer stem cells which are often slow-growing may be relatively more resistant than faster growing tumor bulk to conventional therapies and regimens. Cancer stem cells can express other features which make them relatively chemoresistant such as multi-drug resistance and anti-apoptotic pathways. The aforementioned would constitute a key reason for the failure of standard oncology treatment regimens to ensure long-term benefit in most patients with advanced stage cancers—i.e. the failure to adequately target and eradicate cancer stem cells. In some instances, a cancer stem cell(s) is the founder cell of a tumor (i.e., it is the progenitor of the cancer cells that comprise the tumor bulk).

Cancer stem cells have been identified in a large variety of cancer types. For instance, Bonnet et al., using flow cytometry were able to isolate the leukemia cells bearing the specific phenotype CD34+ CD38−, and subsequently demonstrate that it is these cells (comprising <1% of a given leukemia), unlike the remaining 99+% of the leukemia bulk, that are able to recapitulate the leukemia from whenst it was derived when transferred into immunodeficient mice. See, e.g., "Human acute myeloid leukemia is organized as a hierarchy that originates from a primitive hematopoietic cell," *Nat. Med.* 3:730-737 (1997). That is, these cancer stem cells were found as <1 in 10,000 leukemia cells yet this low frequency population was able to initiate and serially transfer a human leukemia into severe combined immunodeficiency/non-obese diabetic (NOD/SCID) mice with the same histologic phenotype as in the original tumor.

Cox et al. identified small subfractions of human acute lymphoblastic leukemia (ALL) cells which had the phenotypes CD34+/CD10− and CD34+/CD19−, and were capable of engrafting ALL tumors in immunocompromised mice—i.e. the cancer stem cells. In contrast, no engraftment of the mice was observed using the ALL bulk, despite, in some cases, injecting 10-fold more cells. See Cox et al., "Characterization of acute lymphoblastic leukemia progenitor cells," *Blood* 104(19): 2919-2925 (2004).

Multiple myeloma was found to contain small subpopulations of cells that were CD138− and, relative to the large bulk population of CD138+ myeloma cells, had greater clonogenic and tumorigenic potential. See Matsui et al., "Characterization of clonogenic multiple myeloma cells," *Blood* 103(6): 2332. The authors concluded that the CD138− subpopulation of multiple myeloma was the cancer stem cell population.

Kondo et al. isolated a small population of cells from a C6-glioma cell line, which was identified as the cancer stem cell population by virtue of its ability to self-renew and recapitulate gliomas in immunocompromised mice. See Kondo et al., "Persistence of a small population of cancer stem-like cells in the C6 glioma cell line," *Proc. Natl. Acad. Sci. USA* 101:781-786 (2004). In this study, Kondo et al. determined that cancer cell lines contain a population of cancer stem cells that confer the ability of the line to engraft immunodeficient mice.

Breast cancers were shown to contain a small population of cells with stem cell characteristics (bearing surface markers CD44+CD24$^{low\ lin-}$). See Al-Hajj et al., "Prospective identification of tumorigenic breast cancer cells," *Proc. Natl. Acad. Sci. USA* 100:3983-3988 (2003). As few as 200 of these cells, corresponding to 1-10% of the total tumor cell population, are able to form tumors in NOD/SCID mice. In contrast, implantation of 20,000 cells that lacked this phenotype (i.e. the tumor bulk) was unable to re-grow the tumor.

A subpopulation of cells derived from human prostate tumors was found to self-renew and to recapitulate the phenotype of the prostate tumor from which they were derived thereby constituting the prostate cancer stem cell population. See Collins et al., "Prospective Identification of Tumorigenic Prostate Cancer Stem Cells," *Cancer Res* 65(23):10946-10951 (2005).

Fang et al. isolated a subpopulation of cells from melanoma with cancer stem cell properties. In particular, this subpopulation of cells could differentiate and self-renew. In culture, the subpopulation formed spheres whereas the more differentiated cell fraction from the lesions were more adherent. Moreover, the subpopulation containing sphere-like cells were more tumorigenic than the adherent cells when grafted into mice. See Fang et al., "A Tumorigenic Subpopulation with Stem Cell Properties in Melanomas," *Cancer Res* 65(20): 9328-9337 (2005).

Singh et al. identified brain tumor stem cells. When isolated and transplanted into nude mice, the CD133+ cancer stem cells, unlike the CD133− tumor bulk cells, form tumors that can then be serially transplanted. See Singh et al., "Identification of human brain tumor initiating cells," *Nature* 432:396-401 (2004); Singh et al., "Cancer stem cells in nervous system tumors," *Oncogene* 23:7267-7273 (2004); Singh et al., "Identification of a cancer stem cell in human brain tumors," *Cancer Res.* 63:5821-5828 (2003).

Since conventional cancer therapies target rapidly proliferating cells (i.e., cells that form the tumor bulk) these treatments are believed to be relatively ineffective at targeting and impairing cancer stem cells. In fact, cancer stem cells, including leukemia stem cells, have indeed been shown to be relatively resistant to conventional chemotherapeutic therapies (e.g. Ara-C, daunorubicin) as well as newer targeted therapies (e.g. Gleevec®, Velcade®). Examples of cancer stem cells from various tumors that are resistant to chemotherapy, and the mechanism by which they are resistant, are described in Table 1 below.

TABLE 1

| CSC Type | Resistance | Mechanism | Reference |
|---|---|---|---|
| AML | Ara-C | Quiescence | Guzman. Blood '01 |
| AML | Daunorubicin | Drug Efflux, Anti-apoptosis | Costello. Cancer Res '00 |
| AML | Daunorubicin, mitoxantrone | Drug Efflux | Wulf. Blood '01 |
| AML | | Quiescence | Guan. Blood '03 |
| AML, MDS | | Anti-apoptosis | Suarez. Clin Cancer Res '04 |
| CML | | Quiescence | Holyoake. Blood '99 |
| CML | Gleevec ® | Quiescence | Graham. Blood '02 |
| Myeloma | Velcade ® | | Matsui. ASH 04 |

For example, leukemic stem cells are relatively slow-growing or quiescent, express multi-drug resistance genes, and utilize other anti-apoptotic mechanisms—features which contribute to their chemoresistance. See Jordan et al., "Targeting the most critical cells: approaching leukemia therapy as a problem in stem cell biology," *Nat. Clin. Pract. Oncol.* 2: 224-225 (2005). Further, cancer stem cells by virtue of their chemoresistance may contribute to treatment failure, and may also persist in a patient after clinical remission and these remaining cancer stem cells may therefore contribute to relapse at a later date. See Behbood et al., "Will cancer stem cells provide new therapeutic targets?" *Carcinogenesis* 26(4): 703-711 (2004). Therefore, targeting cancer stem cells is expected to provide for improved long-term outcomes for cancer patients. Accordingly, new therapeutic agents and/or regimens designed to target cancer stem cells are needed to reach this goal.

2.3 Acute Myeloid Leukemia

Approximately forty thousand patients per year develop acute myeloid leukemia (AML) in the U.S., Canada, and Europe. See, e.g., Jamal et al., *Cancer Statistics* 56:106-130 (2006). AML is the most common leukemia in adults and the second most common leukemia in children. The prolonged hospitalizations associated with treatment and complications represent a significant share of health care costs in these regions. Further, even with combination induction and consolidation chemotherapy, most patients ultimately relapse and die from their disease or complications of treatment. See, e.g., Brune et al., "Improved leukemia-free survival after post-consolidation immunotherapy with histamine dihydrochloride and interleukin-2 in acute myeloid leukemia: results of a randomized phase III trial," *Blood* 108(1): 88-96 (2006). Novel therapies are urgently needed. Selective targeting of AML cells stem cells may provide a safe and more effective therapy.

2.4 Myelodysplastic Syndrome

There are approximately 20,000 new cases of myelodysplastic syndrome (MDS) each year in the U.S. Patients with myelodysplastic syndromes typically have low blood cell counts in at least one or more of red blood cells, white blood cells, and platelets. Upon examination, the bone marrow usually is found to be dysplastic or hyperplastic, meaning there are too many poorly functioning blood stem cells in the marrow. A small percentage of MDS patients have hypoplastic bone marrow, meaning there are too few blood stem cells in the marrow, which make the disease look similar to aplastic anemia. Nearly half of people with MDS have no symptoms at time of diagnosis. When signs and symptoms do occur they can include anemia, weakness, fatigue, headache, bruising, increased bleeding, rash, fevers, mouth sores and lingering illness. MDS occurs at an increasing frequency in older people, but it can occur in children too. In less than a third of patients, MDS progresses over time to become acute leukemia. The average age of diagnosis is 70 years old. Treatments for MDS may vary considerably, depending on the type of MDS, the history of the patient, and the age and ability to tolerate certain treatment regimens. Treatment options include supportive care, chemotherapy-related agents, and stem cell transplantation (which is typically used only in patients under 50). However, the remission rate for existing treatments in relatively low, and new therapies are needed.

2.5 Interleukin-3 and the IL-3 Receptor Alpha Subunit

Interleukin-3 (IL-3) is a cytokine that supports the proliferation and differentiation of multipotential and committed myeloid and lymphoid progenitors, but is not required for growth and differentiation of normal stem cells and mature myeloid cells. See, e.g., Nitsche et al., "Interleukin-3 promotes proliferation and differentiation of human hematopoietic stem cells but reduces their repopulation potential in NOD/SCID mice," *Stem Cells* 21:236-244 (2003).

Human IL-3 mediates its effects by binding to the human IL-3 receptor, which is a heterodimer consisting of an IL-3-binding alpha subunit (IL3Rα, CD123) and a common beta subunit (IL3Rβ$_c$). The alpha subunit of IL3R is essential for ligand binding and specificity. The α subunit is essential for ligand binding and confers specificity on the receptor. The β subunit is also shared by the granulocyte macrophage-colony stimulating factor (GM-CSF) and IL-5 receptors, and is required for high affinity ligand binding and signal transduction.

The alpha subunit of the human IL-3 receptor is strongly expressed in 45%-95% of AML, 40%-100% of B-cell lineage acute lymphocytic leukemia (B-ALL), and 85% of hairy cell leukemia (HCL). See, e.g., Graf et al., "Expression and prognostic value of hemopoietic cytokine receptors in acute myeloid leukemia (AML): implications for future therapeutical strategies," *Eur. J. Haematol.* 72:89-106 (2004); Jordan et al., "The IL-3 receptor alpha subunit alpha chain is a unique marker for human acute myelogenous leukemia stem cells," *Leukemia* 14:1777-1784 (2000); Munoz et al., "IL-3 receptor alpha subunit alpha chain (CD123) is widely expressed in hematologic malignancies," *Haematologica* 86:1261-1269 (2001); Testa et al., "Elevated expression of IL-3R alpha in acute myelogenous leukemia is associated with enhanced blast proliferation, increased cellularity, and poor prognosis," *Blood* 100:2980-2988 (2002). The common β subunit of the IL-3 receptor is shared by the IL-3, granulocyte-macrophage colony-stimulating factor (GM-CSF), and IL-5 receptors. See, e.g., Testa et al., "IL-3 receptor alpha subunit in acute leukemia," *Leukemia* 18:219-226 (2004). The expression of IL3Rα is elevated in the primitive LSC population (CD34+/CD38−) in AML, chronic myelogenous leukemia (CML), and some other myeloid malignancies, but is not detectable in normal hematopoietic cells and progenitors. See, e.g., Florian et al., "Detection of molecular targets on the surface of CD34+/CD38− stem cells in various myeloid malignancies," *Leuk. Lymphoma* 47:207-222 (2006); Jordan et al., 2000, above; Hogge et al., "Variant Diphtheria Toxin-Interleukin-3 Conjugates with Increased Receptor Affinity Have Enhanced Cytotoxicity against Acute Myeloid Leukemia Progenitors," *Clin. Cancer Res.* 12:1284-1291 (2004). Thus, IL3Rα appears to be an excellent target for the therapy of leukemias.

3. SUMMARY OF THE INVENTION

The present invention provides pharmaceutical compositions comprising an antibody that binds to the IL3Rα chain, and a pharmaceutically acceptable carrier or excipient. In one aspect, the invention provides pharmaceutical compositions comprising an antibody that binds to the IL3Rα chain in an amount effective to reduce cancer stem cells and/or cancer cells in an animal with or animal model for myeloid leukemia or another cancer associated with IL3Rα-expressing cells by about 25%, about 30%, 35%, about 40%, about 45%, about 50%, about 65%, about 75% or more relative to a negative control. In a specific embodiment, the antibody incorporated into a pharmaceutical composition has a dissociation constant ($K_d$) of less than 4 nM on cells expressing the IL3Rα chain (e.g., erytholeukemic cells, myeloid cells or myeloblastic cells). In another embodiment, the antibody incorporated into a pharmaceutical composition comprises a variable heavy (VH) domain having the amino acid sequence of SEQ ID NO:2, 12, 22, or 32, and/or a variable light (VL) domain having the amino acid sequence of SEQ ID NO: 7, 17, 27 or 37. In another embodiment, the antibody incorporated into a pharmaceutical composition comprises one or more of the VH complementarity determining regions (CDRs) shown in FIGS. 1B, 2B, 3B and/or 4B and/or a VL domain comprising one or more of the VL CDRs shown in FIGS. 1D, 2D, 3D and/or 4D. In another embodiment, the antibody incorporated into a pharmaceutical composition competes with an antibody comprising a VH domain having the amino acid sequence of SEQ ID NO:2, 12, 22, or 32 and a VL domain having the amino acid sequence of SEQ ID NO: 7, 17, 27 or 37 for binding to the IL3Rα chain. In some embodiments, a pharmaceutical composition of the invention comprises an agent in addition to an antibody of the invention.

The present invention also provides methods for inhibiting the proliferation or reducing an IL3Rα-expressing cell population, the methods comprising contacting a population of cells comprising IL3Rα-expressing cells with an antibody that binds to the IL3 Rα chain. In a specific embodiment, the present invention provides methods for inhibiting the proliferation or reducing the population of cancer stem cells expressing IL3Rα, the methods comprising contacting the IL3Rα-expressing cancer stem cell population with an antibody that binds to the IL3Rα chain. In another embodiment, the present invention provides methods for inhibiting the proliferation or reducing the population of cancer cells expressing IL3Rα, the methods comprising contacting the IL3Rα-expressing cancer cell population with an antibody that binds to the IL3Rα chain. In yet another embodiment, the present invention provides methods for inhibiting the proliferation or reducing the population cancer cells and cancer stem cells expressing IL3Rα, the methods comprising contacting a population of cells comprising IL3Rα-expressing cancer cells and/or IL3Rα-expressing cancer stem cells with an antibody that binds to the IL3Rα chain. In certain embodiments, the antibody reduces a cancer stem cell population and/or a cancer cell population by at least 25%, at least 30%, at least 40%, at least 50%, at least 65%, at least 75%, or at least 85% in an animal with or animal model for myeloid leukemia or another cancer associated with IL3Rα-expressing cells relative to a negative control.

The present invention also provides methods for preventing, treating and/or managing a disorder associated with IL3Rα-expressing cells (e.g., a hematologic cancer), the methods comprising administering to a subject in need thereof an antibody that binds to the IL3 Rα chain. In a specific embodiment, the present invention provides a method for preventing, treating and/or managing a disorder associated with IL3Rα-expressing cells (e.g., a hematologic cancer), the method comprising administering to a human subject in need thereof an effective amount of an antibody that binds to the IL3 Rα chain, and in some embodiments, an effective amount of another therapy. Non-limiting examples of disorders associated with IL3Rα-expressing cells include autoimmune disorders (such as lupus), inflammatory disorders (such as allergies and asthma) and cancers (such as hematological cancers). In some embodiments, the disorder associated with IL3Rα-expressing cells is not myeloid leukemia.

The present invention provides methods for preventing relapse of cancer associated with IL3Rα-expressing cells, the methods comprising administering to a subject in need thereof an antibody that binds to the IL3 Rα chain. In a specific embodiment, the present invention provides methods for preventing relapse of cancer associated with IL3Rα-expressing cells, the methods comprising administering to a human subject in need thereof an effective amount of an antibody that binds to the IL3 Rα chain, and in some embodiments, an effective amount of another therapy. In some embodiments, the cancer associated with IL3Rα-expressing cells is not myeloid leukemia.

The present invention provides methods for preventing, treating and/or managing cancer associated with IL3Rα-expressing cells (e.g., a hematologic cancer), the method comprising administering to a human subject in need thereof an antibody that binds to the IL3 Rα chain in an amount effective to reduce the quantity, number, amount or percentage of cancer stem cells and/or cancer cells by at least 25%, at least 30%, at least 40%, at least 50%, at least 65%, at least 75%, or at least 85% in an animal with or animal model for myeloid leukemia or another cancer associated with IL3Rα-expressing cells relative to a negative control.

The present invention provides antibody conjugates comprising an antibody that binds to the alpha chain of the IL-3 receptor alpha subunit (IL3Rα, CD123) linked to a cytotoxic agent or other moiety, and compositions comprising such conjugates and uses of such conjugates, including the prevention, management and/or treatment of a disorder associated with IL3Rα-expressing cells. In a specific embodiment, the antibody conjugate is an immunotoxin. In one aspect, the present invention provides an antibody conjugate comprising an antibody that binds to the IL3Rα chain linked to a cytotoxic agent, wherein the antibody conjugate has an IC50 of less than 40 ng/ml on cells expressing the IL3Rα chain. In a specific embodiment, the antibody has a dissociation constant ($K_d$) of less than 4 nM on cells expressing the IL3Rα chain (e.g., erytholeukemic cells, myeloid cells or myeloblastic cells).

In another aspect, the present invention provides an antibody conjugate comprising an antibody that binds to the IL3Rα chain linked to a cytotoxic agent, wherein the antibody comprises a variable heavy (VH) domain having the amino acid sequence of SEQ ID NO:2, 12, 22, or 32, and/or a variable light (VL) domain having the amino acid sequence of SEQ ID NO: 7, 17, 27 or 37. In one embodiment, the antibody comprises a variable heavy (VH) domain having the amino acid sequence of SEQ ID NO:2 (FIG. 1B), and/or a variable light (VL) domain having the amino acid sequence of SEQ ID NO: 7 (FIG. 1D). In another embodiment, the antibody comprises a variable heavy (VH) domain having the amino acid sequence of SEQ ID NO: 12 (FIG. 2B), and/or a variable light (VL) domain having the amino acid sequence of SEQ ID NO: 17 (FIG. 2D). In yet another embodiment, the antibody comprises a variable heavy (VH) domain having the amino acid sequence of SEQ ID NO: 22 (FIG. 3B), and/or a variable light (VL) domain having the amino acid sequence of SEQ ID NO: 27 (FIG. 3D). In yet another embodiment, the antibody comprises a variable heavy (VH) domain having the amino acid sequence of SEQ ID NO: 32 (FIG. 4B), and/or a variable light (VL) domain having the amino acid sequence of SEQ ID NO: 37 (FIG. 4D).

In another aspect, the present invention provides an antibody conjugate comprising an antibody that binds to the ILR3α chain linked to a cytotoxic agent, wherein the antibody comprises one or more of the VH complementarity determining regions (CDRs) shown in FIGS. 1B, 2B, 3B and/or 4B and/or a VL domain comprising one or more of the VL CDRs shown in FIGS. 1D, 2D, 3D and/or 4D. In one embodiment, the antibody comprises a VH domain comprising one or more of the VH CDRs shown in FIG. 1B (SEQ ID NO: 3, 4, or 5) and/or a VL domain comprising one or more of the VL CDRs shown in FIG. 1D (SEQ ID NO: 8, 9, or 10). In another embodiment, the antibody comprises a VH domain comprising one or more of the VH CDRs shown in FIG. 2B (SEQ ID NO: 13, 14, or 15) and/or a VL domain comprising one or more of the VL CDRs shown in FIG. 2D (SEQ ID NO: 18, 19, or 20). In another embodiment, the antibody comprises a VH domain comprising one or more of the VH CDRs shown in FIG. 3B (SEQ ID NO: 23, 24, or 25) and/or a VL domain comprising one or more of the VL CDRs shown in FIG. 3D (SEQ ID NO: 28, 29, or 30). In yet another embodiment, the antibody comprises a VH domain comprising one or more of the VH CDRs shown in FIG. 4B (SEQ ID NO: 33, 34, or 35) and/or a VL domain comprising one or more of the VL CDRs shown in FIG. 4D (SEQ ID NO: 38, 39, or 40).

In another aspect, the present invention provides an antibody conjugate comprising an antibody that binds to the IL3Rα chain linked to a cytotoxic agent, wherein the antibody competes with an antibody comprising a VH domain having the amino acid sequence of SEQ ID NO:2, 12, 22, or 32 and a VL domain having the amino acid sequence of SEQ ID NO: 7, 17, 27 or 37 for binding to the IL3Rα chain. In a specific embodiment, the present invention provides an antibody conjugate comprising an antibody that binds to the IL3Rα chain linked to a cytotoxic agent, wherein the antibody binds to the same epitope or an epitope that overlaps the epitope of an antibody comprising a VH domain having the amino acid sequence of SEQ ID NO:2, 12, 22, or 32 and a VL domain having the amino acid of SEQ ID NO: 7, 17, 27 or 37. In some embodiments, the antibody has a dissociation constant ($K_d$) of less than 4 nM on cells expressing the IL3Rα chain (e.g., erytholeukemic cells, myeloid cells or myeloblastic cells).

In some embodiments, an antibody conjugate of the invention comprises a cytotoxic agent that is non-proteinaceous. In accordance with these embodiments, the cytotoxic agent can be chemically conjugated to the antibody, either directly or through a chemical linker. In other embodiments, an antibody conjugate of the invention comprises a cytotoxic agent that is proteinaceous. In accordance with these embodiments, the cytotoxic agent can be covalently linked to the antibody through either a peptide bond or other chemical conjugation. Non-limiting examples of cytotoxic agents include diphtheria toxin, *Pseudomonas* exotoxin, ribosome inactivating proteins, ricin A, deglycosylated ricin A chain, abrin, alpha sarcin, aspergillin, restrictocin, ribonucleases, bacterial endotoxin, the lipid A moiety of bacterial endotoxin, and cholera toxin. Other examples of cytotoxic agents include, but are not limited to, peptides derived from proteins involved in apoptosis, such as Bcl-x, Bax, or Bad. In one embodiment, the cytotoxic agent is *Pseudomonas* exotoxin A or a fragment thereof. In a specific embodiment, the cytotoxic agent is a fragment of *Pseudomonas* exotoxin A that lacks the native receptor binding domain and contains the translocation and ADP-ribosylation domains of *Pseudomonas* exotoxin A. In another specific embodiment, the cytotoxic agent is a fragment of *Pseudomonas* exotoxin A that has been modified at its carboxyl terminus so that it has the amino acid sequence Lys-Asp-Glu-Leu (KDEL).

The present invention provides compositions comprising an antibody conjugate of the invention, and a carrier or excipient. In one embodiment, the present invention provides pharmaceutical compositions comprising an antibody conjugate of the invention, and a pharmaceutically acceptable carrier or excipient. In a specific embodiment, the invention provides pharmaceutical compositions comprising an antibody conjugate of the invention in an amount effective to reduce the quantity, number, amount or percentage of cancer stem cells and/or cancer cells in an animal with or animal model for myeloid leukemia or another cancer by about 25%, about 30%, 35%, about 40%, about 45%, about 50%, about 65%, about 75% or more relative to a negative control. In some embodiments, the compositions of the invention comprise an agent in addition to the antibody conjugate.

The present invention provides methods for inhibiting the proliferation or reducing the IL3Rα-expressing cell population, the methods comprising contacting a population of cells comprising IL3Rα-expressing cells with an antibody conjugate of the invention. In a specific embodiment, the present invention provides methods for inhibiting the proliferation or reducing the population of cancer stem cells expressing IL3Rα, the methods comprising contacting the IL3Rα-expressing cancer stem cell population with an antibody conjugate of the invention. In another embodiment, the present invention provides methods for inhibiting the proliferation or reducing the population of cancer cells expressing IL3Rα, the methods comprising contacting the IL3Rα-expressing cancer cell population with an antibody conjugate of the invention. In yet another embodiment, the present invention provides methods for inhibiting the proliferation or reducing the population cancer cells and cancer stem cells expressing IL3Rα, the methods comprising contacting a population of cells comprising IL3Rα-expressing cancer cells and/or IL3Rα-expressing cancer stem cells with an antibody conjugate of the invention. In some embodiments, the antibody conjugate reduces a cancer stem cell population and/or a cancer cell population by at least 25%, at least 30%, at least 40%, at least 50%, at least 65%, at least 75% or at least 85% in an animal with or animal model for myeloid leukemia or another cancer associated with IL3Rα-expressing cells relative to a negative control.

The present invention provides methods for preventing, treating and/or managing a disorder associated with IL3Rα-expressing cells (e.g., a hematologic cancer), the methods comprising administering to a subject in need thereof an antibody conjugate of the invention. In a specific embodiment, the present invention provides a method for preventing, treating and/or managing a disorder associated with IL3Rα-expressing cells (e.g., a hematologic cancer), the method comprising administering to a human subject in need thereof an effective amount of an antibody conjugate of the invention, and in some embodiments, an effective amount of another therapy. Non-limiting examples of disorders associated with IL3Rα-expressing cells include autoimmune disorders (such as lupus), inflammatory disorders (such as allergies and asthma) and cancers (such as hematologic cancers). In some embodiments, the disorder associated with IL3Rα-expressing cells is not myeloid leukemia.

The present invention provides methods for preventing relapse of cancer associated with IL3Rα-expressing cells, the methods comprising administering to a subject in need thereof an antibody conjugate of the invention. In a specific embodiment, the present invention provides methods for preventing relapse of cancer associated with IL3Rα-expressing cells, the methods comprising administering to a human subject in need thereof an effective amount of an antibody conjugate of the invention, and in some embodiments, an effective amount of another therapy. In some embodiments, the cancer associated with IL3Rα-expressing cells is not myeloid leukemia.

The present invention provides methods for preventing, treating and/or managing cancer associated with IL3Rα-expressing cells (e.g., a hematological cancer), the method comprising administering to a human subject in need thereof an antibody conjugate of the invention in an amount effective to reduce the quantity, number, amount or percentage of cancer stem cells and/or cancer cells by at least 25%, at least 30%, at least 40%, at least 50%, at least 65%, at least 75%, or at least 85% in an animal with or animal model for myeloid leukemia or another cancer associated with IL3Rα-expressing cells relative to a negative control.

The present invention provides methods for ex vivo purging of bone marrow or peripheral blood to remove cells that express IL3Rα such that the purged bone marrow or peripheral blood is suitable, e.g., for autologous stem cell transplantation to restore hematopoeitic function.

3.1 Definitions

As used herein, the terms "about" or "approximately," unless otherwise indicated, refer to a value that is no more than 10% above or below the value being modified by the term.

As used herein, the term "agent" refers to any molecule, compound, and/or substance for use in the prevention, treatment, management and/or diagnosis of a disease, including but not limited to cancer, autoimmune disease, or allergic disease. Included in this definition is the IL3Rα antibody-toxin conjugate of the invention.

As used herein, the terms "alpha subunit of the IL-3 receptor," "IL3Rα," "CD123," "IL3Rα chain" and "IL3Rα subunit" refer interchangeably to an antigenic determinant detectable on leukemia precursor cells, which immunobinds interleukin-3 (IL3). The human and murine amino acid and nucleic acid sequences can be found, e.g., in a public database such as GenBank. For example, the amino acid sequence of human IL3Rα can be found at Accession No. NP 002174 and the nucleotide sequence encoding of the human IL3Rα can be found at Accession No. NM 005191. In a specific embodiment, the IL3Rα is the human IL3Rα.

As used herein, the terms "antibody" and "antibodies" refer to molecules that contain an antigen binding site, e.g., immunoglobulins, or fragments of immunoglobulins that have the ability to bind to a particular antigen. Immunoglobulin molecules can be of any type (e.g., IgG, IgE, IgM, IgD, IgA, IgY), class (e.g., IgG1, IgG2, IgG3, IgG4, IgA1, IgA2), or subclass. Antibodies include, but are not limited to, monoclonal antibodies, polyclonal antibodies, multispecific antibodies, human antibodies, humanized antibodies, camelized antibodies, chimeric antibodies, single domain antibodies, single chain antibodies, Fab fragments, F(ab') fragments, Fv fragments, single chain Fvs (scFv), disulfide-linked Fvs (dsFv), Fd, VH, VL, anti-idiotypic (anti-Id) antibodies (including, e.g., anti-Id antibodies to antibodies of the invention), and epitope-binding fragments of any of the above. As used herein, unless specified otherwise, the term: 26292, the 32703, the 32701 or the 32716 antibody refers to the monoclonal antibody or the scFv antibody. The terms "IL3Rα antibody," IL3Rα antibodies," "antibodies of the invention," "anti-IL3Rα antibody" and "anti-IL3Rα antibodies" are used interchangeably to refer to antibodies described herein.

As used herein, the terms "antibody conjugate(s)" and "antibody fragment conjugate(s)" refer to a conjugate(s) of an antibody or antibody fragment that is prepared by way of a synthetic chemical reaction(s) or as a recombinant fusion protein(s).

As used herein, the term "amount," as used in the context of the amount of a particular cell population or cells, refers to the frequency, quantity, percentage, relative amount, or number of the particular cell population or cells.

As used herein, the term "bind" or "bind(s)" refers to any interaction, whether direct or indirect, that affects the specified receptor or receptor subunit.

As used herein, the term "cancer" refers to a neoplasm or tumor resulting from abnormal uncontrolled growth of cells. Non-limiting examples include those cancers described in Section 5.8.3, infra. The term "cancer" encompasses a disease involving both pre-malignant and malignant cancer cells. In some embodiments, cancer refers to a localized overgrowth of cells that has not spread to other parts of a subject, i.e., a benign tumor. In other embodiments, cancer refers to a malignant tumor, which has invaded and destroyed neighbouring body structures and spread to distant sites. In yet other embodiments, the cancer is associated with a specific cancer antigen.

As used herein, the term "cancer cells" refers to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

As used herein, the term "cancer stem cell(s)" refers to a cell that can be a progenitor of a highly proliferative cancer cell. A cancer stem cell has the ability to re-grow a tumor as demonstrated by its ability to form tumors in immunocompromised mice, and typically to form tumors upon subsequent serial transplantation in immunocompromised mice. Cancer stem cells are also typically slow-growing relative to the bulk of a tumor; that is, cancer stem cells are generally quiescent. In certain embodiments, but not all, the cancer stem cell may represent approximately 0.1 to 10% of a tumor.

As used herein, the term "cytotoxin" or the phrase "cytotoxic agent" refers to a compound that exhibits an adverse effect on cell growth or viability. Included in this definition are compounds that kill cells or which impair them with respect to growth, longevity, or proliferative activity.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis in the presence of tunicamycin, etc. Further, a derivative of a proteinaceous agent may contain one or more non-classical amino acids. A derivative of a proteinaceous agent possesses a similar or identical function as the proteinaceous agent from which it was derived. The term "derivative" in the context of a proteinaceous agent also refers to a proteinaceous agent that possesses a similar or identical function as a second proteinaceous agent (i.e., the proteinaceous agent from which the derivative was derived) but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy. In a specific embodiment, a derivative is a functionally active derivative.

As used herein, the phrase "detectable agents" refers to any molecule, compound and/or substance that is detectable by any methodology available to one of skill in the art. Non-limiting examples of detectable agents include dyes, gas, metals, or radioisotopes.

As used herein, the terms "disorder" and "disease" are used interchangeably to refer to a pathological condition in a subject.

As used herein, the term "effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three or more of the following results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

As used herein, the phrase "elderly human" refers to a human 65 years old or older, preferably 70 years old or older.

As used herein, the term "fragment," in the context of a proteinaceous agent (e.g., a protein or polypeptide), refers to a proteinaceous agent that is composed of a minimum of 5 amino acids, and is 8 or more amino acids, 10 or more amino acids, 15 or more amino acids, 20 or more amino acids, 25 or more amino acids, 50 or more amino acids, 75 or more amino acids, 100 or more amino acids, 150 or more amino acids, 200 or more amino acids, 300 or more amino acids, 10 to 150 amino acids, 10 to 200 amino acids, 10 to 250 amino acids, 10 to 300 amino acids, 50 to 100 amino acids, 50 to 150 amino acids, 50 to 200 amino acids, 50 to 250 amino acids, 50 to 300 amino acids, 50 to 350 amino acids, 50 to 400 amino acids, 50 to 450 amino acids, 50 to 500 amino acids, 50 to 550 amino acids, 50 to 600 amino acids, or 50 to 650 amino acids of a second proteinaceous agent.

As used herein, the term "functionally active derivative" in the context of a proteinaceous agent is a derivative of a proteinaceous agent that retains at least one, multiple, or all functions of the polypeptide or protein from which the derivative is derived. In a specific embodiment, a functionally active derivative of *Pseudomonas* exotoxin A retains the ADP-ribosylation and translocation activities that render it cytotoxic, but lacks the receptor binding function of its parent.

As used herein, the term "functionally equivalent" in the context of an IL3Rα antibody refers to an antibody that exhibits IL3Rα binding activity comparable to a reference IL3Rα antibody, as measured in an in vivo and/or in vitro assay. "Functionally equivalent" in the context of a cytotoxin refers to a compound that has cytotoxic activity comparable to that of a reference compound, as measured in an in vivo and/or in vitro assay. In a specific embodiment, two IL3Rα antibodies are functionally equivalent if they bind to an overlapping epitope on IL3Rα, as measured by a competition assay described herein.

As used herein, the term "heterologous" in the context of an entity (e.g., a fusion protein) refers to an element that is part of an entity (e.g., a fusion protein) that is composed of one or more other elements, wherein the elements are not normally found or associated together. For example, in the context of a fusion protein, two or more amino acid sequences not normally found or associated together in nature are joined, (by, e.g., conjugation).

As used herein, the phrase "human adult" refers to a human 18 years of age or older.

As used herein, the phrase "human child" refers to a human between 24 months of age and 18 years of age.

As used herein, the phrase "human infant" refers to a human less than 24 months of age, preferably less than 12 months of age, less than 6 months of age, less than 3 months of age, less than 2 months of age, or less than 1 month of age.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95%, 98%, 99% or 99.5%) identical to each other typically remain hybridized to each other. Such stringent conditions are known to those skilled in the art and can be found in Current Protocols in Molecular Biology, 1989, John Wiley & Sons, New York, Chapters 6.3.1-6.3.6. In one, non-limiting example, stringent hybridization conditions are hybridization at 6× sodium chloride/sodium citrate (SSC) at about 45° C., followed by one or more washes in 0.1×SSC, 0.2% SDS at about 68° C. In a specific, non-limiting example, stringent hybridization conditions are hybridization in 6×SSC at about 45° C., followed by one or more washes in 0.2×SSC, 0.1% SDS at 50-65° C. (i.e., one or more washes at 50° C., 55° C., 60° C., or 65° C.). It is understood that the nucleic acids of the invention do not include nucleic acid molecules that hybridize, under these conditions, solely to a nucleotide sequence consisting of only A or T nucleotides. In a specific embodiment, high-stringency conditions comprise hybridization in a buffer consisting of 6×SSC, 50 mM Tris-HCl (pH 7.5), 1 mM EDTA, 0.02% PVP, 0.02% Ficoll, 0.02% BSA, and 100 µg/ml denatured salmon sperm DNA, for 48 hours at 65° C., washing in a buffer composed of 2×SSC, 0.01% PVP, 0.01% Ficoll, and 0.01% BSA, for 45 minutes at 37° C., and washing in a buffer composed of 0.1×SSC, for 45 minutes at 50° C.

As used herein, the term "in combination" in the context of the administration of a therapy to a subject refers to the use of more than one therapy (e.g., prophylactic and/or therapeutic). The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

An "isolated" nucleic acid sequence or nucleotide sequence is one that is separated from other nucleic acid molecules that are present in a natural source of the nucleic acid sequence or nucleotide sequence. Moreover, an "isolated" nucleic acid sequence or nucleotide sequence, such as a cDNA molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

As used herein, the terms "manage," "managing," and "management" in the context of the administration of a therapy to a subject refer to the beneficial effects that a subject derives from a therapy (e.g., a prophylactic or therapeutic agent) or a combination of therapies, while not resulting in a cure of cancer. In certain embodiments, a subject is administered one or more therapies (e.g., one or more prophylactic or therapeutic agents) to "manage" cancer so as to prevent the progression or worsening of the condition.

As used herein, the term "marker" in the context of a cell or tissue (e.g. a normal or cancer cell or tumor) means any antigen, molecule or other chemical or biological entity that is specifically found in or on a tissue that it is desired to identified or identified in or on a particular tissue affected by a disease or disorder. In specific embodiments, the marker is a cell surface antigen that is differentially or preferentially expressed by specific cell types. For example, a leukemia cancer stem cell differentially expresses CD123 relative to a normal hematopoietic stem cell.

As used herein, the term "marker phenotype" in the context of a tissue (e.g., a normal or cancer cell or a tumor cell) means any combination of antigens (e.g., receptors, ligands, and other cell surface markers), molecules, or other chemical or biological entities that are specifically found in or on a tissue that it is desired to identify a particular tissue affected by a disease or disorder. In specific embodiments, the marker phenotype is a cell surface phenotype. In accordance with this embodiment, the cell surface phenotype may be determined by detecting the expression of a combination of cell surface antigens. Non-limiting examples of cell surface phenotypes of cancer stem cells of certain tumor types include $CD34^+/CD38^-$, CD123+, $CD44^+/CD24^-$, $CD133^+$, $CD34^+/CD10^-/CD19^-$, $CD138^-/CD34^-/CD19^+$, $CD133^+/RC2^+$, $CD44^+/\alpha_2\beta_1{}^{hi}/CD133^+$, CLL-1, SLAMs, and other cancer stem cell surface phenotypes mentioned herein, as well as those that are known in the art.

"Percent Identity": To determine the percent identity of amino acid sequences or their encoding nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, "Methods for assessing the statistical significance of molecular sequence features by using general scoring schemes," Proc. Natl. Acad. Sci. USA 87:2264-2268 (1990), modified as in Karlin and Altschul, "Applications and statistics for multiple high-scoring segments in molecular sequences" Proc. Natl. Acad. Sci. USA 90:5873-5877 (1993). Such an algorithm is incorporated into the BLASTN and BLASTX programs of Altschul et al., "Basic local alignment search tool," J. Mol. Biol. 215:403-410 (1990). BLAST nucleotide searches can be performed with the BLASTN nucleotide program, with parameters set, e.g., for score-100, word-size=12 to obtain nucleotide sequences homologous to nucleic acid molecules of the present invention. BLAST protein searches can be performed with the BLASTX program, with parameters set, e.g., to score-50, word-size=3 to obtain amino acid sequences homologous to a protein molecule of the present invention. To obtain gapped alignments for comparison purposes, Gapped BLAST can be utilized as described in Altschul et al., "Gapped BLAST and PSI-BLAST: a new generation of protein database search programs," Nucleic Acids Res. 25:3389-3402 (1997). Alternatively, PSI-BLAST can be used to perform an iterated search, which detects distant relationships between molecules (Id.). When utilizing BLAST, Gapped BLAST, and PSI-BLAST programs, the default parameters of the respective programs (e.g., of BLASTX and BLASTN) can be used (see, e.g., the National Center for Biotechnology Information website, http://www.ncbi.nlm.nih.gov/BLAST/). Another preferred, non-limiting example of a mathematical algorithm utilized for the comparison of sequences is the algorithm of Myers and Miller, "Optimal alignments in linear space," Comput. Appl. Biosci. 4:11-17 (1988). Such an algorithm is incorporated in the ALIGN program (version 2.0), which is part of the GCG® bioinformatics software package (Accelrys). When utilizing the ALIGN program for comparing amino acid sequences, a PAM120 weight residue table, gap length penalty of 12, and gap penalty of 4 can be used.

The "percent identity" between two sequences can be determined using techniques similar to those described above, with or without allowing gaps. In calculating percent identity, typically only exact matches are counted.

As used herein, the phrase "pharmaceutically acceptable" means approved by a regulatory agency of the federal or a state government, or listed in the United States Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a cancer or a symptom thereof in a subject resulting from the administration of a therapy (e.g., a prophylactic or therapeutic agent), or a combination of therapies (e.g., a combination of prophylactic or therapeutic agents). In some embodiments, such terms refer to one, two, three, or more results following the administration of one or more therapies: (1) a stabilization, reduction or elimination of the cancer stem cell population, (2) a stabilization, reduction or elimination in the cancer cell population, (3) an increase in response rate, (4) an increase in the length or duration of remission, (5) a decrease in the recurrence rate of cancer, (6) an increase in the time to recurrence of cancer, (7) an increase in the disease-free, relapse-free, progression-free, and/or overall survival of the patient, and (8) an amelioration of cancer-related symptoms and/or quality of life. In specific embodiments, such terms refer to a stabilization, reduction or elimination of the cancer stem cell population.

As used herein, the term "predetermined reference range" refers to a reference range for the particular biological entity, e.g., cancer stem cell, for a subject or a population of subjects. Each laboratory may establish its own reference range for each particular assay, or a standard reference range for each assay may be made available and used locally, regionally, nationally, or worldwide or may be patient-specific. In one specific embodiment, the term refers to a reference range for the amount of cancer stem cells in a patient (e.g., as determined by in vivo imaging) or a specimen from a patient. In another specific embodiment, the term refers to a reference range for the amount of cancer cells in a patient (e.g. as described by in vivo imaging) or a specimen from a patient.

As used herein, the phrase "prophylactic agent" refers to any molecule, compound, and/or substance that is used for the purpose of preventing disease, including but not limited to cancer, autoimmune disease, or allergic disease. Examples of prophylactic agents include, but are not limited to, proteinaceous (such as immunoglobulins (e.g., multi-specific Igs, single chain Igs, Ig fragments, polyclonal antibodies and their fragments, monoclonal antibodies and their fragments and binding proteins), immunotoxins, chemospecific agents, chemotoxic agents (e.g., anti-cancer agents), and small molecule drugs.

As used herein, the term "prophylactically effective regimen" refers to an effective regimen for dosing, timing, frequency and duration of the administration of one or more therapies for the prevention of cancer or a symptom thereof. In a specific embodiment, the regimen achieves one, two, or three or more of the following results: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

As used herein, the term "protocol" refers to a regimen for dosing and timing of the administration of one or more agents and/or compositions for the prevention, treatment, and/or management of a disease or a symptom thereof. In certain embodiments, the term "protocol" refers to methods of patient care that are associated with the administration of an agent.

As used herein, the terms "purified" and "isolated" in the context of a compound or agent (including, e.g., proteinaceous agents such as antibodies) that is chemically synthesized refers to a compound or agent that is substantially free of chemical precursors or other chemicals when chemically synthesized. In a specific embodiment, the compound or agent is 60%, 65%, 75%, 80%, 85%, 90%, 95%, or 99% free (by dry weight) of other, different compounds or agents.

As used herein, the terms "purified" and "isolated" when used in the context of a compound or agent (including proteinaceous agents such as antibodies) that can be obtained from a natural source, e.g., cells, refers to a compound or agent that is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound or agent that has been separated from the material (e.g., cellular components of the cells) from which it is isolated. Thus, a compound or agent that is isolated includes preparations of a compound or agent having less than about 30%, 20%, 10%, 5%, 2%, or 1% (by dry weight) of cellular materials and/or contaminating materials.

As used herein, the phrase "small molecule(s)" and analogous terms include, but are not limited to, peptides, peptidomimetics, amino acids, amino acid analogs, polynucleotides, polynucleotide analogs, nucleotides, nucleotide analogs, and other organic and inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds.

As used herein, the term "stabilizing" and analogous terms, when used in the context of a cancer stem cell population or cancer cell population, refer to the prevention of an increase in the cancer stem cell population or cancer cell population, respectively. In other words, the amount of cancer stem cells or the amount of cancer cells that a cancer is composed of is maintained, and does not increase, or increases by less than 10%, preferably less than 5%.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "therapeutic agent" refers to any molecule, compound, and/or substance that is used for the purpose of treating and/or managing cancer. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), antibody conjugates or antibody fragment conjugates, peptides (e.g., peptide receptors, selectins), binding proteins, chemospecific agents, chemotoxic agents (e.g., anti-cancer agents), radiation, chemotherapy, anti-angiogenic agents, and small molecule drugs. Therapeutic agents may be a(n) anti-angiogenesis therapy, targeted therapy, radioimmunotherapy, small molecule therapy, biologic therapy, epigenetic therapy, toxin therapy, differentiation therapy, pro-drug activating enzyme therapy, antibody therapy, chemotherapy, radiation therapy, hormonal therapy, immunotherapy, or protein therapy.

As used herein, the term "therapeutically effective regimen" refers to a regimen for dosing, timing, frequency, and duration of the administration of one or more therapies for the treatment and/or management of cancer or a symptom thereof. In a specific embodiment, the regimen achieves one, two, three, or more of the following results: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

As used herein, the terms "therapies" and "therapy" can refer to any method(s), composition(s), and/or agent(s) that can be used in the treatment of a cancer or one or more symptoms thereof. In certain embodiments, the terms "therapy" and "therapies" refer to chemotherapy, radiation therapy, radioimmunotherapy, hormonal therapy, targeted therapy, toxin therapy, pro-drug activating enzyme therapy, protein therapy, antibody therapy, small molecule therapy, epigenetic therapy, demethylation therapy, histone deacetylase inhibitor therapy, differentiation therapy, antiangiogenic therapy, biological therapy including immunotherapy and/or other therapies useful in the treatment of a cancer or one or more symptoms thereof.

As used herein, the terms "treat", "treatment", and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies. In a specific embodiment, a patient that is at a high risk for developing cancer is treated. In specific embodiments, such terms refer to one, two, or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life. In certain embodiments, such terms refer to a stabilization or reduction in the cancer stem cell population. In some embodiments, such terms refer to a stabilization or reduction in the growth of cancer cells. In some embodiments, such terms refer to a stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

As used herein the phrases "VH domain," "VH domain," "VH region" refer to the variable region of the heavy chain of an antibody which is composed of three CDRs and the framework regions. As used herein, the phrases "VL domain," "VL domain" and "VL region" refer to the variable region of the light chain of an antibody which is composed of three CDRs and the framework regions.

Concentrations, amounts, cell counts, percentages, and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

4. BRIEF DESCRIPTION OF THE FIGURES

FIGS. 1A-1D. FIG. 1A shows the DNA nucleotide sequence of the $V_H$ domain (SEQ ID NO: 1) of the 26292 monoclonal or scFv antibody. FIG. 1B shows the amino acid sequence of the $V_H$ domain (SEQ ID NO: 2) of the 26292 monoclonal or scFv antibody with the $V_H$ CDR1 (SEQ ID NO: 3), $V_H$ CDR2 (SEQ ID NO: 4), and v CDR3 (SEQ ID NO: 5) underlined, starting in order from $V_H$ CDR1 at the far left. The framework regions are the regions not underlined. FIG. 1C shows the nucleotide sequence of the $V_L$ domain (SEQ ID NO: 6) of the 26292 monoclonal scFv antibody. FIG. 1D shows the amino acid sequence of the $V_L$ domain (SEQ ID NO: 7) of the 26292 monoclonal or scFv antibody with the $V_L$ CDR1 (SEQ ID NO: 8), $V_L$ CDR2 (SEQ ID NO: 9), and VL CDR3 (SEQ ID NO: 10) underlined, starting in order from $V_L$ CDR1 at the far left. The framework regions are the regions not underlined.

FIGS. 2A-2D. FIG. 2A shows the DNA nucleotide sequence of the $V_H$ domain (SEQ ID NO: 11) of the 32703 monoclonal or scFv antibody. FIG. 2B shows the amino acid sequence of the $V_H$ domain (SEQ ID NO: 12) of the 32703 monoclonal or scFv antibody with the $V_H$ CDR1 (SEQ ID NO: 13), $V_H$ CDR2 (SEQ ID NO: 14), and $V_H$ CDR3 (SEQ ID NO: 15) underlined, starting in order from $V_H$ CDR1 at the far left. The framework regions are the regions not underlined. FIG. 2C shows the DNA nucleotide sequence of the $V_L$ domain (SEQ ID NO:16) of the 32703 monoclonal or scFv antibody. FIG. 2D shows the amino acid sequence of the $V_L$ domain (SEQ ID NO: 17) of the 32703 monoclonal or scFv antibody with the $V_L$ CDR1 (SEQ ID NO: 18), $V_L$ CDR2 (SEQ ID NO: 19), and $V_L$ CDR3 (SEQ ID NO: 20) underlined, starting in order from VL CDR1 at the far left. The framework regions are the regions not underlined.

FIGS. 3A-3D. FIG. 3A shows the DNA nucleotide sequence of the $V_H$ domain (SEQ ID NO: 21) of the 32701 monoclonal or scFv antibody. FIG. 3B shows the amino acid sequence of the $V_H$ domain (SEQ ID NO: 22) of the 32701 monoclonal or scFv antibody with the $V_H$ CDR1 (SEQ ID NO: 23), $V_H$ CDR2 (SEQ ID NO: 24), and $V_H$ CDR3 (SEQ ID NO: 25) underlined, starting in order from $V_H$ CDR1 at the far left. The framework regions are the regions not underlined. FIG. 3C shows the DNA nucleotide sequence of the $V_L$ domain (SEQ ID NO: 26) of the 32701 monoclonal or scFv antibody. FIG. 3D shows the amino acid sequence of the $V_L$ domain (SEQ ID NO: 27) of the 32701 monoclonal or scFv antibody with the $V_L$ CDR1 (SEQ ID NO: 28), $V_L$ CDR2 (SEQ ID NO: 29), and $V_L$ CDR3 (SEQ ID NO: 30) underlined, starting in order from $V_L$ CDR1 at the far left. The framework regions are the regions not underlined.

FIGS. 4A-4D. FIG. 4A shows the DNA nucleotide sequence of the VH domain (SEQ ID NO: 31) of the 32716 monoclonal or scFv antibody. FIG. 4B shows the amino acid sequence of the $V_H$ domain (SEQ ID NO: 32) of the 32716 monoclonal or scFv antibody with the $V_H$ CDR1 (SEQ ID NO: 33), $V_H$ CDR2 (SEQ ID NO: 34), and VH CDR3 (SEQ ID NO: 35) underlined, starting in order from $V_H$ CDR1 at the far left. The framework regions are the regions not underlined. FIG. 4C shows the DNA nucleotide sequence of the shows the $V_L$ domain (SEQ ID NO: 36) of the 32716 monoclonal or scFv antibody. FIG. 4D shows the amino acid sequence of the $V_L$ domain (SEQ ID NO: 37) of the 32716 monoclonal or scFv antibody with the $V_L$ CDR1 (SEQ ID NO: 38), $V_L$ CDR2 (SEQ ID NO: 39), and $V_L$ CDR3 (SEQ ID NO: 40) underlined, starting in order from $V_L$ CDR1 at the far left. The framework regions are the regions not underlined.

FIG. 5A-5B. FIG. 5A shows an alignment of the $V_H$ amino acid sequences of the 32703 monoclonal or scFv antibody (SEQ ID NO: 12), 26292 monoclonal or scFv antibody (SEQ ID NO: 2), the 32716 monoclonal or scFv antibody (SEQ ID NO: 32), the 32701 monoclonal or scFv antibody (SEQ ID NO: 22), and germline sequences (SEQ ID NO: 41). FIG. 5B shows an alignment of the $V_L$ amino acid sequences of the 32703 monoclonal or scFv antibody (SEQ ID NO: 17), 26292 monoclonal or scFv antibody (SEQ ID NO: 7), the 32716 monoclonal or scFv antibody (SEQ ID NO: 37), the 32701 monoclonal or scFv antibody (SEQ ID NO: 27), and germline sequences (SEQ ID NO: 42).

Figure 6B:
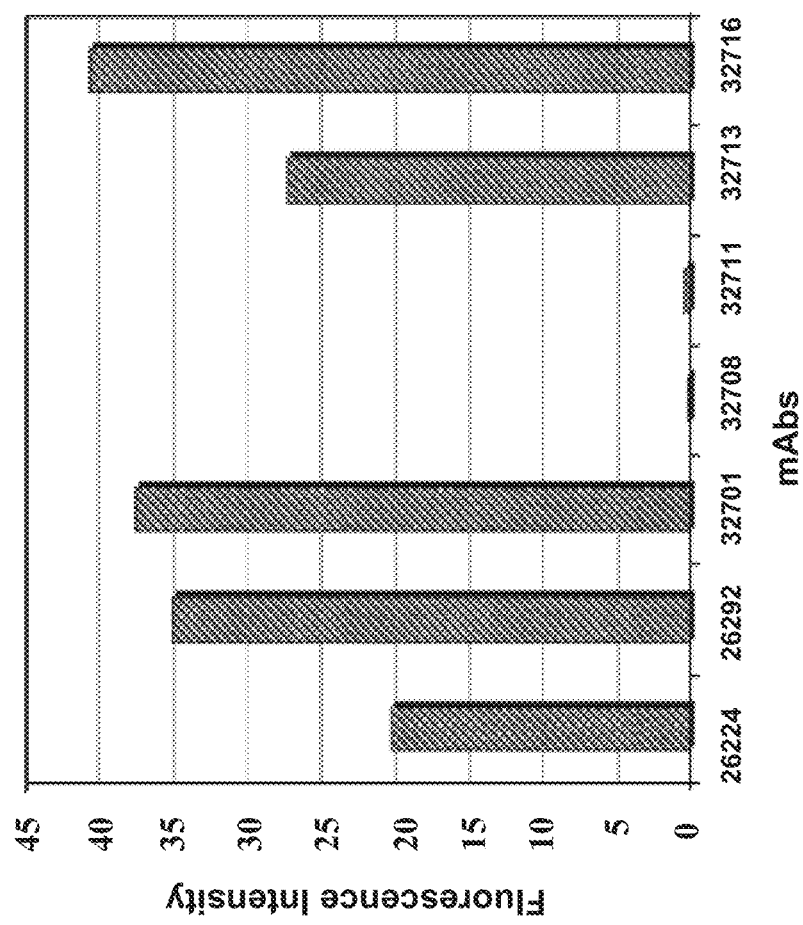

FIGS. 6A-6B. FACS analysis of binding of anti-CD123 antibodies to TF-1 and SDS-PAGE analysis of purified immunotoxins. FIG. 6A: TF-1 were stained with an isotype control MOPC-21 or anti-CD123 antibodies at 0.5 μg/ml. The fluorescence units after subtraction of the isotype control are shown. FIG. 6B: 4 μg of immunotoxin per lane. Lane "M", Precision Plus protein marker (Bio-Rad, kDa); lane "92", 26292(Fv)-PE38; lane "01", 32701(Fv)-PE38; and lane "16", 32716(Fv)-PE38.

FIGS. 7A-7D. Binding ability, cytotoxic activity and stability of anti-CD123 immunotoxins. FIG. 7A: FACS analysis of binding of 26292(Fv)-PE38, 32701(Fv)-PE38 and 32716(Fv)-PE38 to TF-1. All immunotoxins used were at 60 nM. FIG. 7B: Apparent affinity of 26292(Fv)-PE38 on TF-1. Binding saturation curve and nonlinear regression analysis were produced with Graph Pad Prism (Graph Pad Software, Inc). FIG. 7C: Cytotoxicity of 26292(Fv)-PE38, 32701(Fv)-PE38 and 32716(Fv)-PE38 on TF-1. FIG. 7D: Stability of immunotoxin 26292(Fv)-PE38. 200 ng/ml of immunotoxin was incubated at 4° C. (●) or 37° C. (■) for 1, 3 and 6 hours. The activity at time zero is set as 100%.

FIGS. 8A-8E. The expression of CD123 on leukemia cell lines TF-1 (FIG. 8A), Molm-13 (FIG. 8B), ML-1 (FIG. 8C), U937 (FIG. 8D), and Molm-14 (FIG. 8E). QuantiBRITE PE Beads were used as the PE fluorescence standard. Cell lines were stained with isotype control-PE (open region) or 9F5-PE (filled region) at 10 μg/ml.

FIGS. 9A-9E. The cytotoxicity of 26292(Fv)-PE38 (▲), 26292(Fv)-PE38-KDEL (■), and HB21(Fv)-PE40 (●) on leukemia cell lines TF-1 (FIG. 9A), Molm-13 (FIG. 9B), Molm-14 (FIG. 9C), ML-1 (FIG. 9D), and U937 (FIG. 9E).

5. DETAILED DESCRIPTION OF THE INVENTION

The present invention provides pharmaceutical compositions comprising an antibody that binds to the IL3Rα chain (preferably, the human IL3Rα chain), and a pharmaceutically acceptable carrier or excipient. In one aspect, the invention provides pharmaceutical compositions comprising an antibody that binds to the IL3Rα chain in an amount effective to reduce the quantity, number, amount or percentage of cancer stem cells and/or cancer cells in an animal with or animal model for myeloid leukemia or another cancer associated with IL3Rα-expressing cells by about 25%, about 30%, 35%, about 40%, about 45%, about 50%, about 65%, about 75% or more relative to a negative control. In a specific embodiment, the antibody incorporated into a pharmaceutical composition has a dissociation constant (Kd) of less than 4 nM on cells expressing the IL3Rα chain (e.g., erytholeukemic cells, myeloid cells or myeloblastic cells). In another embodiment, the antibody incorporated into a pharmaceutical composition comprises a variable heavy (VH) domain having the amino acid sequence of SEQ ID NO:2, 12, 22, or 32, and/or a variable light (VL) domain having the amino acid sequence of SEQ ID NO: 7, 17, 27 or 37. In another embodiment, the antibody incorporated into a pharmaceutical composition comprises one or more of the VH complementarity determining regions (CDRs) shown in FIGS. 1B, 2B, 3B and/or 4B and/or a VL domain comprising one or more of the VL CDRs shown in FIGS. 1D, 2D, 3D and/or 4D. In another embodiment, the antibody incorporated into a pharmaceutical composition competes with an antibody comprising a VH domain having the amino acid sequence of SEQ ID NO:2, 12, 22, or 32 and a VL domain having the amino acid sequence of SEQ ID NO: 7, 17, 27 or 37 for binding to IL3Rα chain. In some embodiments, a pharmaceutical composition of the invention comprises an agent in addition to an antibody of the invention.

The present invention also provides methods for inhibiting the proliferation or reducing an IL3Rα-expressing cell population, the methods comprising contacting a population of cells comprising IL3Rα-expressing cells with an antibody that binds to the IL3Rα chain. In a specific embodiment, the present invention provides methods for inhibiting the proliferation or reducing the population of cancer stem cells expressing IL3Rα, the methods comprising contacting the IL3Rα-expressing cancer stem cell population with an antibody that binds to the IL3Rα chain. In another embodiment, the present invention provides methods for inhibiting the proliferation or reducing the population of cancer cells expressing IL3Rα, the methods comprising contacting the IL3Rα-expressing cancer cell population with an antibody that binds to the IL3Rα chain. In yet another embodiment, the present invention provides methods for inhibiting the proliferation or reducing the population cancer cells and cancer stem cells expressing IL3Rα, the methods comprising contacting a population of cells comprising IL3Rα-expressing cancer cells and/or IL3Rα-expressing cancer stem cells with an antibody that binds to the IL3Rα chain. In certain embodiments, the antibody reduces the quantity, number, amount or percentage of cancer stem cells and/or cancer cells by at least 25%, at least 30%, at least 40%, at least 50%, at least 65%, at least 75%, or at least 85% in an animal with or animal model for myeloid leukemia or another cancer associated with IL3Rα-expressing cells relative to a negative control.

The present invention also provides methods for preventing, treating and/or managing a disorder associated with IL3Rα-expressing cells (e.g., a hematologic cancer), the methods comprising administering to a subject in need thereof an antibody that binds to the IL3Rα chain. In a specific embodiment, the present invention provides a method for preventing, treating and/or managing a disorder associated with IL3Rα-expressing cells (e.g., a hematologic cancer), the method comprising administering to a human subject in need thereof an effective amount of an antibody that binds to the IL3Rα chain, and in some embodiments, an effective amount of another therapy. Non-limiting examples of disorders associated with IL3Rα-expressing cells include autoimmune disorders (such as lupus), inflammatory disorders (such as allergies and asthma) and cancers (such as hematological cancers). In some embodiments, the disorder associated with IL3Rα-expressing cells is not myeloid leukemia.

The present invention provides methods for preventing relapse of cancer associated with IL3Rα-expressing cells, the methods comprising administering to a subject in need thereof an antibody that binds to the IL3Rα chain. In a specific embodiment, the present invention provides methods for preventing relapse of cancer associated with IL3Rα-expressing cells, the methods comprising administering to a human subject in need thereof an effective amount of an antibody that binds to the IL3Rα chain, and in some embodiments, an effective amount of another therapy. In some embodiments, the cancer associated with IL3Rα-expressing cells is not myeloid leukemia.

The present invention provides methods for preventing, treating and/or managing cancer associated with IL3Rα-expressing cells (e.g., a hematologic cancer), the method comprising administering to a human subject in need thereof an antibody that binds to the IL3Rα chain in an amount effective to reduce the quantity, number, amount or percentage of cancer stem cells and/or cancer cells by at least 25%, at least 30%, at least 40%, at least 50%, at least 65%, at least 75%, or at least 85% in an animal with or animal model for myeloid leukemia or another cancer associated with IL3Rα-expressing cells relative to a negative control.

The present invention provides antibody conjugates comprising an antibody that binds to the alpha chain of the IL-3 receptor alpha subunit (IL3Rα, CD123, preferably, the human IL3Rα) linked to a cytotoxic agent or other moiety, and compositions comprising such conjugates and uses of such conjugates. In one aspect, the present invention provides an antibody conjugate comprising an antibody that binds to the IL3Rα chain linked to a cytotoxic agent, wherein the immunotoxin has an $IC_{50}$ of less than 40 ng/ml on cells expressing the IL3Rα chain. In another aspect, the present invention provides an antibody conjugate comprising an antibody that binds to the IL3Rα chain linked to a cytotoxic agent, wherein the antibody comprises a VH domain having the amino acid sequence shown in FIG. 1B, 2B, 3B or 4B and/or a VL domain having the amino acid sequence shown in FIG. 1D, 2D, 3D or 4D. In another aspect, the present invention provides an antibody conjugate comprising an antibody that binds to the IL3Rα chain linked to a cytotoxic agent, wherein the antibody comprises one or more of the VH CDRs shown in FIGS. 1B, 2B, 3B and/or 4B and/or one or more of the VL CDRs shown in FIGS. 1D, 2D, 3D and/or 4D. In yet another aspect, the present invention provides an antibody conjugate comprising an antibody that binds to the IL3Rα chain linked to a cytotoxic agent, wherein the antibody competes with an antibody comprising a variable heavy (VH) domain having the amino acid sequence of SEQ ID NO:2, 12, 22, or 32, and/or a variable light (VL) domain having the amino acid sequence of SEQ ID NO: 7, 17, 27 or 37 for binding to IL3Rα chain.

The present invention provides compositions comprising an antibody conjugate of the invention, and a carrier or excipient. In a specific embodiment, the present invention provides pharmaceutical compositions comprising an antibody conjugate of the invention, and a pharmaceutically acceptable carrier or excipient. In a specific embodiment, the invention provides pharmaceutical compositions comprising an antibody conjugate of the invention in an amount effective to reduce the quantity, number, amount or percentage of cancer stem cells and/or cancer cells in an animal with or animal model for myeloid leukemia or another cancer by about 25%, about 30%, 35%, about 40%, about 45%, about 50%, about 65%, about 75% or more relative to a negative control. In some embodiments, the compositions of the invention comprise an agent in addition to the antibody conjugate.

The present invention provides methods for inhibiting the proliferation, or reducing or eradicating the IL3Rα-expressing cell population, the methods comprising contacting a population of cells comprising IL3Rα-expressing cells with an antibody conjugate of the invention. The present invention also provides methods for preventing, treating and/or managing a disorder associated with IL3Rα-expressing cells (e.g., a hematologic cancer), the methods comprising administering to a subject in need thereof an antibody conjugate of the invention. The present invention further provides methods for ex vivo purging of bone marrow or peripheral blood to remove cells that express IL3Rα such that the purged bone marrow or peripheral blood is suitable, e.g., for autologous stem cell transplantation to restore hematopoietic function.

5.1 Anti-IL3Rα Antibody Conjugates

The present invention provides antibody conjugates that bind to the IL3Rα chain (preferably, the human IL3Rα chain). In some embodiments, the antibody conjugates of the present invention comprise an antibody that binds to the IL3Rα chain expressed on the surface of cells conjugated to a cytotoxic agent or other moiety (e.g., an anticellular moiety). In some embodiments, the antibody conjugates of the present invention comprise an antibody that binds to the extracellular domain of the IL3Rα chain conjugated to a cytotoxic agent or other moiety (e.g., an anticellular moiety). In a specific embodiment, the antibody conjugate of the invention is an immunotoxin. In one embodiment, the antibody is conjugated to a cytotoxic agent or otherwise anticellular agent, either directly or through a chemical linker. In another embodiment, the antibody is linked to the cytotoxic agent or otherwise anticellular moiety through a chemical (covalent) bond, such as a peptide bond (with or without a peptide linker), disulfide bond, or sterically hindered disulfide bond. The antibody can be linked at its amino terminus or its carboxyl terminus to the cytotoxic agent or otherwise anticellular moiety. Alternatively, the antibody can replace a domain of the cytotoxic agent or otherwise anticellular moiety that is not required for cytotoxicity so long as antibody retains its specificity for the IL3Rα chain.

In certain embodiments, an antibody conjugate comprises an IL3Rα antibody linked via a peptide linker (also referred to as a spacer) to a cytotoxic agent or an otherwise anticellular moiety. The linker for the conjugate may be 5, 8, 10, 12, 15, 25, 50, or 75 amino acids in length, but the length may otherwise vary to provide optimal binding of the conjugate to IL3Rα. In a specific embodiment, the peptide linker is 6 or 7 amino acids long. In another embodiment, the amino terminus of an IL3Rα antibody is attached to a cytotoxic agent or an otherwise anticellular moiety through the peptide linker Ser-(Gly)$_4$-Ser. In another embodiment, the carboxyl terminus of an IL3Rα antibody is linked to a cytotoxic agent or an otherwise anticellular moiety through a Lys-Ala-Ser-Gly-Gly-Pro-Glu linker. The constituent amino acids of a spacer may be selected to influence some property of the conjugate, such as its folding, net charge, or hydrophobicity. Linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50 each incorporated by reference in their entireties.

An antibody conjugate of the invention may be composed of one or two polypeptide chains, together comprising the antibody moiety and the cytotoxic agent or anticellular moiety. In one embodiment, the cytotoxic agent is attached to the variable heavy ($V_H$) region of an Fv antibody fragment against IL3Rα, where the $V_H$ region is bound by an amino acid linker to the variable light ($V_L$) chain region. In another embodiment, the cytotoxic agent is attached to the $V_H$ region of an Fv antibody against IL3Rα, where the $V_H$ region is bound to a $V_L$ chain region through at least one disulfide linkage (e.g., formed between respective cysteines in each chain). Disulfide linked Fv chains may have a reduced tendency to aggregate, show a generally longer serum half-life, and are said to be "stabilized." Thus, a disulfide-stabilized antibody-cytotoxin conjugate comprises at least two polypeptides linked by at least one disulfide linkage. The two polypeptides can be separated by a termination codon and downstream initiation codon and ribosome binding site, so that the chains are encoded as separate open reading frames, or they can be joined by a peptide linker. In another embodiment, the cytotoxic agent is attached to the $V_H$ region of an Fv antibody against IL3Rα, where the $V_H$ region is bound through a peptide linker and at least one disulfide bond to a $V_L$ chain region. In a specific embodiment, the cytotoxic agent is attached to $V_L$ region of an Fv antibody against IL3Rα, where the $V_L$ region is bound by a linker to the $V_H$ chain region. In another embodiment, the cytotoxic agent is attached to the $V_L$ region of an Fv antibody against IL3Rα, where the $V_L$ region is bound through at least one disulfide bond to a $V_H$ chain region. In another embodiment, the cytotoxic agent is attached to the $V_L$ region of an Fv antibody against IL3Rα, where the $V_L$ region is bound through a peptide linker and at least one disulfide bond to a $V_H$ chain region. In yet another embodiment of the invention, the $V_L$ and $V_H$ sequences will be followed respectively by part or all of the light and heavy chain constant regions, e.g., the whole kappa light chain constant region and the $C_{H1}$ domain of the heavy chain constant region, with or without the heavy chain hinge domain. Thus, the antibody segments and genes encoding the cytotoxic agent may occur in any order on a single plasmid, or may be expressed separately from separate plasmids. For example, in another embodiment of the invention, the $V_L$ gene and any light chain constant region will be on one plasmid, while the $V_H$ gene, any heavy chain constant region, and the gene for a proteinaceous cytotoxin will be on a second plasmid. In either case, the $V_L$ and/or $V_H$ genes may be preceded by a signal sequence that directs the secretion of the recombinant fusion protein from the cell. See, e.g., U.S. Pat. Nos. 6,147,203, 6,074,644 and 6,051,405 which are referenced herein in their entirety.

In another embodiment, the polypeptide chains expressed by the plasmid may be sequestered in inclusion bodies that are retained within the cell. The polypeptides may be expressed in a variety of expression systems that are routinely available to one skilled in the art, including bacterial expression systems such as *E. coli* and yeast expression systems, such as *Pichia*. See, e.g., Vrieto et al., 2004, Protein Expression and Purification 33: 1123-133, which is incorporated herein by reference in its entirety, for methods of expressing polypeptides sequestered in inclusion bodies.

In another embodiment, this invention provides for single chain antibody conjugates, in which the antibody comprises the $V_L$ or $V_H$ regions alone, rather than as components of Fv fragments. The amino terminus or carboxyl terminus of the variable chain is then conjugated to a selected cytotoxic agent, such conjugation may be through a peptide linker. See, e.g., U.S. Pat. No. 6,074,644, which is referenced herein in its entirety.

Antibodies, or the encoded antibodies, cytotoxic agents, or antibody conjugates may be altered by being subjected to random mutagenesis by error-prone PCR, random nucleotide insertion or other methods prior to recombination. A polynucleotide encoding an IL3Rα antibody may be recombined with one or more components, motifs, sections, parts, domains, fragments, etc. of one or more cytotoxin molecules.

The invention provides nucleic acids comprising nucleotide sequences encoding an antibody conjugate of the invention. The invention also provides nucleic acids comprising a nucleotide sequence that encode the antibody moiety and/or the proteinaceous cytotoxic agent of an antibody conjugate of the invention. Thus, for example, in one embodiment, the invention provides for a nucleic acid comprising a nucleotide sequence encoding an antibody conjugate comprising a $V_H$ region of an Fv fragment attached to a proteinaceous cytotoxic agent (e.g., *Pseudomonas* exotoxin). The nucleotides that encode the $V_H$ region are linked to the nucleotides that encode the $V_L$ region through nucleotides that encode a peptide linker. Alternatively, or in combination, the encoded $V_H$ region contains cysteine residues that form disulfide linkages with a $V_L$ region of an Fv fragment. In another embodiment, the invention provides for nucleic acids comprising nucleotide sequence encoding an antibody conjugate of the invention in which the $V_L$ chain is substituted for the $V_H$ chain and vice versa. In another embodiment, the invention provides for nucleic acids comprising a nucleotide sequence encoding an antibody conjugate, in which the antibody comprises the $V_L$ or $V_H$ region alone. See, e.g., U.S. Pat. No. 6,074,644, which is referenced herein in its entirety.

In certain embodiments, an antibody conjugate of the invention competes with IL-3 for binding to the IL3Rα chain. In a specific embodiment, an antibody conjugate of the invention competes with IL-3 for binding to IL3Rα-expressing cells. In certain embodiments, an antibody conjugate prevents IL-3 receptor signal transduction.

In some embodiments, an antibody conjugate of the invention binds to an epitope on IL3Rα that results in selective and potent cell killing, as assessed by a cytotoxicity assay. In certain embodiments, binding of an antibody conjugate to its epitope on IL3Rα is followed by internalization of the antibody conjugate-IL3Rα complex. In a particular embodiment, the cytotoxicity of a particular antibody-cytotoxin conjugate is measured by a cell viability assay, using cell lines that express IL3Rα (e.g., TF-1, Molm-13, or Molm-14). In a particular embodiment, cell viability is tested using an assay in which cells are seeded into 96-well plates at a concentration of $2 \times 10^4$ of cells/well. Serial dilutions of antibody conjugates in 0.2% human serum albumin (HSA) are added to the cells, resulting in final concentrations ranging from 0.1 to 1000 ng/ml in 150 µl. After incubation for 48 hours, 10 µl of WST-8 (Dojindo Molecular Technologies) is added to each well, and the incubation is carried out for 4 hours at 37° C. The absorbance of the sample at 450 nm is measured with a reference wavelength of 650 nm. Cytotoxicity is defined by $IC_{50}$, 50% inhibition of cell viability, which is midway between the level of viability in the absence of antibody conjugate and that in the presence of 10 µg/ml cycloheximide.

The present invention also provides for panels of antibody conjugates that bind to the IL3Rα chain. In specific embodiments, the invention provides for panels of antibody conjugates having different affinities for the IL3Rα chain, different specificities for the IL3Rα chain, and/or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000 antibodies. Panels of antibody conjugates can be used, for example, in 96 well plates for assays such as ELISAs and cytotoxicity assays.

5.2 Antibodies that Bind to IL3Rα

It should be recognized that antibodies that bind to IL3Rα antigens are known in the art.

Set forth below is a more detailed description of the anti-IL3Rα antibodies encompassed within the various aspects of the invention. Such antibodies can be conjugated to cytotoxic agents or other moieties (e.g., an anticellular moiety) and used as potent and specific immunotoxins.

Alternatively, the unconjugated antibodies (i.e., naked antibodies) can be used as prophylactic and therapeutic agents.

The present invention provides methods for assessing specificity, affinity, and cytotoxicity of antibodies and antibody conjugates, such that the antibodies and antibody conjugates of the invention may be useful to specifically target and impair cells expressing IL3Rα. The present invention provides antibodies that may differentially or preferentially bind to one or more epitopes on IL3Rα. The present invention provides methods for comparing various anti-IL3Rα antibodies with respect to their differential epitope binding. The present invention provides methods for assessing the affinity of various anti-IL3Rα antibodies for their specific IL3Rα antigen on cells.

Antibodies of the invention include, but are not limited to, monoclonal antibodies, monospecific antibodies, polyclonal antibodies, multispecific antibodies, diabolizes, triabodies, tetrabodies, human antibodies, humanized antibodies, camelized antibodies, chimeric antibodies, single chain antibodies, single domain antibodies, Fab fragments, F(ab') fragments, F(ab')$_2$ fragments, Fv fragments (i.e., the smallest functional module of an antibody), single chain Fvs (scFv), disulfide-stabilized Fvs (dsFv), Fd, $V_H$, $V_L$, $V_\alpha$, $V_\beta$, and anti-idiotypic (anti-Id) antibodies (including, e.g., anti-Id antibodies to antibodies of the invention), intrabodies, and epitope-binding fragments of any of the above. In some embodiments, the antibodies are monoclonal antibodies. In other embodiments, the antibodies are Fv fragments, including $V_H$ and $V_L$ regions.

In particular, antibodies of the present invention include immunoglobulin molecules and immunologically active portions of immunoglobulin molecules, i.e., molecules that contain an antigen binding site that binds to an IL3Rα antigen. The immunoglobulin molecules of the invention can be of any type (e.g., IgG, IgE, IgM, IgD, IgA, and IgY), class (e.g., IgG$_1$, IgG$_2$, IgG$_3$, IgG$_4$, IgA$_1$, and IgA$_2$), or subclass of immunoglobulin molecule. In a specific embodiment, an antibody of the invention is an IgG antibody. In another specific embodiment, an antibody of the invention is not an IgA antibody.

The antibodies of the invention may be from any animal origin including birds and mammals (e.g., human, mouse, donkey, sheep, rabbit, goat, guinea pig, camel, horse, or chicken). Preferably, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

The antibodies of the present invention may be monospecific, bispecific, trispecific, or of greater multispecificity. Multispecific antibodies may be specific for different epitopes of an IL3Rα polypeptide or may be specific for both an IL3Rα polypeptide as well as for a heterologous epitope, such as a heterologous polypeptide or solid support material, as long as such epitopes are not found in human tissues. See, e.g., PCT publications WO 93/17715, WO 92/08802, WO 91/00360, and WO 92/05793; Tutt, et al., *J. Immunol.* 147:60-69(1991); U.S. Pat. Nos. 4,474,893, 4,714, 681, 4,925,648, 5,573,920, and 5,601,819; and Kostelny et al., *J. Immunol.* 148:1547-1553 (1992).

In one embodiment, antibodies of the invention bind to cells that express IL3Rα chain (preferably, human IL3Rα chain). In a specific embodiment, antibodies of the invention bind to a fragment of the IL3Rα chain comprising 8 to 285, 8 to 275, 8 to 250, 8 to 200, 8 to 175, 8 to 150, 8 to 100, 8 to 50, 8 to 25, 15 to 50, 15 to 75, 15 to 100 or 15 to 150 amino acids of the extracellular domain of the mature IL3Rα chain (preferably, the mature human IL3Rα chain)s. In another embodiment, the antibodies of the invention bind to the extracellular domain of the human IL3Rα chain or a fragment thereof.

An antibody of the invention may be composed of one or two polypeptide chains. In one embodiment, an Fv antibody that binds to the IL3Rα chain is composed of a single polypeptide chain, where the $V_H$ region is bound by an amino acid linker to the $V_L$ chain region. In a preferred embodiment, such scFvs are stable at 37° C. for about 2 minutes, 5 minutes, 10 minutes, 15 minutes, 20 minutes, 25 minutes, 30 minutes, 1 hour, 1.5 hours, 2 hours, 3 hours, 4 hours, 5 hours, 6 hours, 7 hours, 12 hours, 14 hours, 24 hours, 48 hours, 1 week, 2 weeks, 1 month, 3 months, 6 months, 1 year or longer as assessed by a technique known to one of skill in the art or described herein. In another embodiment, the $V_H$ region of an Fv antibody that binds to the IL3Rα chain is bound to a $V_L$ chain region through at least one disulfide linkage (e.g., formed between respective cysteines in each chain). In certain embodiments, the disulfide linked Fv chains have a reduced tendency to aggregate as measured by, e.g., HPLC and have a longer serum half-life. Thus, in a specific embodiment, a disulfide-stabilized Fv (dsFv) antibody comprises at least two polypeptides linked by at least one disulfide linkage. The two polypeptides can be separated by a termination codon and downstream initiation codon and ribosome binding site, so that the chains are encoded as separate open reading frames, or they can be additionally joined by a peptide linker. In order to provide disulfide covalent bonds between the $V_H$ and $V_L$ chains of dsFv fragments, cysteine residues are necessary. Cysteine residues can be introduced in the proper position of each $V_H$ and $V_L$, determined by alignment to reference sequences, by standard molecular biology techniques (e.g., site directed mutagenesis). See Pastan et al., U.S. Pat. No. 6,147,203, which is incorporate by reference herein in its entirety, especially columns 5-7.

In another embodiment, the $V_L$ and $V_H$ sequences will be followed respectively by part or all of the light and heavy chain constant regions, e.g., the whole kappa light chain constant region and the $C_{H1}$ domain of the heavy chain constant region, with or without the heavy chain hinge domain. Thus, the genes encoding the antibody segments may occur in any order on a single plasmid, or may be expressed separately from separate plasmids. For example, in another embodiment of the invention, the $V_L$ gene and any light chain constant region will be on one plasmid, while the $V_H$ gene and any heavy chain constant region will be on a second plasmid. In either case, the $V_L$ and/or $V_H$ genes may be preceded by a signal sequence that directs the secretion of the recombinant fusion protein from the cell. See, e.g., U.S. Pat. Nos. 6,147,203, 6,074,644, 6,051,405 which are incorporated herein by reference in their entirety.

In another embodiment, the invention provides for single chain antibodies, in which the antibody comprises the $V_L$ or $V_H$ regions alone, rather than as components of Fv fragments. See, e.g., U.S. Pat. No. 6,074,644, which is incorporated herein by reference in its entirety.

An antibody can also be conjugated to a second antibody to form an antibody heteroconjugate as described by Segal in U.S. Pat. No. 4,676,980, which is incorporated herein by reference in its entirety. In a specific embodiment, two or more antibodies are cross-linked to each to produce a bispecific or multispecific antibody.

In one embodiment, an antibody of the invention is not only found to be specific for IL3Rα but also binds with very high affinity, based on binding assays using IL3Rα-expressing cell lines. In another embodiment, an antibody of the invention is not only found to be specific for IL3Rα but also binds an epitope that overlaps with that bound by the 26292 antibody. In other embodiments, an antibody of the invention is not only found to be specific for IL3Rα but also binds an epitope that overlaps with that bound by the 32703, 32701, or 32716 antibody.

The present invention is based, in part, upon the discovery that even though a particular anti-IL3Rα antibody might bind to IL3Rα specifically and with high affinity, that does not guarantee that it will constitute an effective immunotoxin when linked to a cytotoxic agent. In one embodiment, antibodies with high affinity and specificity are chosen for conjugation to a cytotoxic agent, and they are then assessed for their ability to selectively and potently kill IL3Rα-expressing cells. In a specific embodiment, the IL3Rα antibody binds an epitope that overlaps that of an antibody known to cause specific cytotoxicity to IL3Rα-expressing cells. For example, in one embodiment, an IL3Rα antibody is tested for epitope overlap with the anti-IL3Rα antibody 26292, as assessed by the following competition assay: Cells that bear IL3Rα (e.g., TF-1, Molm-13, or Molm-14) are incubated with an excess of the 26292 antibody for 1 hour at 4° C., followed by incubation for 1 hour with an excess of the second IL3Rα antibody. If the two antibodies bind to an overlapping epitope, the amount bound by the combination will be close to that of either single antibody, whereas if the two antibodies bind to different epitopes, the signal from the combination would be close to the sum of two individual values. Bound antibody is detected with the fluorescently-labeled secondary antibody R-PE (phycoerythrin)-labeled goat F(ab')$_2$ anti-rabbit IgG (BioSource) or other appropriate specific fluorescently-labeled probe. In other embodiments, an IL3Rα antibody is tested for epitope overlap with the anti-IL3Rα antibody 32703, 32701, or 32716.

In one embodiment, an IL3Rα antibody binds to the same epitope as the 26292, 32703, 32701, or 32716 antibody as assessed by a competition assay known to one of skill in the art or described herein. In another alternative embodiment, the IL3Rα antibody does not bind to the same epitope as the 26292, 32703, 32701, or 32716 antibody, as assessed by a competition assay known to one of skill in the art or described herein.

In another embodiment of this invention, the anti-IL3Rα antibody competes with IL-3 for binding to IL3Rα or a fragment thereof (e.g., the extracellular domain of the IL3Rα or a fragment thereof). In a specific embodiment, the anti-IL3Rα antibody competes with IL-3 for binding to IL3Rα-expressing cells. In some embodiments, an antibody of the invention prevents or reduces IL3R signal transduction. In specific embodiments, an antibody of the invention binds to the IL3Rα and the antibody-IL3Rα complex is internalized.

The present invention provides antibodies that exhibit a high association rate ($k_{on}$) value in an assay known to one of skill in the art or described herein, e.g., a plasmon resonance assay. See, e.g., U.S. Application Publication No. 20020098189 (which is incorporated herein by reference in its entirety) for methods for producing and identifying antibodies with a high $k_{on}$ value. In a specific embodiment, an antibody of the present invention has an association rate constant or $k_{on}$ rate (antibody (Ab)+antigen (Ag)$^{k_{on}} \rightarrow$Ab-Ag) of at least $2 \times 10^5$ M$^{-1}$ s$^{-1}$, at least $5 \times 10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$.

The present invention that have a low dissociation rate ($k_{off}$) in an assay known to one of skill in the art or described herein, e.g., a plasmon resonance assay. In a specific embodiment, an antibody of the invention has a $k_{off}$ rate (antibody (Ab)+antigen (Ag)$^{K_{off}}\rightarrow$Ab-Ag) of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^5$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

The present invention provides antibodies that bind to the IL3Rα chain with high affinity. In a specific embodiment, an antibody of the invention has an affinity constant or $K_a$ ($k_{on}/k_{off}$) of at least $5\times10^6$ M$^{-1}$, at least $10^7$ M$^{-1}$, at least $5\times10^7$ M$^{-1}$, at least $10^8$ M$^{-1}$, at least $5\times10^{-8}$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^{15}$ M$^{-1}$. In another embodiment, the antibodies of the invention has a $K_a$ of between $5\times10^6$ M$^{-1}$ to $5\times10^{15}$ M$^{-1}$, $1\times10^7$ M$^{-1}$ to $5\times10^{12}$ M$^{-1}$, or $5\times10^7$ M$^{-1}$ to $5\times10^{10}$ M$^{-1}$.

In another embodiment, an antibody has a dissociation constant or $K_d$ ($k_{off}/k_{on}$) of less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M. In another embodiment, the antibodies of the invention have a dissociation constant ($K_d$) of less than 4000 pM, less than 3700 pM, less than 3500 pM, less than 3000 pM, less than 2750 pM, less than 2500 pM, less than 2000 pM, less than 1500 pM, less than 1000 pM, less than 750 pM, less than 500 pM, less than 250 pM, less than 200 pM, less than 150 pM, less than 100 pM, or less than 75 pM as assessed using an assay described herein or known to one of skill in the art (e.g., a BIAcore assay). In a specific embodiment, the antibodies used in accordance with the methods of the invention bind to the IL3Rα antigen and have a dissociation constant ($K_D$) of between 25 to 4000 pM, 25 to 3750 pM, 25 to 3500 pM, or 25 to 3000 pM as assessed using an assay described herein or known to one of skill in the art (e.g., a BIAcore assay).

The present invention provides antibodies that have a half-maximal inhibitory concentration (IC$_{50}$) of less than 50 ng/ml, less than 45 ng/ml, less than 40 nM, less than 35 nM, or less than 30 nM as assessed by an assay known to one of skill in the art or described herein. In a specific embodiment, the antibodies of the invention have an IC$_{50}$ of between 25 ng/ml to 75 ng/ml, 25 ng/ml to 50 ng/ml, or 25 ng/ml to 40 ng/ml.

In a specific embodiment, an antibody of the present invention is the monoclonal antibody 26292. In another embodiment, an antibody of the present invention is the scFv 26929. FIG. 1 and Table 1 provides the amino acid sequences for the V$_H$ and V$_L$ domains of the 26292 monoclonal or scFv antibody.

In one embodiment, an antibody of the present invention is the monoclonal antibody 32703. In another embodiment, an antibody of the present invention is the scFv antibody 32703. FIG. 2 and Table 1 provides the amino acid sequences for the V$_H$ and V$_L$ domains of the monoclonal or scFv antibody 32703.

In one embodiment, an antibody of the present invention is the monoclonal antibody 32701. In another embodiment, an antibody of the present invention is the scFv antibody 32701. FIG. 3 and Table 1 provide the amino acid sequences for the variable heavy (V$_H$) and variable light (V$_L$) domains of the monoclonal or scFv antibody 32701. The 32703 monoclonal antibody is available from R&D Systems, Inc.

In one embodiment, an antibody of the present invention is the monoclonal antibody 32716. In another embodiment, an antibody of the present invention is the scFv antibody 32701. FIG. 4 and Table 1 provide the amino acid sequences for the variable heavy (V$_H$) and variable light (V$_L$) domains of the monoclonal or scFv antibody 32716.

TABLE 1

Amino Acid Sequences of the 26292, 32703, 32701, and 32716 Antibodies

| | Antibody | | | |
|---|---|---|---|---|
| | 26292 | 32703 | 32701 | 32716 |
| V$_H$ domain | SEQ ID NO: 2 | SEQ ID NO: 12 | SEQ ID NO: 22 | SEQ ID NO: 32 |
| V$_H$ CDR1 | SEQ ID NO: 3 | SEQ ID NO: 13 | SEQ ID NO: 23 | SEQ ID NO: 33 |
| V$_H$ CDR1 | SEQ ID NO: 4 | SEQ ID NO: 14 | SEQ ID NO: 24 | SEQ ID NO: 34 |
| V$_H$ CDR3 | SEQ ID NO: 5 | SEQ ID NO: 15 | SEQ ID NO: 25 | SEQ ID NO: 35 |
| V$_L$ domain | SEQ ID NO: 7 | SEQ ID NO: 17 | SEQ ID NO: 27 | SEQ ID NO: 37 |
| V$_L$ CDR1 | SEQ ID NO: 8 | SEQ ID NO: 18 | SEQ ID NO: 28 | SEQ ID NO: 38 |
| V$_L$ CDR2 | SEQ ID NO: 9 | SEQ ID NO: 19 | SEQ ID NO: 29 | SEQ ID NO: 39 |
| V$_L$ CDR3 | SEQ ID NO: 10 | SEQ ID NO: 20 | SEQ ID NO: 30 | SEQ ID NO: 40 |

In a specific embodiment, the present invention provides antibodies that bind to the IL3Rα chain, said antibodies comprising a V$_H$ domain and/or V$_L$ domain having the amino acid sequence of a V$_H$ domain and/or V$_L$ domain of 26292, 32703, 32701, or 32716. In some embodiments, the antibodies comprise a human constant region known to one of skill in the art.

In one embodiment, the present invention provides antibodies that bind to the IL3Rα chain, said antibodies comprising one or more CDRs having the amino acid sequence of one or more CDRs of the monoclonal or scFv antibody 26292. In another embodiment, the present invention provides antibodies that bind to the IL3Rα chain, said antibodies comprising a combination of V$_H$ CDRs and/or V$_L$ CDRs having the amino acid sequence of V$_H$ CDRs and/or V$_L$ CDRs of the monoclonal or scFv antibody 26292.

In one embodiment, the present invention provides antibodies that bind to the IL3Rα chain, said antibodies comprising one or more CDRs having the amino acid sequence of one or more CDRs of the monoclonal or scFv antibody 32703. In another embodiment, the present invention provides antibodies that bind to the IL3Rα chain, said antibodies comprising a combination of V$_H$ CDRs and/or V$_L$ CDRs having the amino acid sequence of V$_H$ CDRs and/or V$_L$ CDRs of the monoclonal or scFv antibody 32703.

In one embodiment, the present invention provides antibodies that bind to the IL3Rα chain, said antibodies comprising one or more CDRs having the amino acid sequence of one or more CDRs of the monoclonal or scFv antibody 32701. In another embodiment, the present invention provides antibodies that bind to the IL3Rα chain, said antibodies comprising a combination of $V_H$ CDRs and/or $V_L$ CDRs having the amino acid sequence of $V_H$ CDRs and/or $V_L$ CDRs of the monoclonal or scFv antibody 32701.

In one embodiment, the present invention provides antibodies that bind to the IL3Rα chain, said antibodies comprising one or more CDRs having the amino acid sequence of one or more CDRs of the monoclonal or scFv antibody 32716. In another embodiment, the present invention provides antibodies that bind to the IL3Rα chain, said antibodies comprising a combination of $V_H$ CDRs and/or $V_L$ CDRs having the amino acid sequence of $V_H$ CDRs and/or $V_L$ CDRs of the monoclonal or scFv antibody 32716.

The present invention provides antibodies that bind to the IL3Rα chain, said antibodies comprising one or more VH CDRs and one or more VL CDRs listed in Table 1, supra. In particular, the invention provides an antibody that binds to the IL3Rα chain, said antibody comprising (or alternatively, consisting of) a VH CDR1 of the 26292, 32703, 32701 or 32719 antibody and a VL CDR1 of the 26292, 32703, 32701 or 32719 antibody; a VH CDR1 of the 26292, 32703, 32701 or 32719 antibody and a VL CDR2 of the 26292, 32703, 32701 or 32719 antibody; a VH CDR1 of the 26292, 32703, 32701 or 32719 antibody and a VL CDR3 of the 26292, 32703, 32701 or 32719 antibody; a VH CDR2 of the 26292, 32703, 32701 or 32719 antibody and a VL CDR1 of the 26292, 32703, 32701 or 32719 antibody; VH CDR2 of the 26292, 32703, 32701 or 32719 antibody and VL CDR2 of the 26292, 32703, 32701 or 32719 antibody; a VH CDR2 of the 26292, 32703, 32701 or 32719 antibody and a VL CDR3 of the 26292, 32703, 32701 or 32719 antibody; a VH CDR3 of the 26292, 32703, 32701 or 32719 antibody and a VH CDR1 of the 26292, 32703, 32701 or 32719 antibody; a VH CDR3 of the 26292, 32703, 32701 or 32719 antibody and a VL CDR2 of the 26292, 32703, 32701 or 32719 antibody; a VH CDR3 of the 26292, 32703, 32701 or 32719 antibody and a VL CDR3 of the 26292, 32703, 32701 or 32719 antibody; a VH1 CDR1, a VH CDR2 and a VL CDR1 of the 26292, 32703, 32701 or 32719 antibody; a VH CDR1, a VH CDR2 and a VL CDR2 of the 26292, 32703, 32701 or 32719 antibody; a VH CDR1, a VH CDR2 and a VL CDR3 of the 26292, 32703, 32701 or 32719 antibody; a VH CDR2, a VH CDR3 and a VL CDR1, a VH CDR2, a VH CDR3 and a VL CDR2 of the 26292, 32703, 32701 or 32719 antibody; a VH CDR2, a VH CDR2 and a VL CDR3 of the 26292, 32703, 32701 or 32719 antibody; a VH CDR1, a VL CDR1 and a VL CDR2 of the 26292, 32703, 32701 or 32719 antibody; a VH CDR1, a VL CDR1 and a VL CDR3 of the 26292, 32703, 32701 or 32719 antibody; a VH CDR2, a VL CDR1 and a VL CDR2 of the 26292, 32703, 32701 or 32719 antibody; a VH CDR2, a VL CDR1 and a VL CDR3 of the 26292, 32703, 32701 or 32719 antibody; a VH CDR3, a VL CDR1 and a VL CDR2 of the 26292, 32703, 32701 or 32719 antibody; a VH CDR3, a VL CDR1 and a VL CDR3 of the 26292, 32703, 32701 or 32719 antibody; a VH CDR1, a VH CDR2, a VH CDR3 and a VL CDR1 of the 26292, 32703, 32701 or 32719 antibody; a VH CDR1, a VH CDR2, a VH CDR3 and a VL CDR2 of the 26292, 32703, 32701 or 32719 antibody; a VH CDR1, a VH CDR2, a VH CDR3 and a VL CDR3 of the 26292, 32703, 32701 or 32719 antibody; a VH CDR1, a VH CDR2, a VL CDR1 and a VL CDR2 of the 26292, 32703, 32701 or 32719 antibody; a VH CDR1, a VH CDR2, a VL CDR1 and a VL CDR3 of the 26292, 32703, 32701 or 32719 antibody; a VH CDR2, a VH CDR3, a VL CDR1 and a VL CDR3 of the 26292, 32703, 32701 or 32719 antibody; a VH CDR2, a VH CDR3, a VL CDR2 and a VL CDR3 of the 26292, 32703, 32701 or 32719 antibody; a VH CDR1, a VH CDR2, a VH CDR3, a VL CDR1 and a VL CDR2 of the 26292, 32703, 32701 or 32719 antibody; a VH CDR1, a VH CDR2, a VH CDR3, a VL CDR1 and a VL CDR3 of the 26292, 32703, 32701 or 32719 antibody; a VH CDR1, a VH CDR2, a VL CDR1, a VL CDR2, and a VL CDR3 of the 26292, 32703, 32701 or 32719 antibody; a VH CDR1, a VH CDR3, a VL CDR1, a VL CDR2, and a VL CDR3; a VH CDR2, a VH CDR3, a VL CDR1, a VL CDR2, and a VL CDR3 of the 26292, 32703, 32701 or 32719 antibody; or any combination thereof of the VH CDRs and VL CDRs listed in Table 1, supra.

The present invention provides antibodies that bind to the IL3Rα chain, said antibodies comprising a $V_H$ domain disclosed herein combined with a $V_L$ domain disclosed herein, or other $V_L$ domain. The present invention also provides antibodies that bind to the IL3Rα chain, said antibodies comprising a $V_L$ domain disclosed herein combined with a $V_H$ domain disclosed herein, or other $V_H$ domain.

The present invention provides for nucleic acid molecules, generally isolated, comprising a nucleotide sequence(s) encoding an antibody of the invention. The nucleic acid sequences of the $V_H$ domains, the $V_L$ domains, VH CDRs and VL CDRs are provided in FIGS. 1A, 1C, 2A, 2C, 3A, 3C, 4A and 4C. The invention encompasses any nucleic acid sequence that encodes an antibody of the invention. In a specific embodiment, an isolated nucleic acid molecule(s) of the invention encodes the 26292 antibody or an antigen-binding fragment thereof. In another embodiment, an isolated nucleic acid molecule(s) of the invention encodes an antibody that binds to the IL3Rα chain, the antibody comprising a $V_H$ domain having an amino acid sequence of the $V_H$ domain of the 26292 antibody. In another embodiment, an isolated nucleic acid molecule(s) of the invention encodes an antibody that binds to the IL3Rα chain, the antibody comprising a $V_L$ domain having an amino acid sequence of the $V_L$ domain the 26292 antibody. In another embodiment, isolated nucleic acid molecules of the invention encode an antibody that binds to the IL3Rα chain, the antibody comprising a $V_H$ domain and a $V_L$ domain having an amino acid sequence of the $V_H$ domain and $V_L$ domain of the 26292 antibody.

In a another embodiment, an isolated nucleic acid molecule(s) of the invention encodes the 32703 antibody or an antigen-binding fragment thereof. In another embodiment, an isolated nucleic acid molecule(s) of the invention encodes an antibody that binds to the IL3Rα chain, the antibody comprising a $V_H$ domain having an amino acid sequence of the $V_H$ domain of the 32703 antibody. In another embodiment, an isolated nucleic acid molecule(s) of the invention encodes an antibody that binds to the IL3Rα chain, the antibody comprising a $V_L$ domain having an amino acid sequence of the $V_L$ domain the 32703 antibody. In another embodiment, isolated nucleic acid molecules of the invention encode an antibody that binds to the IL3Rα chain, the antibody comprising a $V_H$ domain and a $V_L$ domain having an amino acid sequence of the $V_H$ domain and $V_L$ domain of the 32703 antibody.

In a another embodiment, an isolated nucleic acid molecule(s) of the invention encodes the 32701 antibody or an antigen-binding fragment thereof. In another embodiment, an isolated nucleic acid molecule(s) of the invention encodes an antibody that binds to the IL3Rα chain, the antibody comprising a $V_H$ domain having an amino acid sequence of the $V_H$ domain of the 32701 antibody. In another embodiment, an isolated nucleic acid molecule(s) of the invention encodes an antibody that binds to the IL3Rα chain, the antibody comprising a $V_L$ domain having an amino acid sequence of the $V_L$ domain the 32701 antibody. In another embodiment, isolated nucleic acid molecules of the invention encode an antibody that binds to the IL3Rα chain, the antibody comprising a $V_H$ domain and a $V_L$ domain having an amino acid sequence of the $V_H$ domain and $V_L$ domain of the 32701 antibody.

In a another embodiment, an isolated nucleic acid molecule(s) of the invention encodes the 32716 antibody or an antigen-binding fragment thereof. In another embodiment, an isolated nucleic acid molecule(s) of the invention encodes an antibody that binds to the IL3Rα chain, the antibody comprising a $V_H$ domain having an amino acid sequence of the $V_H$ domain of the 32716 antibody. In another embodiment, an isolated nucleic acid molecule(s) of the invention encodes an antibody that binds to the IL3Rα chain, the antibody comprising a $V_L$ domain having an amino acid sequence of the $V_L$ domain the 32716 antibody. In another embodiment, isolated nucleic acid molecules of the invention encode an antibody that binds to the IL3Rα chain, the antibody comprising a $V_H$ domain and a $V_L$ domain having an amino acid sequence of the $V_H$ domain and $V_L$ domain of the 32716 antibody.

In another embodiment, an isolated nucleic acid molecule(s) of the invention encodes an antibody that binds to the IL3Rα chain, the antibody comprising a $V_H$ CDR1 having an amino acid sequence of the $V_H$ CDR1 of the 26292 antibody. In another embodiment, an isolated nucleic acid molecule(s) of the invention encodes an antibody that binds to the IL3Rα chain, the antibody comprising a $V_H$ CDR2 having an amino acid sequence of the $V_H$ CDR2 of the 26292 antibody. In yet another embodiment, an isolated nucleic acid molecule(s) of the invention encodes an antibody that binds to the IL3Rα chain, the antibody comprising a $V_H$ CDR3 having an amino acid sequence of the $V_H$ CDR3 of the 26292 antibody.

In another embodiment, an isolated nucleic acid molecule(s) of the invention encodes an antibody that binds to the IL3Rα chain, the antibody comprising a $V_H$ CDR1 having an amino acid sequence of the $V_H$ CDR1 of the 32703 antibody. In another embodiment, an isolated nucleic acid molecule(s) of the invention encodes an antibody that binds to the IL3Rα chain, the antibody comprising a $V_H$ CDR2 having an amino acid sequence of the $V_H$ CDR2 of the 32703 antibody. In yet another embodiment, an isolated nucleic acid molecule(s) of the invention encodes an antibody that binds to the IL3Rα chain, the antibody comprising a $V_H$ CDR3 having an amino acid sequence of the $V_H$ CDR3 of the 32703 antibody.

In another embodiment, an isolated nucleic acid molecule(s) of the invention encodes an antibody that binds to the IL3Rα chain, the antibody comprising a $V_H$ CDR1 having an amino acid sequence of the $V_H$ CDR1 of the 32701 antibody. In another embodiment, an isolated nucleic acid molecule(s) of the invention encodes an antibody that binds to the IL3Rα chain, the antibody comprising a $V_H$ CDR2 having an amino acid sequence of the $V_H$ CDR2 of the 32701 antibody. In yet another embodiment, an isolated nucleic acid molecule(s) of the invention encodes an antibody that binds to the IL3Rα chain, the antibody comprising a $V_H$ CDR3 having an amino acid sequence of the $V_H$ CDR3 of the 32701 antibody.

In another embodiment, an isolated nucleic acid molecule(s) of the invention encodes an antibody that binds to the IL3Rα chain, the antibody comprising a $V_H$ CDR1 having an amino acid sequence of the $V_H$ CDR1 of the 32716 antibody. In another embodiment, an isolated nucleic acid molecule(s) of the invention encodes an antibody that binds to the IL3Rα chain, the antibody comprising a $V_H$ CDR2 having an amino acid sequence of the $V_H$ CDR2 of the 32716 antibody. In yet another embodiment, an isolated nucleic acid molecule(s) of the invention encodes an antibody that binds to the IL3Rα chain, the antibody comprising a $V_H$ CDR3 having an amino acid sequence of the $V_H$ CDR3 of the 32716 antibody.

In another embodiment, an isolated nucleic acid molecule(s) of the present invention encodes an antibody that binds to the IL3Rα chain, the antibody comprising a $V_L$ CDR1 having an amino acid sequence of the $V_L$ CDR1 of the 26292 antibody. In another embodiment, an isolated nucleic acid molecule(s) of the present invention encodes an antibody that binds to the IL3Rα chain, the antibody comprising a $V_L$ CDR2 having an amino acid sequence of the $V_L$ CDR2 of the 26292 antibody. In yet another embodiment, an isolated nucleic acid molecule(s) of the present invention encodes an antibody that binds to the IL3Rα chain, the antibody comprising a $V_L$ CDR3 having an amino acid sequence of the $V_L$ CDR3 of the 26292 antibody.

In another embodiment, an isolated nucleic acid molecule(s) of the present invention encodes an antibody that binds to the IL3Rα chain, the antibody comprising a $V_L$ CDR1 having an amino acid sequence of the $V_L$ CDR1 of the 32703 antibody. In another embodiment, an isolated nucleic acid molecule(s) of the present invention encodes an antibody that binds to the IL3Rα chain, the antibody comprising a $V_L$ CDR2 having an amino acid sequence of the $V_L$ CDR2 of the 32703 antibody. In yet another embodiment, an isolated nucleic acid molecule(s) of the present invention encodes an antibody that binds to the IL3Rα chain, the antibody comprising a $V_L$ CDR3 having an amino acid sequence of the $V_L$ CDR3 of the 32703 antibody.

In another embodiment, an isolated nucleic acid molecule(s) of the present invention encodes an antibody that binds to the IL3Rα chain, the antibody comprising a $V_L$ CDR1 having an amino acid sequence of the $V_L$ CDR1 of the 32701 antibody. In another embodiment, an isolated nucleic acid molecule(s) of the present invention encodes an antibody that binds to the IL3Rα chain, the antibody comprising a $V_L$ CDR2 having an amino acid sequence of the $V_L$ CDR2 of the 32701 antibody. In yet another embodiment, an isolated nucleic acid molecule(s) of the present invention encodes an antibody that binds to the IL3Rα chain, the antibody comprising a $V_L$ CDR3 having an amino acid sequence of the $V_L$ CDR3 of the 32701 antibody.

In another embodiment, an isolated nucleic acid molecule(s) of the present invention encodes an antibody that binds to the IL3Rα chain, the antibody comprising a $V_L$ CDR1 having an amino acid sequence of the $V_L$ CDR1 of the 32716 antibody. In another embodiment, an isolated nucleic acid molecule(s) of the present invention encodes an antibody that binds to the IL3Rα chain, the antibody comprising a $V_L$ CDR2 having an amino acid sequence of the $V_L$ CDR2 of the 32716 antibody. In yet another embodiment, an isolated nucleic acid molecule(s) of the present invention encodes an antibody that binds to the IL3Rα chain, the antibody comprising a $V_L$ CDR3 having an amino acid sequence of the $V_L$ CDR3 of the 32716 antibody.

In another embodiment, a nucleic acid molecule(s) of the invention encodes an antibody that binds to the IL3Rα chain, the antibody comprising a VH CDR1, a VL CDR1, a VH CDR2, a VL CDR2, a VH CDR3, a VL CDR3, or any combination thereof having an amino acid sequence the 26292 antibody. In another embodiment, a nucleic acid molecule(s) of the invention encodes an antibody that binds to the IL3Rα chain, the antibody comprising a VH CDR1, a VL CDR1, a VH CDR2, a VL CDR2, a VH CDR3, a VL CDR3, or any combination thereof having an amino acid sequence the 32703 antibody. In another embodiment, a nucleic acid molecule(s) of the invention encodes an antibody that binds to the IL3Rα chain, the antibody comprising a VH CDR1, a VL CDR1, a VH CDR2, a VL CDR2, a VH CDR3, a VL CDR3, or any combination thereof having an amino acid sequence the 32701 antibody. In another embodiment, a nucleic acid molecule(s) of the invention encodes an antibody that binds to the IL3Rα chain, the antibody comprising a VH CDR1, a VL CDR1, a VH CDR2, a VL CDR2, a VH CDR3, a VL CDR3, or any combination thereof having an amino acid sequence the 32716 antibody.

In one embodiment, the invention provides for a nucleic acid comprising a nucleotide sequence encoding an antibody comprising a $V_H$ region of an Fv fragment linked to the nucleotides that encode the $V_L$ region through nucleotides that encode a peptide linker. Alternatively, or in combination, the encoded $V_H$ region contains cysteine residues that form disulfide linkages with a cysteine-containing $V_L$ region of an Fv fragment. In another embodiment, this invention provides for nucleic acids comprising nucleotide sequences encoding any of the antibodies described herein, in which the antibody comprises the $V_L$ or $V_H$ region alone. See, e.g., U.S. Pat. No. 6,074,644, which is referenced herein in its entirety.

Those skilled in the art will realize that additional modifications, deletions, insertions and the like may be made to the IL3Rα antibody. Especially, deletions or other changes may be made to the antibody in order to increase stability, affinity, specificity, or, when combined with the cytotoxic agent, cytotoxicity or other impairment to IL3Rα-expressing cells and/or to decrease non-specific cytotoxicity or impairment toward cells that lack IL3Rα antigens. Typical modifications include, but are not limited to, introduction of an upstream methionine for transcription initiation, mutation of residues to cysteine in $V_H$ or $V_L$ regions for the creation of disulfide linkages, etc. All such constructions may be made by methods of genetic engineering well known to those skilled in the art. Fragments, analogs, and derivatives of IL3Rα antibodies can be useful in the present invention provided that when fused to the cytotoxic agent portion of the conjugate, such fragments, analogs, and derivatives maintain the ability to bind native IL3Rα expressed on the surface of a cell. Preferably, the binding kinetics of the fragments, analogs, or derivatives remain the same or vary by no more than 25% (preferably, no more than 15%, 10% or 5%) as determined by an assays described herein.

To improve or alter the characteristics of IL3Rα antibodies, protein engineering may be employed. Recombinant DNA technology known to those skilled in the art can be used to create novel mutant proteins or "muteins" including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, it is known in the art that one or more amino acids may be deleted from the amino terminus or carboxyl terminus without substantial loss of biological function.

Antibodies may be altered by random mutagenesis by error-prone PCR, random nucleotide insertion or other methods prior to recombination.

The present invention also provides antibodies that bind to the IL3Rα chain, the antibodies comprising derivatives of the $V_H$ domains, $V_H$ CDRs, $V_L$ domains, and $V_L$ CDRs described herein. Standard techniques known to those of skill in the art can be used to introduce mutations in the nucleotide sequence encoding a molecule of the invention, including, for example, site directed mutagenesis and PCR mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

The present invention provides antibodies that bind to the IL3Rα chain, said antibodies comprising the amino acid sequence of the $V_H$ and/or $V_L$ domain or an antigen-binding fragment thereof of the 26292 antibody with one, two, three, four, five, six or more amino acid residue substitutions in the $V_H$ and/or $V_L$ domain or antigen-binding fragment. The present invention also provides antibodies that bind to the IL3Rα chain, said antibodies comprising the amino acid sequence of the $V_H$ and/or $V_L$ domain or an antigen-binding fragment thereof of the 26292 antibody with one, two, three, four, five, six or more amino acid residue substitutions in one or more $V_H$ CDRs and/or one or more $V_L$ CDRs. In a specific embodiment, the amino acid substitution(s) is a conservative amino acid substitution(s).

In an embodiment, an antibody that binds to the IL3Rα chain comprises the amino acid sequence of the $V_H$ and/or $V_L$ domain or an antigen-binding fragment thereof of the 32703 antibody with one, two, three, four, five, six or more amino acid residue substitutions in the $V_H$ and/or $V_L$ domain or antigen-binding fragment. The present invention also provides antibodies that bind to the IL3Rα chain, said antibodies comprising the amino acid sequence of the $V_H$ and/or $V_L$ domain or an antigen-binding fragment thereof of the 32703 antibody with one, two, three, four, five, six or more amino acid residue substitutions in one or more $V_H$ CDRs and/or one or more $V_L$ CDRs. In a specific embodiment, the amino acid substitution(s) is a conservative amino acid substitution(s).

In another embodiment, an antibody that binds to the IL3Rα chain comprises the amino acid sequence of the $V_H$ and/or $V_L$ domain or an antigen-binding fragment thereof of the 32701 antibody with one, two, three, four, five, six or more amino acid residue substitutions in the $V_H$ and/or $V_L$ domain or antigen-binding fragment. The present invention also provides antibodies that bind to the IL3Rα chain, said antibodies comprising the amino acid sequence of the $V_H$ and/or $V_L$ domain or an antigen-binding fragment thereof of the 32701 antibody with one, two, three, four, five, six or more amino acid residue substitutions in one or more $V_H$ CDRs and/or one or more $V_L$ CDRs. In a specific embodiment, the amino acid substitution(s) is a conservative amino acid substitution(s).

In another embodiment, an antibody that binds to the IL3Rα chain comprises the amino acid sequence of the $V_H$ and/or $V_L$ domain or an antigen-binding fragment thereof of the 32716 antibody with one, two, three, four, five, six or more amino acid residue substitutions in the $V_H$ and/or $V_L$ domain or antigen-binding fragment. The present invention also provides antibodies that bind to the IL3Rα chain, said antibodies comprising the amino acid sequence of the $V_H$ and/or $V_L$ domain or an antigen-binding fragment thereof of the 32716 antibody with one, two, three, four, five, six or more amino acid residue substitutions in one or more $V_H$ CDRs and/or one or more $V_L$ CDRs. In a specific embodiment, the amino acid substitution(s) is a conservative amino acid substitution(s).

The present invention also provides antibodies that bind to the IL3Rα chain, said antibodies comprising the amino acid sequence of the variable heavy domain and/or variable light domain or an antigen-binding fragment thereof of the 26292 antibody with one or more amino acid residue substitutions in one or more $V_H$ frameworks and/or one or more $V_L$ frameworks. In one embodiment, the antibody that bind to the IL3Rα chain comprises the amino acid sequence of the variable heavy domain and/or variable light domain or an antigen-binding fragment thereof of the 32703 antibody with one or more amino acid residue substitutions in one or more $V_H$ frameworks and/or one or more $V_L$ frameworks. In one embodiment, the antibody that bind to the IL3Rα chain comprises the amino acid sequence of the variable heavy domain and/or variable light domain or an antigen-binding fragment thereof of the 32701 antibody with one or more amino acid residue substitutions in one or more $V_H$ frameworks and/or one or more $V_L$ frameworks. In one embodiment, the antibody that bind to the IL3Rα chain comprises the amino acid sequence of the variable heavy domain and/or variable light domain or an antigen-binding fragment thereof of the 32716 antibody with one or more amino acid residue substitutions in one or more $V_H$ frameworks and/or one or more $V_L$ frameworks. The antibody generated by introducing substitutions in the $V_H$ domain, $V_H$ CDRs, $V_L$ domain, $V_L$ CDRs, and/or frameworks of the 26292, 32703, 32701, or 32716 antibodies can be tested in vitro and/or in vivo, for example, for its ability to bind to an IL3Rα antigen, or for its ability to, when conjugated to a cytotoxin, specifically kill or otherwise impair cells that express IL3Rα.

In a specific embodiment, an antibody that binds to the IL3Rα chain comprises an amino acid sequence encoded by a nucleotide sequence that hybridizes to the nucleotide sequence(s) encoding the 26292, 32703, 32701, or 32716 antibody or an antigen-binding fragment thereof under stringent conditions, e.g., hybridization to filter-bound DNA in 6× sodium chloride/sodium citrate (SSC) at about 45 followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions that are known to those of skill in the art (see, for example, Ausubel et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, an antibody that binds to the IL3Rα chain comprises an amino acid sequence of a $V_H$ domain and/or an amino acid sequence a $V_L$ domain encoded by a nucleotide sequence that hybridizes to the nucleotide sequence encoding the $V_H$ and/or $V_L$ domains of the 26292, 32703, 32701, or 32716 antibody under stringent conditions, e.g., hybridization to filter-bound DNA in 6×SSC at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions that are known to those of skill in the art (see, for example, Ausubel, et al., eds., 1989, Current Protocols in Molecular Biology, Vol. I, Green Publishing Associates, Inc. and John Wiley & Sons, Inc., New York at pages 6.3.1-6.3.6 and 2.10.3).

In another embodiment, an antibody that binds to the IL3Rα chain comprises an amino acid sequence of a $V_H$ CDR and/or an amino acid sequence of a $V_L$ CDRs encoded by a nucleotide sequence that hybridizes to the nucleotide sequence encoding the $V_H$ CDRs and/or $V_L$ CDRs of the 26292, 32703, 32701, or 32716 antibody under stringent conditions, e.g., hybridization to filter-bound DNA in 6×SSC at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions that are known to those of skill in the art.

In a specific embodiment, an antibody that binds to the IL3Rα chain comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the 26292, 32703, 32701 or 32716 antibody or an antigen-binding fragment thereof.

In another embodiment, an antibody that binds to the IL3Rα chain comprises an amino acid sequence of a $V_H$ domain and/or an amino acid sequence of a $V_L$ domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the $V_H$ domain and/or $V_L$ domain of the 26292, 32703, 32701 or 32716 antibody. In another embodiment, an antibody that binds to the IL3Rα chain comprises an amino acid sequence of one or more $V_H$ CDRs and/or an amino acid sequence of one or more $V_L$ CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to one or more of the $V_H$ CDRs and/or one or more of the $V_L$ CDRs of the 26292, 32703, 32701, or 32716 antibody.

The present invention also encompasses antibodies that compete with the 26292, 32703, 32701, or 32716 antibody for binding to the IL3Rα chain (preferably, human IL3Rα chain). The invention also encompasses antibodies that compete with an antibody comprising the VH domain and VL domain of the 26292, 32703, 32701 or 32716 antibody or an antibody comprising the VH CDRs and VL CDRs of the 26292, 32703, 32701 or 32716 antibody for binding to the IL3Rα chain (preferably, the human IL3Rα chain). The present invention also encompasses polypeptides, proteins, and peptides comprising $V_L$ domains and/or $V_H$ domains that compete with a $V_L$ domain and/or a $V_H$ domain of the 26292, 32703, 32701, or 32716 antibody for binding to the IL3Rα chain (preferably, the human IL3Rα chain). Further, the present invention encompasses polypeptides, proteins, and peptides comprising $V_L$ CDRs and/or $V_H$ CDRs that compete with a $V_L$ CDR and/or $V_H$ CDR of the 26292, 32703, 32701, or 32716 antibody for binding to the IL3Rα chain (preferably, the human IL3Rα chain).

The antibodies of the invention include derivatives that are modified, i.e., by the covalent attachment of any type of molecule to the antibody such that covalent attachment does not adversely affect binding to the antigen or, in the case of antibody conjugates of the invention, adversely affect its ability to bind to the IL3Rα chain and adversely affect its ability to specifically kill or impair cells that express the IL3Rα chain. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The present invention also provides antibodies that bind to the IL3Rα chain that comprise a framework region known to those of skill in the art (e.g., a human or non-human fragment). The framework region may be naturally occurring or consensus framework regions. In one embodiment, the framework region of an antibody of the invention is human (see, e.g., Clothia et al., 1998, J. Mol. Biol. 278:457-479 for a listing of human framework regions, which is incorporated by reference herein in its entirety). In a specific embodiment, an antibody of the invention comprises the framework region of the 26292, 32703, 32701, 32716 antibody.

In a specific embodiment, the present invention provides for antibodies that bind to the IL3Rα chain, said antibodies comprising the amino acid sequence of the CDRs of the 26292, 32703, 32701, or 32716 antibodies and human murine framework regions. In another embodiment, the present invention provides for antibodies that bind to the IL3Rα chain, said antibodies comprising the amino acid sequence of the CDRs of the 26292, 32703, 32701 or 32716 antibodies and human or murine framework regions with one or more amino acid substitutions at one, two, three, or more of the following residues: (a) rare framework residues that differ between the murine antibody framework (i.e., donor antibody framework) and the human antibody framework (i.e., acceptor antibody framework); (b) Venier zone residues when differing between donor antibody framework and acceptor framework; (c) interchain packing residues at the $V_H/V_L$ interface that differ between the donor antibody framework and the acceptor antibody framework; (d) canonical residues that differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the $V_H$ domain and the $V_L$ domain.

The present invention encompasses antibodies that bind to the IL3Rα chain, said antibodies comprising the amino acid sequence of the $V_H$ domain and/or $V_L$ domain of the 26292 antibody with mutations (e.g., one or more amino acid substitutions) in the framework regions. The framework regions of the $V_H$ domain of the 26292 antibody are shown in FIG. 1B as the regions not underlined. The framework regions of the $V_L$ domain of the 26292 antibody are shown in FIG. 1D as the regions not underlined. In an embodiment, an antibody that binds to the IL3Rα chain comprises the amino acid sequence of the $V_H$ domain and/or $V_L$ domain of the 32703 antibody with mutations (e.g., one or more amino acid substitutions) in the framework regions. The framework regions of the $V_H$ domain of the 32703 antibody are shown in FIG. 2B as the regions not underlined. The framework regions of the $V_L$ domain of the 32703 antibody are shown in FIG. 2D as the regions not underlined. In another embodiment, an antibody that binds to the IL3Rα chain comprises the amino acid sequence of the $V_H$ domain and/or $V_L$ domain of the 32701 antibody with mutations (e.g., one or more amino acid substitutions) in the framework regions. The framework regions of the $V_H$ domain of the 32701 antibody are shown in FIG. 3B as the regions not underlined. The framework regions of the $V_L$ domain of the 32701 antibody are shown in FIG. 3D as the regions not underlined. In another embodiment, an antibody that binds to the IL3Rα chain comprises the amino acid sequence of the $V_H$ domain and/or $V_L$ domain of the 32716 antibody with mutations (e.g., one or more amino acid substitutions) in the framework regions. The framework regions of the $V_H$ domain of the 32716 antibody are shown in FIG. 4B as the regions not underlined. The framework regions of the $V_L$ domain of the 32716 antibody are shown in FIG. 42D as the regions not underlined. In a specific embodiment, the amino acid substitutions in the framework region improve binding of the antibody to the IL3Rα chain.

In one embodiment, that binds to the IL3Rα chain, an antibody comprises the amino acid sequence of the $V_H$ and/or $V_L$ domains of the 26292 antibody with mutations (e.g., one or more amino acid residue substitutions) in the hypervariable and framework regions. In another embodiment, an antibody that binds to the IL3Rα chain comprises the amino acid sequence of the $V_H$ and/or $V_L$ domains of the 32703 antibody with mutations in the hypervariable and framework regions. In another embodiment, an antibody that binds to the IL3Rα chain comprises the amino acid sequence of the $V_H$ and/or $V_L$ domains of the 32701 antibody with mutations in the hypervariable and framework regions. In yet another embodiment, an antibody that binds to the IL3Rα chain comprises the amino acid sequence of the $V_H$ and/or $V_L$ domains of the 32716 antibody with mutations in the hypervariable and framework regions. In a specific embodiment, the amino acid substitutions in the hypervariable and framework regions improve binding of the antibody to the IL3Rα chain.

The present invention also provides antibodies of the invention that bind to the IL3Rα chain that comprise constant regions known to those of skill in the art. In one embodiment, the constant regions of an antibody of the invention are human. In another embodiment, the constant regions are derived from murine.

The present invention provides for antibodies that bind to the IL3Rα chain, the antibodies having an extended half-life in vivo and the use of such antibodies to produce an antibody conjugate of the invention. In a specific embodiment, the present invention provides antibodies that bind to the IL3Rα chain, which have a half-life in a subject, preferably a mammal and most preferably a human, of greater than about 2 minutes, 4 minutes, 5 minutes, 10 minutes, 12 minutes, 15 minutes, 20 minutes, 25 minutes, 30 minutes, 45 minutes, 1 hour, 1.5 hours, 2 hours, 3 hours, 4 hours, 5 hours, 6 hours, 7 hours, 12 hours, 14 hours, 24 hours, 48 hours, 1 week, 2 weeks, 1 month, 3 months, 6 months, 1 year 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months. In another embodiment, the present invention provides antibodies that bind to the IL3Rα chain, which have a half-life in a subject, preferably a mammal and most preferably a human, of 2 minutes, 5 minutes, 10 minutes, 15 minutes, 30 minutes, 1 hour, 1.5 hours, 2 hours, 3 hours, 4 hours, 5 hours, 6 hours, 7 hours, 12 hours, 14 hours, 24 hours, 48 hours, 1 week, 2 weeks, 1 month, 3 months, 6 months, 1 year 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antibody conjugates (e.g., monoclonal antibodies, single chain antibodies, Fv fragments, and Fab fragments) in vivo, for example, inert polymer molecules such as high molecular weight polyethylene glycol (PEG) can be attached to the antibodies with or without a multifunctional linker either through site-specific conjugation of the PEG to the amino or carboxyl terminus of the antibodies (whichever end is not conjugated to the cytotoxic agent) or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or ion-exchange chromatography. Polyethylene glycol-derivatized antibodies can be tested for binding activity as well as for in vivo efficacy using methods well-known to those of skill in the art, for example, by immunoassays described herein.

Antibodies having an increased half-life in vivo can also be generated by introducing one or more amino acid modifications (i.e., substitutions, insertions, or deletions) into an IgG constant domain, or FcRn binding fragment thereof (preferably a Fc or hinge Fc domain fragment). See, e.g., International Publication No. WO 98/23289; International Publication No. WO 97/34631; International Publication No. WO 02/060919; and U.S. Pat. No. 6,277,375, each of which is incorporated herein by reference in its entirety.

Furthermore, antibodies can be conjugated to albumin in order to make the antibody more stable in vivo or have a longer half-life in vivo. The techniques are well-known in the art; see, e.g., International Publication Nos. WO 93/15199, WO 93/15200, and WO 01/77137; and European Patent No. EP 413,622, all of which are incorporated herein by reference.

The present invention provides for panels of antibodies that bind to the IL3Rα chain. In specific embodiments, the invention provides for panels of antibodies having different affinities for the IL3Rα chain, different specificities for the IL3Rα chain, and/or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000 antibodies. Panels of antibodies can be used, for example, in 96 well plates for assays such as ELISAs and cytotoxicity assays.

5.3 Cytotoxic Agents

Any cytotoxic agent or otherwise anticellular agent known to one of skill in the art can be used to produce the antibody conjugates of the invention. A cytotoxic agent includes any agent that is detrimental to cells. Exemplary cytotoxic agents include chemotherapeutic agents, radioisotopes, cytotoxins such as cytostatic or cytocidal agents, or other anticellular agents, including known therapeutic agents.

Non-limiting examples of cytotoxic agents include antimetabolites (e.g., cytosine arabinoside, aminopterin, methotrexate, 6-mercaptopurine, 6-thioguanine, cytarabine, and 5-fluorouracil decarbazine); alkylating agents (e.g., mechlorethamine, thiotepa chlorambucil, melphalan, carmustine (BCNU) and lomustine (CCNU), cyclophosphamide, busulfan, dibromomannitol, streptozotocin, mitomycin C, cis-dichlorodiammine-platinum (II) (CDDP), and cisplatin); vinca alkaloid; anthracyclines (e.g., daunorubicin (formerly daunomycin) and doxorubicin); antibiotics (e.g., dactinomycin (formerly actinomycin), bleomycin, mithramycin, and anthramycin (AMC)); calicheamicin; CC-1065 and derivatives thereof; auristatin molecules (e.g., auristatin PHE, bryostatin-1, and dolastatin-10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); DNA-repair enzyme inhibitors (e.g., etoposide or topotecan); kinase inhibitors (e.g., compound ST1571, imatinib mesylate (Kantarjian et al., Clin Cancer Res. 8(7):2167-76 (2002)); demecolcine; and other cytotoxic agents (e.g., paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracenedione, mitoxantrone, mithramycin, actinomycin D, 1-dehydrotestosterone, glucorticoids, procaine, tetracaine, lidocaine, propranolol, and puromycin and analogs or homologues thereof and those compounds disclosed in U.S. Pat. Nos. 6,245,759, 6,399,633, 6,383,790, 6,335,156, 6,271, 242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432, 959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin, irinotecan, SN-38, topotecan, 9-aminocamptothecin, GG211 (GI147211), DX-8951f, IST-622, rubitecan, pyrazoloacridine, XR5000, saintopin, UCE6, UCE1022, TAN-1518A, TAN 1518B, KT6006, KT6528, ED-110, NB-506, ED-110, NB-506, and rebeccamycin); bulgarein; DNA minor groove binders such as Hoechst dye 33342 and Hoechst dye 33258; nitidine; fagaronine; epiberberine; coralyne; beta-lapachone; BC-4-1; antisense oligonucleotides (e.g., those disclosed in the U.S. Pat. Nos. 6,277,832, 5,998,596, 5,885,834, 5,734,033, and 5,618,709); adenosine deaminase inhibitors (e.g., fludarabine phosphate and 2-chlorodeoxyadenosine); and pharmaceutically acceptable salts, solvates, clathrates, and prodrugs thereof.

Other examples of cytotoxic agents which can be used to produce the antibody conjugates of the invention include antimitotic drugs, such as auristatin, derivatives of auristatin, monomethylauristatin, and derivatives of monomethylauristatin, such as monomethylauristatin F and monomethylauristatin E.

Other examples of cytotoxic agents which can be used to produce the antibody conjugates of the invention include maytansine (Cassady et al., 2004, Chem. Pharm. Bull. 52(1):1-26), and maytansine derivatives such as DM1 (Tassone et al., 2008, Blood 104(12): 3688-3696; Erickson et al., 2006, Cancer Res 66(8) 4426-4433) and DM4 (Erickson et al., 2006, Cancer Res 66(8) 4426-4433)

Other examples of cytotoxic agents which can be used to produce the antibody conjugates of the invention are single-walled carbon nanotubes (Gannon et al., 2007 Cancer, 110:2654-2665).

In one embodiment, the IL3Rα antibody is conjugated to a radioactive metal ion, such as the alpha-emitters $^{211}$astatine, $^{212}$bismuth, $^{213}$bismuth; the beta-emitters $^{131}$iodine, $^{90}$yttrium, $^{177}$lutetium, $^{153}$samarium, and $^{109}$palladium; or macrocyclic chelators useful for conjugating radiometal ions, including but not limited to, $^{131}$indium, $^{131}$L, $^{131}$yttrium, $^{131}$holmium, $^{131}$samarium, to polypeptides or any of those listed supra. In certain embodiments, the macrocyclic chelator is 1,4,7,10-tetraazacyclododecane-N, N',N'',N'''-tetraacetic acid (DOTA), which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

In a specific embodiment, the IL3Rα antibody is conjugated to a proteinaceous agent that modifies a given biological response and leads to cytotoxicity. In one embodiment, the IL3Rα antibody is conjugated to a plant-, fungus-, or bacteria-derived toxin. Non-limiting examples of such toxins include A chain toxins, ribosome inactivating proteins, ricin A, deglycosylated ricin A chain, abrin, alpha sarcin, aspergillin, restrictocin, ribonucleases, diphtheria toxin, bacterial endotoxin, saporin toxin, Granzyme B or the lipid A moiety of bacterial endotoxin, cholera toxin, or Pseudomonas exotoxin and derivatives and variants thereof.

Fragments, analogs, and derivatives of proteinaceous cytotoxins can be useful in the present invention provided that when fused to the IL3Rα antibody portion of the conjugate, such fragments, analogs, and derivatives allow the conjugate to bind native IL3Rα expressed on the surface of a cell. Preferably, the binding kinetics of the fragments, analogs, or derivatives remain the same or vary only by not more than 25%. The cytotoxin may be from any species. The nucleotide and/or amino acid sequences of cytotoxins can be found in the literature or public databases, or the nucleotide and/or amino acid sequences can be determined using cloning and sequencing techniques known to one of skill in the art. In some embodiments, the cytotoxin is derived from mammals. In other embodiments, the cytotoxin is derived from bacteria. In yet other embodiments, the cytotoxin is derived from fungi. In a preferred embodiment, the cytotoxin is Pseudomonas exotoxin A (PE), or an analog, derivative, or a fragment thereof.

In one embodiment of the invention, the proteinaceous cytotoxin comprises an amino acid sequence which contains at least one conservative amino acid substitution, but not more than 40 conservative amino acid substitutions, even more preferably, not more than 30 conservative amino acid substitutions, still more preferably, not more than 20 conservative amino acid substitutions, and still even more preferably, not more than 10 conservative amino acid substitutions relative to the native amino acid sequence of the chosen fragment (e.g., the native PE or diphtheria toxin amino acid sequence), which result in a silent change, i.e., no change in an activity necessary for cytotoxicity in the context of the conjugate. In another embodiment of the invention, a cytotoxin comprises an amino acid sequence that contains at least one conservative amino acid substitution in the chosen fragment; but not more than 10, 9, 8, 7, 6, 5, 4, 3, 2 or 1 conservative amino acid substitutions relative to the native amino acid sequence (e.g., the native PE or diphtheria toxin amino acid sequence), which result in a silent change. In yet another embodiment, a cytotoxic polypeptide comprises an amino acid sequence that contains one or more conservative substitutions or a combination of non-conservative and conservative amino acid substitutions relative to the native amino acid sequence of the chosen fragment, which results in a silent change.

To improve or alter the characteristics of cytotoxic polypeptides, protein engineering may be employed. Recombinant DNA technology known to those skilled in the art can be used to create novel mutant proteins or "muteins" including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, it is known in the art that one or more amino acids may be deleted from the amino terminus or carboxyl terminus without substantial loss of biological function. Exemplary cytotoxin variants suitable for forming the conjugates of the invention are found hereinbelow.

In a specific embodiment, a cytotoxic polypeptide is at least 50%, at least 65%, at least 70%, at least 75%, at least 80%, at least 85%, at least 90%, or at least 95% identical to the amino acid sequence of chosen fragment of the native cytotoxin (e.g., the native PE or diphtheria toxin amino acid sequence).

5.3.1 Pseudomonas Exotoxin and Variants Thereof

Pseudomonas exotoxin A (PE) is an extremely active 66 kDa protein (613 or 615 amino acids) secreted by

*Pseudomonas aeruginosa*. The amino acid sequence of PE can be found in the GenBank database (see, e.g., Accession No. IIKQA). It is composed of three discrete structural domains: an amino-terminal receptor binding domain (domain Ia; amino acids 1-252), a middle translocation domain (domain II; amino acids 253-364), a minor domain (domain Ib; amino acids 365-399 or 365-404), and a carboxyl-terminal ADP-ribosylating domain (domain III; amino acids 400-613/615 or 405-613/615). Upon binding its receptor on the surface of a eukaryotic cell, it is internalized by endocytosis. The toxin is then activated by proteolytic cleavage between amino acids 279 and 280, and forms a channel through which the enzymatic domain translocates to the cytosol. Once in the cytosol, PE inhibits protein synthesis, and thus exerts its cytotoxic effect, by catalyzing the irreversible ADP-ribosylation (transfer of the ADP ribosyl moiety from oxidized NAD) of translational elongation factor 2 (EF-2). See, e.g., U.S. Pat. No. 4,892,827, and Seetharam et al., "Increased Cytotoxic Activity of *Pseudomonas* Exotoxin and Two Chimeric Toxins Ending in KDEL," *J. Biol. Chem.* 266:17376-17381 (1991), which are incorporated by reference herein in their entirety.

*Pseudomonas* exotoxin-containing immunotoxins were previously constructed by first reacting native PE with iminothiolane. This reaction served both to introduce two new sulfhydryl groups used for coupling the an antibody to the toxin, and to inactivate the binding of PE to its own receptor. This approach relied on the chemical inactivation of PE-binding sites in order to minimize undesirable side effects of the immunotoxin binding to cells with PE receptors. Although this approach has been successful in killing specific cells in tissue culture and targeting tumors in mice, its therapeutic utility is limited as it cannot be administered in high doses. Therefore, catalytically-active fragments of PE are designed to overcome this limitation, facilitating the development of immunotoxins with high potency and low toxicity. For example, PE40 (*Pseudomonas* exotoxin fragment of 40 kDa is a fragment of PE that comprises the entire protein except for the receptor-binding domain (domain Ia); in immunotoxins, domain Ia can be either deleted or substituted. Moreover, additional fragments of PE have been developed, to yield cytotoxins with greater potency. These include PE37, which is a fragment that lacks domain Ia and is mutated such that it does not need to undergo proteolytic cleavage for activation (e.g., is deleted for amino acids 1-279; other mutations that result in a constitutively active fragment have been contemplated. PE35 additionally lacks part of domain Ib; other mutations in which domain Ib, in its entirety or at least the amino-terminal half of it, is deleted or substituted have been developed. PE38 is a fragment is deleted for domain Ia and amino acids 365-380 of Ib. Any combination of the modifications of PE described above, or other modifications that allow it to retain its cytotoxic activity and specificity when conjugated to an IL3Rα antibody, are contemplated. Other variants of PE that can be used in the present invention include those in which the carboxyl terminus is mutated from Arg-Glu-Asp-Leu-Lys (REDLK) to KDEL or KDEL repeats (e.g., (KDEL)$_2$ or (KDEL)$_3$). The KDEL mutation has been shown to increase the activity of immunotoxins by increasing their binding to the intracellular KDEL receptor and thereby increasing the amount of immunotoxin that reaches the cytosol. All of the above fragments of PE can be mutated so that they have the KDEL sequence at there carboxyl terminus. See, e.g., Seetharam et al., "Increased Cytotoxic Activity of *Pseudomonas* Exotoxin and Two Chimeric Toxins Ending in KDEL," *J. Biol. Chem.* 266:17376-17381 (1991) and U.S. Pat. Nos. 4,892,827, 5,696,237, 5,747,654, 5,863,745, 5,980,895, 6,051,405, 6,074,644, 6,147,203, and 6,558,672, which are incorporated by reference herein in their entirety.

Fragments, analogs, and derivatives of PE can be useful in the present application. In some embodiments, the cytotoxic moiety of the invention consists of full-length PE, i.e., the receptor binding, translocation, minor, and catalytic domains. In other embodiments, the cytotoxic moiety consists of the fragments PE35, PE37, PE38, or PE40. In preferred embodiments, the cytotoxic moiety of the invention consists of PE38.

Moreover, the antibody moiety of PE-containing immunotoxins can be substituted into different parts of PE, so that the above PE variants (including KDEL-containing variants) contain an IL3Rα antibody or fragment thereof (e.g., but not by limitation, scFv, dsFv wherein $V_H$ is in the same polypeptide as PE, or dsFv wherein $V_L$ is in the same polypeptide as PE) in place of domain Ia, in place of amino acids 1-279, or in place of all or part of domain Ib, as exemplary embodiments of the invention. In other embodiments of the invention, the antibody is inserted at the carboxyl terminus of the PE variant, wherein the native PE carboxyl-terminal amino acids 604/607-613/615 are moved to or repeated at the end of the molecule, so that the native carboxyl terminus of PE is retained (necessary for its cytotoxic activity although unrelated to its ADP ribosylation activity). In another embodiment, the antibody is inserted at the carboxyl terminus of the PE variant, wherein the native PE carboxyl-terminal amino acids 604/607-613/615 are moved to or repeated at the end of the molecule and the REDLK terminus is replaced with KDEL. An antibody or fragment thereof comprising two polypeptide chains, one of which is in the same polypeptide as the PE variant, can also be inserted at the carboxyl terminus of PE as long as one of the chains contains PE amino acids 604/607-613/615, or the REDLK-to-KDEL substitution, at its carboxyl terminus. See, e.g., Seetharam et al., "Increased Cytotoxic Activity of *Pseudomonas* Exotoxin and Two Chimeric Toxins Ending in KDEL," *J. Biol. Chem.* 266:17376-17381 (1991) and U.S. Pat. Nos. 4,892,827, 5,696,237, 5,747,654, 5,863,745, 5,980,895, 6,051,405, 6,074,644, 6,147,203, and 6,558,672, which are incorporated by reference herein in their entirety.

Other fragments, analogs, and derivatives of PE can be useful in the present invention provided that when fused to the anti-IL3Rα antibody portion of the conjugate, such fragments, analogs, and derivatives do not prevent the IL3Rα antibody from binding to IL3Rα expressed on the surface of a cell. Preferably, the binding kinetics of the fragments, analogs, or derivatives remain the same or vary only by not more than 25%. The PE polypeptide may be obtained from any species, heterologously or natively expressed. The nucleotide and/or amino acid sequences of PE polypeptides can be found in the literature or public databases, or the nucleotide and/or amino acid sequences can be determined using cloning and sequencing techniques known to one of skill in the art. In some embodiments, PE is expressed in *Escherichia coli*.

In one embodiment of the invention, a PE polypeptide comprises an amino acid sequence that contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions relative to the native amino acid sequence of the chosen fragment (e.g., the native amino acid sequence of PE38), which result in a silent change, i.e., no change in activity. In another embodiment of the invention, a PE polypeptide comprises an amino acid sequence that contains at least one conservative amino acid substitution; but not more than 10, 9, 8, 7, 6, 5, 4, 3, 2 or 1 conservative amino acid substitutions relative to the native amino acid sequence of the chosen fragment (e.g., the native PE38 amino acid sequence), which result in a silent change. In yet another embodiment, a PE polypeptide comprises an amino acid sequence that contains one or more conservative substitutions or a combination of non-conservative and conservative amino acid substitutions relative to the native amino acid sequence of the chosen fragment, which results in a silent change.

To improve or alter the characteristics of PE polypeptides, protein engineering may be employed. Recombinant DNA technology known to those skilled in the art can be used to create novel mutant proteins or "muteins" including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions.

In another embodiment, a PE polypeptide is at least 50%, at least 65%, at least 70%, at least 75%, at least 80%, at least 85%, at least 90%, or at least 95% identical to the native amino acid sequence of a chosen fragment (e.g., the native sequence of PE38).

5.4 Therapeutic Agents

Any therapeutic agent known to one of skill in the art can be used to produce the antibody conjugates of the invention. A therapeutic agent includes any agent that, when conjugated to an antibody or fragment thereof of the invention, can be used to treat cancer. In certain embodiments, a cytotoxic agent as exemplified in section 5.3 can be a therapeutic agent.

An antibody of the invention can be conjugated to therapeutic agents such as macrocyclic chelators useful for conjugating radiometal ions. In certain embodiments, the macrocyclic chelator is 1,4,7,10-tetraazacyclododecane-N,N', N'',N'''-tetraacetic acid (DOTA) which can be attached to the antibody via a linker molecule. Such linker molecules are commonly known in the art and described in Denardo, et al., 1998, Clin Cancer Res 4:2483-90; Peterson, et al., 1999, Bioconjug Chem 10:553; and Zimmerman, et al., 1999, Nucl Med Biol 26:943-50 each incorporated by reference in their entireties.

Examples of useful therapeutic radioisotopes (ordered by atomic number) include 47Sc, 67Cu, 90Y, 109Pd, 125I, 131I, 186Re, 188Re, 199 Au, 211At, 212Pb and 217Bi. These atoms can be conjugated to the peptide directly, indirectly as part of a chelate, or, in the case of iodine, indirectly as part of an iodinated Bolton-Hunter group. The radioiodine can be introduced either before or after this group is coupled to the peptide compound.

Examples of therapeutic agents which can be used to produce the antibody conjugates of the invention include, Bcl-2 family inhibitors and Bcl-2 inhibitors, including ABT-737.

Other examples of therapeutic agents which can be used to produce the antibody conjugates of the invention include nanoparticles, such as perfluorocarbon nanoparticles, (Tran et al., 2007, Int. J. Nanomedicine 2(4):515-526) and paramagnetic nanoparticles (Cyrus et al., 2008, Arterioscler Thromb Vasc Biol (on-line publication)).

An antibody or fragment thereof may be conjugated to a therapeutic agent that modifies a given biological response. Therapeutic agents are not to be construed as limited to classical chemical therapeutic agents. For example, the therapeutic agent may be a protein or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, nerve growth factor, platelet derived growth factor, tissue plasminogen activator, an apoptotic agent, e.g., TNF-α, AIM I (see, International Publication No. WO 97/33899 herein incorporated by reference in its entirety), AIM II (see, International Publication No. WO 97/34911 herein incorporated by reference in its entirety), Fas Ligand (Takahashi, et al., 1994, J Immunol, 6:1567 herein incorporated by reference in its entirety), and VEGI (see, International Publication No. WO 99/23105 herein incorporated by reference in its entirety), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Antibodies of the invention or fragments thereof can also be conjugated to Lectins. Lectins are proteins, commonly derived from plants, that bind to carbohydrates. Among other activities, some lectins are toxic. Some of the most cytotoxic substances known are protein toxins of bacterial and plant origin (Frankel et al., Ann Rev Med 37:125-142 (1986) herein incorporated by reference in its entirety). These molecules binding the cell surface and inhibit cellular protein synthesis. The most commonly used plant toxins are ricin and abrin; the most commonly used bacterial toxins are *diphtheria* toxin and *Pseudomonas* exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, et al., J Biol Chem 262: 5908-5912 (1987) herein incorporated by reference in its entirety). Other plant derived toxins, which are single chain ribosomal inhibitory proteins, include pokeweed antiviral protein, wheat germ protein, gelonin, dianthins, momorcharins, trichosanthin, and many others (Strip, et al., FEBS Lett 195:1-8 (1986) herein incorporated by reference in its entirety). *Diphtheria* toxin and *Pseudomonas* exotoxin A are also single chain proteins, and their binding and toxicity functions reside in separate domains of the same protein *Pseudomonas* exotoxin A has the same catalytic activity as *diphtheria* toxin. Ricin has been used therapeutically by binding its toxic a-chain, to targeting molecules such as Abs to enable site-specific delivery of the toxic effect. Bacterial toxins have also been used as anti-tumor conjugates. As intended herein, a toxic peptide chain or domain is conjugated to a compound of this invention and delivered in a site-specific manner to a target site where the toxic activity is desired, such as a metastatic focus.

5.5 Methods for Producing IL3Rα Antibody Conjugates

Techniques for conjugating cytotoxic agents or otherwise anticellular moieties to antibodies are well known, e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabelled Antibody In Cancer Therapy," in Monoclonal Antibodies For Cancer Detection And Therapy, Baldwin et al. (eds.), pp. 303-16 (Academic Press 1985), and Thorpe et al., 1982, Immunol. Rev. 62:119-58; each of which is incorporated herein by reference in its entirety.

Methods for fusing or conjugating proteins, polypeptides, or peptides to an antibody are known in the art, and can be used to conjugate proteinaceous cytotoxins to antibodies, or for connecting cytotoxins to antibodies through a peptide linker. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (said references are incorporated herein by reference in their entireties).

The conjugates of the present invention can be made by standard recombinant DNA techniques or by protein synthetic techniques, e.g., by use of a peptide synthesizer. For example, a nucleic acid molecule encoding a conjugate of the invention can be synthesized by conventional techniques including automated DNA synthesizers. Alternatively, PCR amplification of gene fragments can be carried out using anchor primers that give rise to complementary overhangs between two consecutive gene fragments, which can subsequently be annealed and re-amplified to generate a chimeric gene sequence (see, e.g., Current Protocols in Molecular Biology, Ausubel et al., eds., John Wiley & Sons, 1992).

The nucleotide sequences encoding a conjugate or portion thereof of the invention (anti-IL3Rα antibody and/or proteinaceous cytotoxin sequences, such as but not limited to Pseudomonas exotoxin or diphtheria toxin) may be obtained from any information available to those of skill in the art (i.e., from GenBank, the literature, or by routine cloning). The nucleotide sequence coding for a conjugate, or for the antibody or cytotoxin moiety of the conjugate, can be inserted into an appropriate expression vector, i.e., a vector that contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a conjugate, or a portion thereof, of the invention may be controlled by any promoter or enhancer element known in the art. Promoters that may be used to control expression of a conjugate or its parts include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the GAL4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region, which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region, which is active in pancreatic beta cells (Hanahan, 1985, Nature 315:115-122); immunoglobulin gene control region, which is active in lymphoid cells (Grosschedl et al., 1984, Cell 38:647-658; Adames et al., 1985, Nature 318:533-538; Alexander et al., 1987, Mol. Cell. Biol. 7:1436-1444); mouse mammary tumor virus control region, which is active in testicular, breast, lymphoid, and mast cells (Leder et al., 1986, Cell 45:485-495); albumin gene control region, which is active in liver (Pinkert et al., 1987, Genes and Devel. 1:268-276); alpha-fetoprotein gene control region, which is active in liver (Krumlauf et al., 1985, Mol. Cell. Biol. 5:1639-1648; Hammer et al., 1987, Science 235:53-58; alpha 1-antitrypsin gene control region, which is active in the liver (Kelsey et al., 1987, Genes and Devel. 1:161-171); beta-globin gene control region, which is active in myeloid cells (Mogram et al., 1985, Nature 315: 338-340; Kollias et al., 1986, Cell 46:89-94); myelin basic protein gene control region, which is active in oligodendrocyte cells in the brain (Readhead et al., 1987, Cell 48:703-712); myosin light chain-2 gene control region, which is active in skeletal muscle (Sani, 1985, Nature 314:283-286); neuronal-specific enolase (NSE), which is active in neuronal cells (Morelli et al., 1999, Gen. Virol. 80:571-83); brain-derived neurotrophic factor (BDNF) gene control region, which is active in neuronal cells (Tabuchi et al., 1998, Biochem. Biophysic. Res. Com. 253:818-823); glial fibrillary acidic protein (GFAP) promoter, which is active in astrocytes (Gomes et al., 1999, Braz J Med Biol Res 32(5):619-631; Morelli et al., 1999, Gen. Virol. 80:571-83); and gonadotropic releasing hormone gene control region, which is active in the hypothalamus (Mason et al., 1986, Science 234:1372-1378). In a specific embodiment, the expression of a conjugate of the invention is regulated by a constitutive promoter. In another embodiment, expression is regulated by an inducible promoter. In another embodiment, expression is regulated by a tissue-specific promoter.

In a specific embodiment, a vector is used that comprises a promoter operably linked to a conjugate-encoding nucleic acid (or nucleic acid that encodes a portion of the conjugate), one or more origins of replication, and, optionally, one or more selectable markers (e.g., an antibiotic resistance gene).

In mammalian host cells, a number of viral-based expression systems may be utilized. In cases where an adenovirus is used as an expression vector, polypeptide(s) of the conjugate may be ligated to an adenovirus transcription/translation control complex, e.g., the late promoter and tripartite leader sequence. This chimeric gene may then be inserted into the adenovirus genome by in vitro or in vivo recombination. Insertion into a non-essential region of the viral genome (e.g., region E1 or E3) will result in a recombinant virus that is viable and capable of expressing the antibody molecule and/or proteinaceous cytotoxic moiety in infected hosts (e.g., see Logan & Shenk, 1984, Proc. Natl. Acad. Sci. USA 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

Expression vectors containing inserts of a gene encoding a conjugate or a portion thereof can be identified by three general approaches: (a) nucleic acid hybridization; (b) presence or absence of "marker" gene functions; and (c) expression of inserted sequences. In the first approach, the presence of a gene encoding a conjugate or a portion thereof in an expression vector can be detected by nucleic acid hybridization using probes comprising sequences that are homologous to the inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a conjugate or a portion thereof into the vector. For example, if the nucleotide sequence encoding a segment(s) of a conjugate is inserted within the marker gene sequence of the vector, recombinants containing the gene encoding the conjugate insert can be identified by the absence of the marker gene function. In the third approach, recombinant expression vectors can be identified by assaying the gene product (e.g., conjugate) expressed by the recombinant. Such assays can be based, for example, on the physical or functional properties of the conjugate in in vitro assay systems, e.g., binding to IL3Rα, killing IL3Rα-expressing cells, competing with other IL3Rα antibodies or with IL-3 for binding to IL3Rα, etc.

In addition, a host cell strain may be chosen that modulates the expression of the inserted sequences, or modifies and processes the gene product in the specific fashion desired. Expression from certain promoters can be elevated in the presence of certain inducers; thus, expression of the genetically engineered conjugates or components thereof may be modulated. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in yeast will produce a glycosylated product and expression in a bacterial system will produce an unglycosylated product. Eukaryotic host cells that possess the cellular machinery for proper processing of the primary transcript, glycosylation, and phosphorylation of the gene product may be used. Such mammalian host cells include, but are not limited to, CHO, VERY, BHK, HeLa, COS, MDCK, 293, 3T3, WI38, NS0. Furthermore, different vector/host expression systems may affect processing reactions to different extents.

For long-term, high-yield production of recombinant conjugates, stable expression is preferred. For example, cell lines that stably express the conjugate or a portion thereof of the invention may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express a conjugate of the invention. Such engineered cell lines may be particularly useful in screening and evaluating compounds that affect the activity of an immunotoxin conjugate binding to IL3Rα or cytotoxin action.

A number of selection systems may be used, including but not limited to: the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

Once a conjugate or a portion thereof (i.e., the antibody, a chain of the antibody fused to a cytotoxin, the cytotoxin, etc.) of the invention has been produced by recombinant expression or by chemical synthesis, it may be purified by methods known in the art for purification and/or refolding of proteins, for example, by chromatography (e.g., ion exchange, affinity, particularly by affinity for the specific antibody for Protein A, or the antibody for IL3Rα, and sizing column chromatography), centrifugation, differential solubility, or by any other standard technique for the purification of proteins. Expression in bacteria may result in the antibody-cytotoxin conjugate being secreted into the periplasm. In such a case, proteins are purified using standard chromatographic techniques, for example, a two-step procedure that involves a Mono Q (Pharmacia LKB Biotechnology Inc.) anion exchange column and TSK-250 gel filtration column chromatography.

Often, expression in bacteria causes functional proteins, such as the IL3Rα antibody conjugates of the invention, to be localized in inclusion bodies. This requires that the proteins are solubilized using strong denaturants and subsequently refolded. In the solubilization step, a reducing agent must be present to dissolve disulfide bonds as is well known in the art. An exemplary buffer with a reducing agent is: 0.1 M Tris pH 8, 6M guanidine, 2 mM EDTA, 0.3 M DTE (dithioerythritol). Re-oxidation of protein disulfide bonds can be effectively catalyzed in the present of low molecular weight thiol reagents in reduced and oxidized form. Renaturation is typically accomplished by rapid dilution (e.g., 100 fold) of the denatured and reduced protein into refolding buffer. An exemplary buffer is 0.1 M Tris pH 8.0, 0.5M L-arginine, 8 mM oxidized glutathione, and 2 mM EDTA. Another buffer is phosphate-buffered saline. Other techniques known to those skilled in the art may be used. When the antibody moiety of the immunotoxin contains multiple chains (e.g., dsFv fragments consisting of modified $V_H$ and $V_L$, one of which is continuous with a proteinaceous cytotoxin such as PE), each chain can be solubilized separately and then combined in the refolding solution. A preferred yield is obtained when these two proteins are mixed in a molar ratio such that a molar excess of one protein over the other does not exceed a 5 fold excess. It is desirable to add excess oxidized glutathione or other oxidizing low molecular weight compounds to the refolding solution after the redox-shuffling is completed. Alternatively, the final oxidation can be omitted and the refolding carried out at pH 9.5. Renatured material can then be purified using standard chromatography techniques, for example, a three-step column chromatographic procedure involving Q-Sepharose, Mono Q, and TSK 250 gel filtration can be used to obtain highly purified monomeric fusion proteins. See, e.g., Seetharam et al., "Increased Cytotoxic Activity of *Pseudomonas* Exotoxin and Two Chimeric Toxins Ending in KDEL," *J. Biol. Chem.* 266:17376-17381 (1991) and U.S. Pat. No. 6,074,644, which are incorporated by reference herein in their entirety.

In a specific embodiment of the invention, a scFv-PE38 immunotoxin is constructed and purified. Total cellular RNA is isolated from hybridoma cells expressing the desired monoclonal antibodies using methods known to those skilled in the art, for example, using the Qiagen RNeasy mini kit. $V_H$ and $V_L$ cDNAs of the monoclonal antibodies can be obtained by a RACE method using SMART RACE cDNA amplification kit (Clontech) as described in Pastan I, Beers R, Bera T K. Recombinant immunotoxins in the treatment of cancer. Methods Mol Biol 2004; 248:503-18, or other method for preparation of cDNA known to those of skill in the art. Prepared cDNAs are then used as the template for PCR reactions to amplify the desired $V_H$ and $V_L$ fragments. The PCR products can then be cloned into an appropriate vector, either directly into a vector containing the cytotoxin, or transferred to a shuttle vector, such as pCR4®-TOPO®, using the TOPO TA cloning kit (Invitrogen). Clones for each chain should be sequenced to exclude the possibility of PCR error. The obtained sequences should be confirmed again by comparing sequences in, e.g., a public database such as GenBank. The $V_H$ and $V_L$ chains can then be assembled into a single chain Fv (scFv) and fused to PE38 as described in Pastan I, Beers R, Bera T K. Recombinant immunotoxins in the treatment of cancer. Expression and purification of scFv-PE38 is as described in Pastan I, Beers R, Bera T K. Recombinant immunotoxins in the treatment of cancer. Methods Mol Biol 2004; 248:503-18, which is incorporated herein by reference in its entirety.

In another embodiment, the PE cytotoxin can be modified so that its carboxyl terminus contains the KDEL sequence. For example, a KDEL variant can be constructed by replacing the PE38 portion from the antibody-cytotoxin conjugate expression plasmid with PE38 containing KDEL, as described in Kreitman R J, Margulies I, Stetler-Stevenson M, et al. Cytotoxic activity of disulfide-stabilized recombinant immunotoxin RFB4(dsFv)-PE38 (BL22) toward fresh malignant cells from patients with B-cell leukemias. Clin Cancer Res 2000; 6:1476-87, which is incorporated herein by reference in its entirety.

5.6 Methods for Producing Antibodies

Antibodies that bind to an antigen can be produced by any method known in the art for the synthesis of antibodies, in particular, by chemical synthesis or preferably, by recombinant expression techniques. In some embodiments, an immunogen that comprises an epitope unique to a protein component is used to generate an antibody specific for the component.

Polyclonal antibodies specific for an antigen can be produced by various procedures well-known in the art. As a non-limiting example, the antigen (i.e., human IL3Rα) can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Kohler & Milstein, 1975, Nature 256:495-497; Pasqualini & Arap, 2004, PNAS USA 101:257-259; Steinitz et al., 1977, Nature 269:420-422; Vollmers et al., 1989, Cancer Res. 49:2471-2476; Vollmers & Brandlein, 2002 Hum. Antibodies 11(4): 131-142; Harlow et al., Antibodies: A Laboratory Manual, (Cold Spring Harbor Laboratory Press, 2nd ed. 1988); Hammerling, et al., in: Monoclonal Antibodies and T Cell Hybridomas 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding IL3Rα a. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell (e.g., the hybridoma that expresses 26292, 32703, 32701 or 32716 monoclonal antibody) secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments that recognize specific particular epitopes on IL3Rα may be generated by any technique known to those of skill in the art. For example, total cellular RNA is isolated from hybridoma cells expressing the desired monoclonal antibodies using methods known to those skilled in the art, e.g., using the Qiagen RNeasy mini kit. $V_H$ and $V_L$ cDNAs of the monoclonal antibodies can be obtained by a RACE method using SMART RACE cDNA amplification kit (Clontech) as described in Pastan I, Beers R, Bera T K. Recombinant immunotoxins in the treatment of cancer. Methods Mol Biol 2004; 248:503-18, or other method for preparation of cDNA known to those of skill in the art. Prepared cDNAs are then used as the template for PCR reactions to amplify the desired $V_H$ and $V_L$ fragments. The PCR products can then be cloned into an appropriate vector, either directly into a vector containing the cytotoxin, or transferred to a shuttle vector, such as pCR4®-TOPO®, using the TOPO TA cloning kit (Invitrogen). The $V_H$ and $V_L$ chains can then be assembled into a single chain Fv (scFv) and fused to a cytotoxin as described in Pastan I, Beers R, Bera T K. "Recombinant immunotoxins in the treatment of cancer." *Methods Mol Biol* 2004; 248:503-18, which is incorporated herein by reference in its entirety. As another example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $CH_1$ domain of the heavy chain.

Further, the antibodies of the present invention can also be generated using various phage display methods known in the art. In phage display methods, functional antibody domains are displayed on the surface of phage particles that carry the polynucleotide sequences encoding them. In particular, DNA sequences encoding $V_H$ and $V_L$ domains are amplified from animal cDNA libraries (e.g., human or murine cDNA libraries of IL3Rα-expressing tissues). The DNA encoding the $V_H$ and $V_L$ domains are recombined together with an scFv linker by PCR and cloned into a phagemid vector. The vector is electroporated in *E. coli* and the *E. coli* is infected with helper phage. Phage used in these methods are typically filamentous phage including fd and M13 and the $V_H$ and $V_L$ domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International appli-cation No. PCT/GB91/01134; Griffiths et al., 1994, EMBO J 13:3245-3260; Winter et al., 1994, Annu. Rev. Immunol. 12:433-455; Liv et al., 2004, Cancer Res. 64:704-710; International publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including $V_H$ or $V_L$ nucleotide sequences, a restriction site, and a flanking sequence to protect the restriction site can be used to amplify the $V_H$ or $V_L$ sequences in scFv clones. Utilizing cloning techniques known to those of skill in the art, the PCR amplified $V_H$ domains can be cloned into vectors expressing a $V_H$ constant region, e.g., the human gamma 4 constant region, and the PCR amplified $V_L$ domains can be cloned into vectors expressing a $V_L$ constant region, e.g., human kappa or lambda constant regions. Preferably, the vectors for expressing the $V_H$ or $V_L$ domains comprise an EF-1α promoter, a secretion signal, a cloning site for the variable domain, constant domains, and a selection marker such as neomycin. The $V_H$ and $V_L$ domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice that are incapable of expressing functional endogenous immunoglobulins, but that can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg and Huszar, 1995, Int. Rev. Immunol. 13:65 93.

For a detailed discussion of methods for producing human antibodies and human monoclonal antibodies and protocols for producing such antibodies, see, e.g., Tomizuka et al., 2000 PNAS USA 97:722-727; Davis et al., 2004, Methods Mol. Biol. 248:191-200; Lagerkvist et al., 1995, Biotechniques 18:862-869; Babcook et al., 1996 PNAS USA 93:7843-7848; International publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415, which are incorporated herein by reference in their entirety.

A humanized antibody is an antibody that is capable of binding to a predetermined antigen and that comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv), in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA, and IgE, and any isotype, including IgG1, IgG2, IgG3, and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. A humanized antibody can be produced using variety of techniques known in the art, including but not limited to, CDR-grafting (see e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see e.g., European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973, each of which is incorporated herein by its entirety by reference), chain shuffling (see e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan et al., J. Immunol. 169:1119 25 (2002), Caldas et al., Protein Eng. 13(5):353 60 (2000), Morea et al., Methods 20(3):267 79 (2000), Baca et al., J. Biol. Chem. 272(16):10678 84 (1997), Roguska et al., Protein Eng. 9(10):895 904 (1996), Couto et al., Cancer Res. 55 (23 Supp):5973s-5977s (1995), Couto et al., Cancer Res. 55(8):1717 22 (1995), Sandhu J S, Gene 150(2):409 10 (1994), and Pedersen et al., J. Mol. Biol. 235(3):959 73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Diabodies, triabodies, and tetrabodies can be produced by techniques known to one of skill in the art. See, e.g., Kipriyanov, 2002, Methods Mol. Biol. 178:317-331; Todorovska et al., 2001 J. Immunol. Methods 248:47-66; and Poljak et al., 1994, Structure 2:1121-1123, each of which are incorporated herein by reference in their entirety, for methods for producing diabodies, triabodies, and tetrabodies. Single domain antibodies can also be produced by techniques known to one of skill in the art. For a description of techniques to produce single domain antibodies, see, e.g., Holliger & Hudson, 2005 Nat. Biotechnol. 23:1126-1136, Riechmann et al., 1999, J. Immunol. Methods 231:25-38; and Dick, 1990, BMJ 300:659-600, each of which is incorporated herein by reference in its entirety.

Generation of intrabodies is well-known to the skilled artisan and is described, for example, in U.S. Pat. Nos. 6,004,940; 6,072,036; 5,965,371, which are incorporated by reference in their entireties herein. Further, the construction of intrabodies is discussed in Ohage and Steipe, 1999, J. Mol. Biol. 291:1119-1128; Ohage et al., 1999, J. Mol. Biol. 291:1129-1134; and Wirtz and Steipe, 1999, Protein Science 8:2245-2250, which references are incorporated herein by reference in their entireties. Recombinant molecular biological techniques such as those described for recombinant production of antibodies may also be used in the generation of intrabodies.

5.6.1 Nucleotide Sequences Encoding an Antibody

The invention provides nucleic acid sequences comprising a nucleotide sequence encoding an antibody or an antibody conjugate that binds to IL3Rα a. In a specific embodiment, such nucleic acid sequences are isolated. The invention also encompasses nucleic acid sequences that hybridize under high, intermediate, or lower stringency hybridization conditions, e.g., as defined supra, to nucleic acid sequences that encode an antibody of the invention.

The nucleic acid sequence may be obtained, and the nucleotide sequence of the nucleic acid sequence determined, by any method known in the art. The nucleotide sequence of antibodies specific for IL3Rα or a desired epitope on IL3Rα can be obtained, e.g., from the literature or a database such as GenBank. Such a nucleic acid sequence encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR. FIGS. 1 to 4 and Table 1 provide the nucleotide and/or amino acid sequences of the VH domains, VL domains and CDRs of the 26929, 32703, 32701 and 32716 antibodies.

Alternatively, a nucleic acid sequence encoding an IL3Rα antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid—preferably poly A+ RNA—isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example, to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the nucleic acid sequence generated by the combination of the framework regions and CDRs encodes an antibody that binds to the IL3Rα chain. In a specific embodiment, one or more amino acid substitutions may be made within the framework regions, and in certain embodiments, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the nucleic acid sequence are encompassed by the present invention and within the skill of the art.

5.6.2 Recombinant Expression of an Antibody

Recombinant expression of an antibody that binds to IL3Rα described above, requires construction of an expression vector containing a nucleic acid sequence that encodes the antibody. Once a nucleic acid sequence encoding an antibody molecule, heavy or light chain of an antibody, or fragment thereof (preferably, but not necessarily, containing the heavy or light chain variable domain) of the invention has been obtained, the vector for the production of the antibody molecule may be produced by recombinant DNA technology using techniques well-known in the art. Thus, methods for preparing an antibody by expressing a nucleic acid sequence encoding the antibody are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody may be cloned into such a vector for expression of the entire heavy chain, the entire light chain, or both the entire heavy and light chains.

The expression vector is transferred to a host cell by conventional techniques and the transfected cells are then cultured by conventional techniques to produce an antibody of the invention. Thus, the invention includes host cells containing a nucleic acid sequence encoding an antibody, or a heavy or light chain thereof, or fragment thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells that may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA, or cosmid DNA expression vectors containing antibody coding sequences; yeast (e.g., *Saccharomyces cerevisiae* or *Pichia pastoris*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecules, are used for the expression of a recombinant antibody molecule. For example, mammalian cells such as Chinese hamster ovary cells (CHO), in conjunction with a vector such as the major intermediate early gene promoter element from human cytomegalovirus, is an effective expression system for antibodies (Foecking et al., 1986, Gene 45:101; and Cockett et al., 1990, Bio/Technology 8:2). In a specific embodiment, the expression of nucleotide sequences encoding antibodies that bind to the IL3R alpha chain is regulated by a constitutive promoter, inducible promoter, or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors that direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of virus-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, BT483, Hs578T, HTB2, BT2O and T47D, NS0 (a murine myeloma cell line that does not endogenously produce any immunoglobulin chains), CRL7O3O, and HsS78Bst cells.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.) and a selectable marker. Following the introduction of the foreign DNA, engineered cells may be allowed to grow for 1-2 days in an enriched media, and then are switched to selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the antibody molecule. Such engineered cell lines may be particularly useful in screening and evaluation of compositions that interact directly or indirectly with the antibody molecule.

A number of selection systems may be used; as non-limiting examples, the herpes simplex virus thymidine kinase (Wigler et al., 1977, Cell 11:223), hypoxanthine-guanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds.), Current Protocols in Human Genetics, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies may be fused to heterologous polypeptide sequences described herein or otherwise known in the art to facilitate purification.

Once a conjugate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.7 Pharmaceutical Compositions and Routes of Administration

The present invention provides compositions comprising an antibody or antibody conjugate of the invention and carrier. In one embodiment, the invention provides compositions comprising an antibody of the invention. In a another embodiment, the invention provides compositions comprising an antibody conjugate, such as an immunotoxin.

The invention provides a pharmaceutical composition comprising an effective amount of an antibody or antibody conjugate of the invention and a pharmaceutically acceptable carrier or vehicle. In a specific embodiment, a pharmaceutical composition comprises an effective amount of an antibody of the invention and a pharmaceutical acceptable carrier or vehicle. In another embodiment, a pharmaceutical composition comprises an effective amount of an antibody conjugate of the invention and a pharmaceutically acceptable carrier or vehicle. The pharmaceutical compositions are suitable for veterinary and/or human administration.

The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

The compositions of the invention can be in the form of a solid, liquid or gas (aerosol). Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow an antibody or antibody conjugate of the invention to be bioavailable upon administration of the composition to a subject. Compositions can take the form of one or more dosage units, where, for example, a tablet can be a single dosage unit, and a container of an antibody or antibody conjugate of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the antibody or antibody conjugate of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a conjugate of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the conjugates of the invention and pharmaceutically acceptable carriers are sterile. Water is a preferred carrier when the conjugate of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as EDTA; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions comprise an effective amount of an antibody or antibody conjugate of the invention such that a suitable dosage will be obtained (see infra, for suitable dosages). Typically, this amount is at least 0.01% of an antibody or antibody conjugate of the invention by weight of the composition. When intended for oral administration, this amount can be varied to be between 0.1% and 80% by weight of the composition. Preferred oral compositions can comprise from between 4% and 50% of the antibody or antibody conjugate of the invention by weight of the composition. Preferred compositions of the present invention are prepared so that a parenteral dosage unit contains from between 0.01% and 2% by weight of the antibody or antibody conjugate of the invention.

The compositions of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering an antibody or antibody conjugate of the invention. In certain embodiments, more than one antibody or antibody conjugate of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a precancerous condition).

In one embodiment, the antibodies or antibody conjugates of the invention are administered parenterally. In a specific embodiment, the antibodies or antibody conjugates of the invention are administered intravenously. In another embodiment, the antibodies or antibody conjugates of the invention are administered by continuous infusion. In a particular embodiment, the antibodies or antibody conjugates of the invention are administered by an infusion that lasts for about 15 minutes, about 20 minutes, about 30 minutes, about 45 minutes, about 1 hour, or about 2 hours.

In specific embodiments, it can be desirable to administer one or more antibodies or antibody conjugates of the invention locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as silastic membranes, or fibers. In one embodiment, administration can be by direct injection at the site (or former site) of a cancer, tumor, or precancerous tissue. In certain embodiments, it can be desirable to introduce one or more antibodies or antibody conjugates of the invention into the central nervous system by any suitable route, including intraventricular and intrathecal injection. Intraventricular injection can be facilitated by an intraventricular catheter, for example, attached to a reservoir, such as an Ommaya reservoir. In certain embodiments, one or more compounds of the invention can be injected intraperitoneally.

Pulmonary administration can also be employed, e.g., by use of an inhaler or nebulizer, and formulation with an aerosolizing agent, or via perfusion in a fluorocarbon or synthetic pulmonary surfactant. In certain embodiments, the antibodies or antibody conjugates of the invention can be formulated as a suppository, with traditional binders and carriers such as triglycerides.

In yet another embodiment, the antibody or antibody conjugates of the invention can be delivered in a controlled release system. In one embodiment, a pump can be used (see Sefton, *CRC Crit. Ref Biomed. Eng.* 1987, 14, 201; Buchwald et al., Surgery 1980, 88: 507; Saudek et al., *N. Engl. J. Med.* 1989, 321: 574). In another embodiment, polymeric materials can be used (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., Science 1985, 228, 190; During et al., *Ann. Neurol.*, 1989, 25, 351; Howard et al., *J. Neurosurg.*, 1989, 71, 105). In yet another embodiment, a controlled-release system can be placed in proximity of the target of the antibodies or antibody conjugates of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can be used.

In another embodiment, polymeric materials can be used to achieve controlled or sustained release of the antibodies or antibody conjugates of the invention (see, e.g., U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in *Remington's Pharmaceutical Sciences* by E. W. Martin.

Sustained or directed release compositions that can be formulated include, but are not limited to, antibodies or antibody conjugates of the invention protected with differentially degradable coatings, e.g., by microencapsulation, multiple coatings, etc. It is also possible to freeze-dry the compositions and use the lyophilizates obtained, for example, for the preparation of products for injection.

In a preferred embodiment, the antibodies or antibody conjugates of the invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetics such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where an antibody or antibody conjugate of the invention is to be administered by infusion, it can be dispensed, for example, with an infusion bottle containing sterile pharmaceutical grade water or saline. Where the antibody or antibody conjugate of the invention is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving complex are also suitable for orally administered compositions of the invention. In these later platforms, fluid from the environment surrounding the capsule is imbibed by the driving complex, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard carriers such as mannitol, lactose, starch, magnesium stearate, sodium saccharine, cellulose, magnesium carbonate, etc. Such carriers are preferably of pharmaceutical grade.

The pharmaceutical compositions of the invention can be intended for topical administration, in which case the carrier can be in the form of a solution, emulsion, ointment or gel base. The base, for example, can comprise one or more of the following: petrolatum, lanolin, polyethylene glycols, beeswax, mineral oil, diluents such as water and alcohol, and emulsifiers and stabilizers. Thickening agents can be present in a composition for topical administration. If intended for transdermal administration, the composition can be in the form of a transdermal patch or an iontophoresis device.

Topical formulations can comprise a concentration of a conjugate of the invention of from between 0.01% and 10% w/v (weight per unit volume of composition).

The compositions can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients. Aerosols of the compositions can be delivered in single phase, bi-phasic, or tri-phasic systems in order to deliver the composition. Delivery of the aerosol includes the necessary container, activators, valves, subcontainers, spacers and the like, which together can form a kit. Preferred aerosols can be determined by one skilled in the art, without undue experimentation.

Whether in solid, liquid or gaseous form, the compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance in a particular embodiment, the pharmaceutical composition comprises a conjugate of the invention, an additional agent, and a pharmaceutically acceptable carrier or vehicle.

The pharmaceutical compositions can be prepared using methodology well known in the pharmaceutical art. For example, a composition intended to be administered by injection can be prepared by combining a conjugate of the invention with water so as to form a solution. A surfactant can be added to facilitate the formation of a homogeneous solution or suspension. Surfactants are complexes that can non-covalently interact with a conjugate of the invention so as to facilitate dissolution or homogeneous suspension of the conjugate of the invention in the aqueous delivery system.

In one embodiment, the pharmaceutical compositions of the present invention may comprise one or more other therapies.

The present invention provides pharmaceutical compositions comprising an antibody of the invention in an amount effective to reduce a cancer stem cell population and/or cancer cell population in an animal with or animal model for myeloid leukemia or another cancer associated with IL3Rα-expressing cells by about 25%, 30%, 40%, 50%, 75%, 80%, 85%, 90%, 95% or 98% relative to a negative control. In a specific embodiment, the reduction in the cancer stem cell population in the animal or animal model is at least 25% relative to a negative control. In some embodiments, the animal is a human. In other embodiments, the animal is a non-human animal.

The present invention provides pharmaceutical compositions comprising an antibody conjugate in an amount effective to reduce a cancer stem cell population and/or cancer cell population in an animal with or animal model for myeloid leukemia or another cancer associated with IL3Rα-expressing cells by about 25%, 30%, 40%, 50%, 75%, 80%, 85%, 90%, 95% or 98% relative to a negative control, wherein the conjugate comprises an antibody that binds to the IL3Rα chain and a cytotoxic agent or other anticellular moiety. In a specific embodiment, the conjugate comprises $V_H$ and $V_L$ domains of the 26292, 32701, 32701 or 32716 antibody. In another embodiment, the conjugate comprises one or more or all of the CDRs of the CDRs of the 26292, 32703, 32701 or 32716 antibody. In a specific embodiment, the reduction in the cancer stem cell population in the animal or animal model is at least 25% relative to a negative control. In some embodiments, the animal is human. In other embodiments, the animal is a non-human animal.

5.8 Therapeutic and Prophylactic Uses of Conjugates

The present invention provides methods of treating, preventing and/or managing a disorder characterized by cells expressing the IL-3 receptor alpha subunit, the methods comprising administering to a subject (preferably, a human) in need thereof a pharmaceutical composition comprising an effective amount of an antibody or antibody conjugate of the invention. In one embodiment, the antibody or antibody conjugates of the invention are administered as monotherapy for the prevention, treatment, and/or management of a disorder characterized by cells expressing the IL-3 receptor alpha subunit. In other embodiments, the antibody or antibody conjugates are administered in combination with another therapy. In certain embodiments, the antibodies and antibody conjugates of the invention are administered in combination, and optionally with other therapies.

The present invention is directed to therapies which involve administering one or more of the antibody or antibody conjugates of the invention and compositions comprising the antibody or antibody conjugates to a subject, preferably a human subject, for preventing, treating, managing, and/or ameliorating disease or disorder that displays or is characterized by IL-3 receptor alpha subunit expression or one or more symptoms thereof. In one embodiment, the invention provides a method of preventing, treating, managing, and/or ameliorating a disease or disorder that displays or is characterized by IL-3 receptor alpha subunit expression or one or more symptoms thereof, said method comprising administering to a subject in need thereof an effective amount of one or more antibody or antibody conjugates of the invention. Such diseases and disorders include cancer, allergic diseases, inflammatory diseases, and autoimmune diseases.

The invention also provides methods comprising administering to a subject in need thereof an antibody or antibody conjugate of the invention and one or more therapies (e.g., one or more prophylactic or therapeutic agents) other than the antibody or antibody conjugate of the invention that are currently being used, have been used, are known to be useful, or may be useful in the prevention, treatment, management, and/or amelioration of a disease or disorder that displays or is characterized by IL-3 receptor alpha subunit expression or one or more symptoms thereof. The prophylactic or therapeutic agents of the combination therapies of the invention can be administered sequentially or concurrently. In a specific embodiment, the combination therapies of the invention comprise an effective amount of an antibody or antibody conjugate of the invention and an effective amount of at least one other therapy which has the same mechanism of action as said an antibody or antibody conjugate. In a specific embodiment, the combination therapies of the invention comprise an effective amount of an antibody or antibody conjugate of the invention and an effective amount of at least one other therapy (e.g., prophylactic or therapeutic agent) which has a different mechanism of action than said antibody or antibody conjugate. In certain embodiments, the combination therapies of the present invention improve the prophylactic or therapeutic effect of an antibody or antibody conjugate of the invention by functioning together with an antibody or antibody conjugate to have an additive or synergistic effect. In certain embodiments, the combination therapies of the present invention reduce the side effects associated with the prophylactic or therapeutic agents. In other embodiments, the combination therapies are administered prior to, during, or after the administration of the compositions of the invention.

Cancer or a neoplastic disease, including, but not limited to, neoplasms, tumors, metastases, or any disease or disorder characterized by uncontrolled cell growth, can be treated, suppressed, delayed, managed, inhibited or prevented by administering to a subject in need thereof a prophylactically effective regimen or a therapeutically effective regimen, the regimen comprising administering to the patient a compound of the invention. In specific embodiments, the invention encompasses the treatment, suppression, delaying, management, inhibiting of growth and/or progression, and prevention of cancer or neoplastic disease as described herein.

In one embodiment, the antibody or antibody conjugates of the invention are administered as monotherapy for the prevention, treatment, and/or management of cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient an antibody or antibody conjugate of the invention or a pharmaceutical composition of the invention, wherein the patient has been diagnosed with cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient an antibody or antibody conjugate of the invention or a pharmaceutical composition of the invention, wherein the patient has relapsed from cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient an antibody or antibody conjugate of the invention or a pharmaceutical composition of the invention, wherein the patient has failed or is failing therapy.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient an antibody or antibody conjugate of the invention or a pharmaceutical composition of the invention, wherein the patient is in remission from cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient an antibody or antibody conjugate of the invention or a pharmaceutical composition of the invention, wherein the patient is refractory to therapy.

In one embodiment, the cancer is a hematologic cancer. For instance, the cancer can be leukemia, lymphoma, myelodysplastic syndrome (MDS), or myeloma. In another embodiment, the cancer is a solid tumor.

In one embodiment of this aspect, the patient has received or is receiving another therapy. In another embodiment of this aspect, the patient has not previously received a therapy for the prevention, treatment, and/or management of the cancer.

The medical practitioner can diagnose the patient using any of the conventional cancer screening methods including, but not limited to physical examination (e.g., prostate examination, rectal examination, breast examination, lymph nodes examination, abdominal examination, skin surveillance, testicular exam, general palpation), visual methods (e.g., colonoscopy, bronchoscopy, endoscopy), PAP smear analyses (cervical cancer), stool guaiac analyses, blood tests (e.g., complete blood count (CBC) test, prostate specific antigen (PSA) test, carcinoembryonic antigen (CEA) test, cancer antigen (CA)-125 test, alpha-fetoprotein (AFP), liver function tests), karyotyping analyses, bone marrow analyses (e.g., in cases of hematological malignancies), histology, cytology, flow cytometry, a sputum analysis, and imaging methods (e.g., computed tomography (CT), magnetic resonance imaging (MRI), ultrasound, X-ray imaging, mammography, PET scans, bone scans, radionuclide scans).

Another aspect of the invention relates to a method of preventing, treating, and/or managing a solid tumor in a patient (e.g., a human patient), the method comprising administering to a patient in need thereof a prophylactically effective regimen or a therapeutically effective regimen, the regimen comprising administering to the patient an antibody or antibody conjugate or pharmaceutical composition of the invention wherein the patient has been diagnosed with a solid tumor, and wherein the patient has undergone a primary therapy to reduce the bulk of the tumor. The primary therapy to reduce the tumor bulk size is preferably a therapy other than an antibody or antibody conjugate of the invention. In specific embodiment of this aspect, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, or retinoblastoma.

Another aspect of the invention relates to a method of preventing, treating, and/or managing cancer, the method comprising administering to a patient in need thereof a prophylactically effective regimen or a therapeutically effective regimen, the regimen comprising administering to the patient an antibody or antibody conjugate of the invention, wherein the patient received another therapy. In some embodiments, the prior therapy is, for example, chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or any combination thereof.

In some embodiments, the prior therapy has failed in the patient. In some embodiments, the therapeutically effective regimen comprising administration of an antibody or antibody conjugate of the invention is administered to the patient immediately after the patient has undergone the prior therapy. For instance, in certain embodiments, the outcome of the prior therapy may be unknown before the patient is administered the antibody or antibody conjugate.

Another aspect of the invention relates to a method of preventing cancer in a patient (e.g., a human patient), the method comprising administering to a patient in need thereof a prophylactically effective regimen or a therapeutically effective regimen, the regimen comprising administering to the patient an antibody or antibody conjugate of the invention, wherein the cancer in the patient has entered remission. In some embodiments of this aspect, through administration of a prophylactically effective regimen or a therapeutically effective regimen, the medical practitioner can effectively cure the cancer, or prevent its reoccurrence.

Another aspect of the invention relates to a method of preventing, treating, and/or managing cancer in a patient (e.g., a human patient), the method comprising administering to a patient in need thereof a prophylactically effective regimen or a therapeutically effective regimen, the regimen comprising administering to the patient a compound or composition of the invention, wherein the antibody or antibody conjugate is administered at a dose that is lower than the maximum tolerated dose (MTD) over a period of three months, four months, six months, nine months, 1 year, 2 years, 3 years, 4 years, or more.

Another aspect of the invention relates to a method of preventing, treating, and/or managing cancer in a patient (e.g., a human patient), the method comprising administering to a patient in need thereof a prophylactically effective regimen or a therapeutically effective regimen, the regimen comprising administering to the patient an antibody or antibody conjugate of the invention, wherein the antibody or antibody conjugate is administered at a dose that is lower than the human equivalent dosage (HED) of the no observed adverse effect level (NOAEL) over a period of three months, four months, six months, nine months, 1 year, 2 years, 3 years, 4 years, or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., $mg/m^2$). In specific embodiments, the NOAELs are determined in mice, hamsters, rats, ferrets, guinea pigs, rabbits, dogs, primates (monkeys, marmosets, squirrel monkeys, baboons), micropigs, or minipigs. For a discussion on the use of NOAELs and their extrapolation to determine human equivalent doses, see *Guidance for industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005.

While not being bound by any specific theory, Applicants believe that by the administration of the prophylactically and/or therapeutically effective regimens, the cancer stem cell population of a cancer/tumor is stabilized or reduced, so as to limit or prevent the potential repopulation of the tumor.

In certain embodiments of these aspects, the regimens comprise administering a prophylactically effective regimen and/or a therapeutically effective regimen, wherein the regimen results in a reduction in the cancer stem cell population in the patient. In one embodiment, the patient undergoing the regimen is monitored to determine whether the regimen has resulted in a reduction in the cancer stem cell population in the patient.

Typically, the monitoring of the amount of cancer stem cells is conducted by detecting the amount of cancer stem cells in a specimen extracted from the patient. Methods of detecting the amount of cancer stem cells in a specimen are described infra in Section 5.9. This monitoring step is typically performed at least 1, 2, 4, 6, 7, 8, 10, 12, 14, 15, 16, 18, 20, or 30, 60, 90, 120 days, 6 months, 9 months, 12 months, or >12 months after the patient begins receiving the regimen.

In some embodiments, the specimen may be a blood specimen, wherein the amount of cancer stem cells per unit of volume (e.g., 1 ml) or other measured unit (e.g., per unit field in the case of a histological analysis) is quantitated. In certain embodiments, the amount of cancer stem cells is determined as a portion (e.g., a percentage) of the cancer cells present in the blood specimen, as a subset of the cancer cells present in the blood specimen, or as a subset of a subset of the cancer cells present in the blood specimen. The amount of cancer stem cells, in other embodiments, can be determined as a percentage of the total blood cells.

In other embodiments, the specimen extracted from the patient is a tissue specimen (e.g., a biopsy extracted from suspected cancerous tissue), where the amount of cancer stem cells can be measured, for example, on the basis of the amount of cancer stem cells per unit weight of the tissue. In certain embodiments, the amount of cancer stem cells is determined as a portion (e.g., a percentage) of the cancer cells present in the tissue, as a subset of the cancer cells present in the tissue, or as a subset of a subset of the cancer cells present in the tissue.

The amount of cancer stem cells in the extracted specimen can be compared with the amount of cancer stem cells measured in reference samples to assess the efficacy of the regimen, and the amelioration of the cancer under therapy. In one embodiment, the reference sample is a specimen extracted from the patient undergoing therapy, wherein the specimen is extracted from the patient at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the amount of cancer stem cells in the extracted specimen can be compared with a predetermined reference range. In a specific embodiment, the predetermined reference range is based on i) the amount of cancer stem cells obtained from a population(s) of patients suffering from the same type of cancer as the patient undergoing the therapy, or ii) the amount of stem cells obtained from a population(s) of patients without cancer.

If the reduction in the amount of cancer stem cells is determined to be too small upon comparing the amount of cancer stem cells in the specimen extracted from the patient undergoing the regimen with the reference specimen, then the medical practitioner has a number of options to adjust the regimen. For instance, the medical practitioner can then increase either the dosage of the compound or composition of the invention administered, the frequency of the administration, the duration of administration, or any combination thereof. In a specific embodiment, after the determination is made, a second effective amount of a compound or composition of the invention can be administered to the patient.

In certain embodiments, if the reduction in the amount of cancer stem cells is determined to be acceptable upon comparing the amount of cancer stem cells in the sample obtained from the patient undergoing the therapeutic or prophylactic regimen with the reference sample, then the medical practitioner may elect not to adjust the regimen. For instance, the medical practitioner may elect not to increase either the dosage of the compound or composition of the invention being administered, the frequency of the administration, the duration of administration, or any combination thereof. Further, the medical practitioner may elect to add additional therapies or combine therapies.

In other embodiments, the regimens comprise administering a prophylactically effective regimen and/or a therapeutically effective regimen, wherein the regimen results in a reduction in the amount of cancer cells in the patient. In one embodiment, the patient undergoing the regimen is monitored to determine whether the regimen has resulted in a reduction in the amount of cancer cells in the patient.

Typically, the monitoring of the amount of cancer cells is conducted by detecting the amount of cancer cells in a specimen extracted from the patient. Methods of detecting the amount of cancer cells in a specimen are described infra in Section 5.10. This monitoring step is typically performed at least 1, 2, 4, 6, 7, 8, 10, 12, 14, 15, 16, 18, 20, or 30, 60, 90, 120 days, 6 months, 9 months, 12 months, or >12 months after the patient begins receiving the regimen.

In some embodiments, the specimen may be a blood specimen, wherein the amount of cancer cells per unit of volume (e.g., 1 ml) or other measured unit (e.g., per unit field in the case of a histological analysis) is quantitated. The cancer cell population, in certain embodiments, can be determined as a percentage of the total blood cells.

In some embodiments, the sample obtained from the patient may be a bone marrow specimen, wherein the amount of cancer cells per unit of volume (e.g., 1 ml) or other measured unit (e.g., per unit field in the case of a histological analysis) is quantitated. The cancer cell population, in certain embodiments, can be determined as a percentage of the total bone marrow cells.

In other embodiments, the specimen extracted from the patient is a tissue specimen (e.g., a biopsy extracted from suspected cancerous tissue), where the amount of cancer cells can be measured, for example, on the basis of the amount of cancer cells per unit weight of the tissue. The amount of cancer cells can also be measured using immunohistochemistry or flow cytometry.

The amount of cancer cells in the extracted specimen can be compared with the amount of cancer cells measured in reference samples to assess the efficacy of the regimen and amelioration of the cancer under therapy. In one embodiment, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the cancer cell population in the extracted specimen can be compared with a predetermined reference range. In a specific embodiment, the predetermined reference range is based on the amount of cancer cells obtained from a population(s) of patients suffering from the same type of cancer as the patient undergoing the therapy.

If the reduction in the cancer cell population is judged too small upon comparing the amount of cancer cells in the specimen extracted from the patients undergoing therapy with the reference specimen, then the medical practitioner has a number of options to adjust the therapeutic regimen. For instance, the medical practitioner can then either increase the dosage of the compound or composition of the invention administered, the frequency of the administration, the duration of administration, or any combination thereof. In a specific embodiment, after the determination is made, a second effective amount of a compound or composition of the invention can be administered to the patient.

If the reduction in the cancer cell population is judged to be adequate upon comparing the amount of cancer cells in the specimen extracted from the patients undergoing therapy with the reference specimen, then the medical practitioner may elect not to adjust the therapeutic regimen. For instance, the medical practitioner may elect not to increase the dosage of the compound or composition of the invention administered, the frequency of the administration, the duration of administration, or any combination thereof.

The above monitoring methods can also be used to monitor the amount of IL-3 receptor alpha subunit-expressing cells where the disease or disorder is not a cancer, i.e., in allergic disease or autoimmune disease.

In embodiments, the medical practitioner may elect to measure the cancer population using in vivo imaging techniques. For example, a ligand for a tumor marker can be conjugated to a radioisotope, photon emitting compound, or other signal emitting compound, and then the ligand can be injected into the patient. The cancer cells can then be quantitated by measuring the signal generated when the ligand binds to the cancer cells in vivo.

5.8.1 Dosage and Frequency of Administration

The amount of an antibody, antibody conjugate or pharmaceutical composition of the invention used in the prophylactic and/or therapeutic regimens which will be effective in the prevention, treatment, and/or management of disorders characterized by cells expressing the IL-3 receptor alpha subunit alpha subunit including cancer, can be determined by methods disclosed herein. The frequency and dosage will vary also according to factors specific for each patient depending on the specific antibody or antibody conjugate administered, the severity of the (cancerous) condition, the route of administration, as well as age, body, weight, response, and the past medical history of the patient. For example, the dosage of an antibody or antibody conjugate of the invention which will be effective in the treatment, prevention, and/or management of cancer can be determined by administering the antibody or antibody conjugate to an animal model such as, e.g., the animal models disclosed herein or known in to those skilled in the art. In addition, in vitro assays may optionally be employed to help identify optimal dosage ranges.

In some embodiments, the prophylactic and/or therapeutic regimens comprise titrating the dosages administered to the patient so as to achieve a specified measure of therapeutic efficacy. Such measures include a reduction in the amount of cancer stem cells in or from the patient and/or a reduction in the amount of cancer cells in or from the patient.

In some embodiments, the prophylactic and/or therapeutic regimens comprise administering dosages and regimens of an antibody, antibody conjugate or pharmaceutical composition of the invention that are effective to reduce cancer stem cells. Methods that can be used to determine the amount of cancer stem cells in a patient prior to, during, and/or following therapy are discussed infra in Section 5.9.

In certain embodiments, the dosage of the antibody, antibody conjugate of the invention in the prophylactic and/or therapeutic regimen is adjusted so as to achieve a reduction in the amount of cancer stem cells found in a test specimen extracted from a patient after undergoing the therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic or therapeutic regimen. In specific embodiments, the amount of cancer stem cells in the test specimen is at least 2%, 5%, 10%, 15%, 20%, 30%, 40%, 50%, 60%, 70%, 80%, 90%, 95%, or 99% lower than in the reference sample.

In other embodiments, the dosage of the antibody or antibody conjugate of the invention in the prophylactic and/or therapeutic regimen is adjusted so as to achieve a reduction in the amount of cancer stem cells found in a test specimen extracted from a patient after undergoing the prophylactic and/or therapeutic regimen, as compared with a reference sample, wherein the reference sample specimen is extracted from a healthy, noncancer-afflicted patient. In specific embodiments, the amount of cancer stem cells in the test specimen is at least within 60%, 50%, 40%, 30%, 20%, 15%, 10%, 5%, or 2% of the amount of cancer stem cells in the reference sample.

In some embodiments, the dosage of the antibody or antibody conjugate of the invention in the prophylactic and/or therapeutic regimen is adjusted so as to achieve an amount of cancer stem cells that falls within a predetermined reference range. In these embodiments, the amount of cancer stem cells in a test specimen is compared with a predetermined reference range. In a specific embodiment, the predetermined reference range is based on the amount of cancer stem cells obtained from a population(s) of patients suffering from the same type of cancer as the patient undergoing the therapy.

In some embodiments, the prophylactic and/or therapeutic regimens comprise administering dosages of the antibody, antibody conjugate or pharmaceutical composition of the invention that are effective to reduce the cancer cell population. Methods that can be used to determine the cancer cell population in a patient undergoing treatment are discussed infra in Section 5.10.

In certain embodiments, the dosage of the antibody or antibody conjugate of the invention in the prophylactic and/or therapeutic regimen is adjusted so as to achieve a reduction in the amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic and/or therapeutic regimen. In specific embodiments, the amount of cancer cells in the test specimen is at least 2%, 5%, 10%, 15%, 20%, 30%, 40%, 50%, or 60% lower than in the reference sample.

In some embodiments, the dosage of the antibody or antibody conjugate of the invention in the prophylactic and/or therapeutic regimen is adjusted so as to achieve an amount of cancer cells that falls within a predetermined reference range. In these embodiments, the amount of cancer cells in a test specimen is compared with a predetermined reference range.

In other embodiments, the dosage of the antibody or antibody conjugate of the invention in prophylactic and/or therapeutic regimen is adjusted so as to achieve a reduction in the amount of cancer cells found in a test specimen extracted from a patient after undergoing the prophylactic and/or therapeutic regimen, as compared with a reference sample, wherein the reference sample is a specimen extracted from a healthy, noncancer-afflicted patient. In specific embodiments, the amount of cancer cells in the test specimen is at least within 60%, 50%, 40%, 30%, 20%, 15%, 10%, 5%, or 2% of the amount of cancer cells in the reference sample.

In treating certain human patients having solid tumors, extracting multiple tissue specimens from a suspected tumor site may or may not prove impracticable. In these embodiments, the dosage of the compounds of the invention in the prophylactic and/or therapeutic regimen for a human patient is extrapolated from doses in animal models that are effective to reduce the amount of cancer stem cells in those animal models. In the animal models, the prophylactic and/or therapeutic regimens are adjusted so as to achieve a reduction in the amount of cancer stem cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the amount of cancer stem cells in the test specimen is at least 2%, 5%, 10%, 15%, 20%, 30%, 40%, 50%, or 60% lower than in the reference sample. The doses effective in reducing the amount of cancer stem cells in the animals can be normalized to body surface are ($mg/m^2$) to provide an equivalent human dose.

The prophylactic and/or therapeutic regimens disclosed herein comprise administration of an antibody or antibody conjugate of the invention or pharmaceutical compositions thereof to the patient in a single dose or in multiple doses (e.g., 1, 2, 3, 4, 5, 6, 7, 8, 10, 15, 20, or more doses).

In one embodiment, the prophylactic and/or therapeutic regimens comprise administration of an antibody or antibody conjugate of the invention or pharmaceutical compositions thereof in multiple doses. When administered in multiple doses, the antibody, antibody conjugate or pharmaceutical compositions are administered with a frequency and in an amount sufficient to prevent, treat, and/or manage the condition. In one embodiment, the frequency of administration ranges from once a day up to about once every eight weeks. In another embodiment, the frequency of administration ranges from about once a week up to about once every six weeks. In another embodiment, the frequency of administration ranges from about once every three weeks up to about once every four weeks. In certain embodiments, the antibody or antibody conjugate is administered over a period of one week to two years. In yet another embodiment, the antibody or antibody conjugate is administered over a period of two weeks or greater. In other embodiments, the antibody or antibody conjugate is administered over a period of two weeks to one year. In further embodiments, the antibody or antibody conjugate is administered over a period of two weeks to six months. In some embodiments, the antibody or antibody conjugate is administered over a period of two weeks to twelve weeks. In yet other embodiments, the antibody or antibody conjugate is administered over a period of two weeks to six weeks. In certain embodiments, the antibody or antibody conjugate is administered once a week, twice a week, three times a week, four times a week, five times a week, six times a week, or seven times a week. In preferred embodiments, the antibody or antibody conjugate is administered at least three times a week. In other preferred embodiments, the compound is administered daily for five consecutive days, or daily for seven consecutive days. In other embodiments, the antibody or antibody conjugate is administered once a day, twice a day, three times a day, four times a day, or five times a day. In preferred embodiments, the antibody or antibody conjugate is administered three times a week over a period of two weeks. In some embodiments, each time the antibody or antibody conjugate is administered, it is administered at a dose of 4 µg/kg per day or greater. In some embodiments, the compound is administered for one, two, three, four, five, six, seven, eight, nine, ten, eleven, twelve, thirteen, fourteen, or fifteen cycles.

In a specific embodiment, the antibody is administered at a dose of 0.001 mg/kg per day to 100 mg/kg per day. In another embodiment, the antibody conjugate is administered at a dose of 0.001 mg/kg per day to 10 mg/kg per day. In certain embodiments, the antibody is administered at a dose of 0.1 mg/kg per day or greater. In other embodiments, the antibody is administered at a dose in a range of between about 0.01 mg/kg per day to about 20 mg/kg per day.

In a specific embodiment, the conjugate is administered at a dose of 0.001 mg/kg to 5 mg/kg per day. In specific embodiments, the conjugate is administered at a dose in a range of between about 4 µg/kg per day to about 20 µg/kg per day. In further embodiments, the conjugate is administered at doses up to and including the maximum tolerated dose without toxicity. In specific embodiments, where the disease is myeloid leukemia, the dosage given is in a range of between greater than 0.01 mg/kg per day to about 60 mg/kg per day.

In some embodiments of the invention, the dosage of an antibody or antibody conjugate of the invention or pharmaceutical composition thereof administered is at least 1.5, 1.6, 1.8, 2, 2.5, 3, 4, 5, 6, 7, 8, 10, 20, 30, 40, 50, 60, 70, 80, 90 or 100 times lower than the maximum tolerated dose (MTD) over a period of three months, four months, six months, nine months, 1 year, 2 years, 3 years, 4 years or more.

In some embodiments of the invention, the dosage of an antibody or antibody conjugate of the invention or pharmaceutical composition thereof administered is at least 1.1, 1.2, 1.3, 1.4, 1.5, 1.6, 1.8, 2, 2.5, 3, 4, 5, 6, 7, 8, 10, 20, 30, 40, 50, 60, 70, 80, 90 or 100 times lower than the human equivalent dose (HED) of the no observed adverse effect level (NOAEL) over a period of three months, four months, six months, nine months, 1 year, 2 years, 3 years, 4 years or more.

Generally, the dosage of an antibody of the invention administered to a subject to prevent, treat and/or manage cancer in the range of 0.001 to 100 mg/kg, more typically, 0.1 to 20 mg/kg of the subject's body weight.

Generally, the dosage of a conjugate of the invention administered to a subject to prevent, treat, and/or manage cancer is in the range of 0.0001 to 0.5 mg/kg, and more typically, in the range of 0.1 µg/kg to 100 µg/kg, of the subject's body weight. In one embodiment, the dosage administered to a subject is in the range of 0.1 µg/kg to 50 µg/kg, or 1 µg/kg to 50 µg/kg, of the subject's body weight, more preferably in the range of 0.1 µg/kg to 25 µg/kg, or 1 µg/kg to 25 µg/kg, of the patient's body weight.

In a specific embodiment, the dosage of a conjugate of the invention administered to a subject to prevent, treat, and/or manage cancer in a patient is 500 µg/kg or less, preferably 250 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, or 1 µg/kg or less of a patient's body weight. In another specific embodiment, the dosage of an antibody of the invention administered to a subject to prevent, treat and/or manage cancer in a patient is a unit dose of 2 mg, 5 mg, 10 mg, 15 mg, 30 mg, 50 mg, 100 mg, 150 mg, 200 mg, 250 mg, 300 mg, 400 mg, 500 mg, 750 mg, 1000 mg, or 1 to 50 mg, 10 to 100 mg, 10 to 500 mg, 10 to 1000 mg, 100 to 500 mg or 100 to 1000 mg.

In another specific embodiment, the dosage of a conjugate of the invention administered to a subject to prevent, treat, and/or manage cancer in a patient is a unit dose of 0.1 µg to 20 µg, 0.1 µg to 15 µg, 0.1 µg to 12 µg, 0.1 µg to 10 µg, 0.1 µg to 8 µg, 0.1 µg to 7 µg, 0.1 µg to 5 µg, 0.1 to 2.5 µg, 0.25 µg to 20 µg, 0.25 to 15 µg, 0.25 to 12 µg, 0.25 to 10 µg, 0.25 to 8 µg, 0.25 µg to 7 m g, 0.25 µg to 5 µg, 0.5 µg to 2.5 µg, 1 µg to 20 µg, 1 µg to 15 µg, 1 µg to 12 µg, 1 µg to 10 µg, 1 µg to 8 µg, 1 µg to 7 µg, 1 µg to 5 µg, or 1 µg to 2.5 µg.

In a specific embodiment, the dosage of a conjugate of the invention administered to a subject to prevent, treat, and/or manage cancer in a patient is in the range of 0.01 to 10 g/m$^2$, and more typically, in the range of 0.1 g/m$^2$ to 7.5 g/m$^2$, of the subject's body weight. In one embodiment, the dosage administered to a subject is in the range of 0.5 g/m$^2$ to 5 g/m$^2$, or 1 g/m$^2$ to 5 g/m$^2$ of the subject's body's surface area.

In other embodiments, the prophylactic and/or therapeutic regimen comprises administering to a patient one or more doses of an effective amount of an antibody or antibody conjugate of the invention, wherein the dose of an effective amount achieves a plasma level of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the antibody or antibody conjugate of the invention.

In other embodiments, the prophylactic and/or therapeutic regimen comprises administering to a patient a plurality of doses of an effective amount of an antibody or antibody conjugate of the invention, wherein the plurality of doses maintains a plasma level of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 1751 g/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the antibody or antibody conjugate of the invention for at least 1 month, 2 months, 3 months, 4 months, 5 months, 6 months, 7 months, 8 months, 9 months, 10 months, 11 months, 12 months, 15 months, 18 months, or 24 months.

In some embodiments, the prophylactic and/or therapeutic regimen comprises administration of an antibody or antibody conjugate of the invention in combination with one or more additional anticancer therapeutics. In some embodiments, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., *Goodman & Gilman's The Pharmacological Basis Of Basis Of Therapeutics*, 10$^{th}$ ed., McGraw-Hill, New York, 2001; *Physician's Desk Reference* (60$^{th}$ ed., 2006), which are incorporated herein by reference in its entirety.

5.8.2 Additional Therapies

Any therapy (e.g., therapeutic or prophylactic agent) which is useful, has been used, or is currently being used for the prevention, treatment, and/or management of a disorder characterized by IL3R alpha chain expression (e.g., cancer) can be used in compositions and methods of the invention. Therapies (e.g., therapeutic or prophylactic agents) include, but are not limited to, peptides, polypeptides, conjugates, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies and surgery. In certain embodiments, a prophylactically and/or therapeutically effective regimen of the invention comprises the administration of a combination of therapies.

Examples of cancer therapies include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; Bcl-2 inhibitors; Bcl-2 family inhibitors, including ABT-737; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

In some embodiments, the therapy(ies) used in combination with an antibody or antibody conjugate of the invention is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide). Other examples of immunomodulatory agents can be found, e.g., in U.S. Publ'n No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) used in combination with an antibody or antibody conjugate of the invention is an anti-angiogenic agent. Non-limiting examples of anti-angiogenic agents include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publ'n No. 2005/0002934 A1 at paragraphs 277-282, which is incorporated by reference in its entirety. In other embodiments, the therapy(ies) used in accordance with the invention is not an anti-angiogenic agent.

In some embodiments, the therapy(ies) used in combination with an antibody or antibody conjugate of the invention is an inflammatory agent. Non-limiting examples of anti-inflammatory agents include any anti-inflammatory agent, including agents useful in therapies for inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta$_2$-agonists (e.g., albuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTASONE™), prednisolone (PRELONE™ and PEDIAPRED™), triamcinolone, azulfidine, and inhibitors of eicosanoids (e.g., prostaglandins, thromboxanes, and leukotrienes. Other examples of anti-inflammatory agents can be found, e.g., in U.S. Publ'n No. 005/0002934 A1 at paragraphs 290-294, which is incorporated by reference in its entirety. In other embodiments, the therapy(ies) used in accordance with the invention is not an anti-inflammatory agent.

In certain embodiments, the therapy(ies) used is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, chlorambucil, cyclophosphamide, ifosfamide, decarbazine, mechlorethamine, melphalan, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclines include but are not limited to daunorubicin, doxorubicin, epirubicin, idarubicin, and mitoxantrone. Topoisomerase II inhibitors include, but are not limited to, topotecan, irinotecan, etoposide (VP-16), and teniposide. Mitotic inhibitors include, but are not limited to taxanes (paclitaxel, docetaxel), and the vinca alkaloids (vinblastine, vincristine, and vinorelbine).

The invention includes the use of agents that target cancer stem cells in combination with an antibody or antibody conjugate of the invention. In some embodiments, the agent used is an agent that binds to a marker, e.g., antigen on cancer stem cells. In a specific embodiment, the agent binds to an antigen that is expressed at a greater level on cancer stem cells than on normal stem cells. In a specific embodiment, the agent binds specifically to a cancer stem cell antigen. In other embodiments, the therapy(ies) used in accordance with the invention is an agent that binds to a marker on cancer stem cells. Non-limiting examples of antigens on cancer stem cells that can be used to target cancer stem cells include CD34+, CD44+, CD133+, CD34+, CD19+, CD20+, CD47+, CD96+, CD133+, and α2β1hi. In one embodiment, the agent that binds to a marker on cancer stem cells is an antibody. In another embodiment, the agent that binds to a marker on cancer stem cells is a ligand. In certain embodiments, the antibody or ligand is attached directly or indirectly to a therapeutic moiety. Non-limiting examples of therapeutic moieties include, but are not limited to, therapeutic enzymes, chemotherapeutic agents, cytokines, radionuclides, antimetabolites, and toxins.

In certain embodiments, antibodies that bind to a marker on cancer stem cells are substantially non-immunogenic in the treated subject. Non-immunogenic antibodies include, but are not limited to, making the antibody chimeric, humanizing the antibody, and antibodies from the same species as subject receiving the therapy. Antibodies that bind to markers in cancer stem cells can be produced using techniques known in the art. See, for example, paragraphs 539-573 of U.S. Publ'n No. 2005/0002934 A1, which is incorporated by reference in its entirety.

In some embodiments, an antibody or antibody conjugate of the invention is used in combination with radiation therapy comprising the use of x-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

Currently available cancer therapies and their dosages, routes of administration and recommended usage are known in the art and have been described in such literature as the Physician's Desk Reference (60$^{th}$ ed., 2006). In accordance with the present invention, the dosages and frequency of administration of chemotherapeutic agents are described supra.

5.8.3 Types of Disease and Disorders

The present invention provides methods of treating or preventing or managing a disease or disorder characterized by cells expressing the IL-3 receptor alpha subunit in humans by administering to humans in need of such treatment or prevention a pharmaceutical composition comprising an amount of antibody or an antibody conjugate of the invention effective to treat or prevent the disease or disorder. In certain embodiments, the disease or disorder is not a hematologic cancer. In other embodiments, the disease or disorder is an allergic disease or disorder. In other embodiments, the disease or disorder is an inflammatory disease or disorder. In another embodiment, the disease or disorder is one characterized as affecting plasmacytoid dendritic cells (e.g., dendritic cell cancers such as NK blastic leukemia and $CD4^+$ $CD56^+$ dermatologic neoplasm). In certain embodiments, the subjects have acute myelogenous leukemia (AML). In certain other embodiments, the subjects have myelodysplastic syndrome (MDS). In other embodiments, the subjects have chronic myelomonocytic leukemia (CMML), CML, ALL, hairy cell leukemia, Hodgkin's disease, or non-Hodgkin's lymphoma.

In certain embodiments, the present invention encompasses treating patients with NK blastic leukemia and/or lymphoma (also known as plasmacytoid dendritic cell lymphoma) by administering to those patients an antibody or an antibody conjugate of the invention after those patients have gone into remission following another cancer therapy. In certain embodiments, for those patients in remission, an effective amount of the antibody or antibody conjugate will be an amount effective to prolong or increase the amount of time before recurrence of the cancer.

The present invention encompasses methods for preventing, treating, managing, and/or ameliorating an inflammatory disorder or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients suffering from an infection), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a viral respiratory infection or one or more symptoms thereof.

In an embodiment of the invention, diseases that are characterized by plasmacytoid dendritic cells, which cells demonstrate high expression of the alpha chain of the IL-3 receptor, are targeted. Such diseases include, but are not limited to, HIV, herpes, CMV, autoimmune diseases, and cancers including but not limited to NK blastic lymphoma, dendritic cell cancer including plasmacytoid dendritic cell cancer, and dermatologic neoplasms.

Autoimmune Disorders

In certain embodiments, the invention provides a method of preventing, treating, managing, and/or ameliorating an autoimmune disorder or one or more symptoms thereof, said method comprising administering to a subject in need thereof a dose of an effective amount of one or more pharmaceutical compositions of the invention, wherein the cells involved in such disorders express the interleukin-3 receptor beta subunit. In autoimmune disorders, the immune system triggers an immune response and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress, destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin.

Examples of autoimmune disorders that can be prevented, treated, managed, and/or ameliorated by the methods of the invention include, but are not limited to, adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, dense deposit disease, discoid lupus, essential mixed cryoglobulinemia, fibromyalgia-fibromyositis, glomerulonephritis (e.g., IgA nephrophathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, lichen planus, lupus erythematosus, Meniere's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychrondritis, Polyendocrinopathies, polyglandular syndromes, polymyalgia rheumatica, polymyositis and dermatomyositis, post-MI, primary agammaglobulinemia, primary biliary cirrhosis, psoriasis, psoriatic arthritis, Raynauld's phenomenon, relapsing polychondritis, Reiter's syndrome, rheumatic heart disease, rheumatoid arthritis, sarcoidosis, scleroderma, Sjögren's syndrome, stiff-man syndrome, systemic lupus erythematosus, takayasu arteritis, temporal arteritis/giant cell arteritis, ulcerative colitis, urticaria, uveitis, Uveitis Opthalmia, vasculitides such as dermatitis herpetiformis vasculitis, vitiligo, and Wegener's granulomatosis.

Allergies

In certain embodiments, the invention provides a method of preventing, treating, managing, and/or ameliorating one or more allergic diseases or allergies or one or more symptoms thereof, wherein the cells involved in such diseases or allergies express the interleukin-3 receptor beta subunit, said method comprising administering to a subject in need thereof a dose of an effective amount of one or more pharmaceutical compositions of the invention. Immune-mediated allergic (hypersensitivity) reactions are classified into four types (I-IV) according to the underlying mechanisms leading to the manifestation of the allergic symptoms. Type I allergic reactions are immediate hypersensitivity reactions characterized by IgE-mediated release of vasoactive substances such as histamine from mast cells and basophils. Over hours, the mast cells and basophils release proinflammatory cytokines producing vasodilation, increased capillary permeability, glandular hypersecretion, smooth muscle spasm, and tissue infiltration with eosinophils and other inflammatory cells.

Type II allergic reactions are cytotoxic hypersensitivity reactions and involve IgG or IgM antibodies bound to cell surface antigens with subsequent complement fixation. Certain cytotoxic cells, such as killer T cells or macrophages, are activated, bind to cells coated with IgG and destroy the target cells. Type II reactions may result in cytolysis or tissue damage.

Type III reactions are immune-complex reactions resulting from deposits of circulating antigen-antibody immune complexes in blood vessels or tissues. Acute inflammation results from the immune-complex initiating a sequence of events that results in polymorphonuclear cell migration and release of lysosomal proteolytic enzymes and permeability factors in tissues.

Type IV reactions are delayed hypersensitivity reactions caused by sensitized T lymphocytes after contact with a specific antigen. Activated sensitized T lymphocytes cause immunologic injury by direct toxic effect or through release of lymphokines and other soluble substances. The activated T lymphocytes may also release cytokines that affect the activity of macrophages, neutrophils, and lymphoid killer cells.

Allergic reactions can be immediate, late-phase, or chronic. Continuous or chronic exposure to an allergen can result in chronic allergic inflammation. Tissues of sites of chronic inflammation contain eosinophils and T cells that release mediators that can cause tissue damage, increased inflammation, and increased sensitivity.

Currently, allergic reactions are treated with drugs such as antihistamines, corticosteroids, vasodilators, bronchodilators, leukotriene inhibitors, and immunomodulators which attempt to alleviate the symptoms associated with the allergic reaction.

Cancer

Any type of cancer in which the cancer stem cells or cancer cells express the interleukin-3 receptor alpha subunit can be prevented, treated, and/or managed in accordance with the invention. Non-limiting examples of cancers that can be prevented, treated, and/or managed in accordance with the invention include: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; dendritic cell cancer, including plasmacytoid dendritic cell cancer, NK blastic lymphoma (also known as cutaneous NK/T-cell lymphoma and agranular (CD4+/CD56+) dermatologic neoplasms); basophilic leukemia; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The prophylactically and/or therapeutically effective regimens are also useful in the treatment, prevention and/or management of a variety of cancers or other abnormal proliferative diseases wherein the cells of such diseases express the interleukin-3 receptor beta subunit, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. In some embodiments, cancers associated with aberrations in apoptosis are prevented, treated and/or managed in accordance with the methods of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are prevented, treated and/or managed in accordance with the methods of the invention. In other specific embodiments, a sarcoma, melanoma, or leukemia is prevented, treated and/or managed in accordance with the methods of the invention. In certain embodiments, the subjects have acute myelogenous leukemia (AML). In certain other embodiments, the subjects have myelodysplastic syndrome (MDS). In other embodiments, the subjects have chronic myelomonocytic leukemia (CMML). In other specific embodiments, myelodysplastic syndrome is prevented, treated and/or managed in accordance with the methods of the invention.

5.8.4 Target Patient Populations

In accordance with the invention, the pharmaceutical compositions of the present invention are administered to humans in need of inhibition of cells that express the alpha subunit of the interleukin-3 receptor. In certain embodiments, the growth of such cells is inhibited. In other embodiments, the conjugates of the present invention are administered to humans with diseases and disorders associated with overexpression of the IL-3 receptor. In certain embodiments, the subject does have myeloid leukemia. In other embodiments, the disease or disorder is an allergic disease or disorder. In some embodiments, the disease or disorder is an autoimmune disease. In certain embodiments, the subjects have acute myelogenous leukemia (AML). In certain other embodiments, the subjects have myelodysplastic syndrome (MDS). In other embodiments, the subjects have chronic myelomonocytic leukemia (CMML).

In accordance with the invention, pharmaceutical compositions of the present invention are administered to subjects developing, developed, or expected to develop cancer (e.g., subjects with a genetic predisposition for a particular type of cancer, subjects that have been exposed to a carcinogen, subjects with newly diagnosed cancer, subjects that have failed treatment for cancer, subjects who have relapsed from cancer, or subjects that are in remission from a particular cancer). Such subjects may or may not have been previously treated for cancer or may be in remission, relapsed, or may have failed treatment. Such patients may also have abnormal cytogenetics. The pharmaceutical compositions may be used as any line of cancer therapy, e.g., a first line, second line, or third line of cancer therapy. In a specific embodiment, the subject to receive or receiving a pharmaceutical composition of the invention is receiving or has received other cancer therapies. In another embodiment the subject to receive a pharmaceutical composition of the invention is receiving other cancer therapies and pharmaceutical compositions of the invention are administered to the subject before any adverse effects or intolerance of these other cancer therapies occurs. In an alternative embodiment, the subject to receive or receiving a pharmaceutical composition of the invention has not received or is not receiving other cancer therapies.

In a specific embodiment, the subject has been diagnosed with cancer using techniques known to one of skill in the art including, but not limited to, physical examination (e.g., prostate examination, breast examination, lymph nodes examination, abdominal examination, skin surveillance, general palpation), visual methods (e.g., colonoscopy, bronchoscopy, endoscopy), PAP smear analyses (cervical cancer), stool guaiac analyses, blood tests (e.g., complete blood count (CBC) test, prostate specific antigen (PSA) test, carcinoembryonic antigen (CEA) test, cancer antigen (CA)-125 test, alpha-fetoprotein (AFP), liver function tests), karyotyping analyses, bone marrow analyses (e.g., in cases of hematological malignancies), histology, flow cytometry, cytology, a sputum analysis and imaging methods (e.g., computed tomography (CT), magnetic resonance imaging (MRI), ultrasound, X-ray imaging, mammography, PET scans, radionuclide scans, bone scans). Subjects may or may not have been previously treated for cancer.

In one embodiment, a pharmaceutical composition of the invention is administered to a subject that is undergoing or has undergone surgery to remove a tumor neoplasm. In a specific embodiment, a pharmaceutical composition of the invention is administered to a subject concurrently or following surgery to remove a tumor or neoplasm. In another embodiment, a pharmaceutical composition of the invention is administered to a subject before surgery to remove a tumor or neoplasm and, in some embodiments, during and/or after surgery.

In one embodiment, a pharmaceutical composition of the invention is administered to a subject after a course of therapy with the goal of killing cancer cells. In some embodiments, the course of therapy involves the administration of bolus doses of chemotherapeutic agents and/or bolus doses of radiation therapy. In a specific embodiment, a pharmaceutical composition of the invention is administered to a subject after the subject has received a course of therapy involving a dose which is at, or is below, the maximum tolerated dose or the no observed adverse effect level doses of one or more chemotherapeutic agents and/or radiation therapy.

In certain embodiments, a pharmaceutical composition of the invention is administered to a subject as an alternative to chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy where the therapy has proven or may prove too toxic, i.e., results in unacceptable or unbearable side effects for the subject. In some embodiments, a prophylactically and/or therapeutically effective regimen is administered to a subject that is susceptible to adverse reactions from other cancer therapies. The subject may, e.g., have a suppressed immune system (e.g., post-operative patients, chemotherapy patients, and patients with immunodeficiency disease), have an impaired renal or liver function, be elderly, be a child, be an infant, have a neuropsychiatric disorder, take a psychotropic drug, have a history of seizures, or be on medication that would negatively interact with the cancer therapies.

In a specific embodiment, a pharmaceutical composition of the invention is administered to subjects that will, are or have radiation therapy. Among these subjects are those that have received chemotherapy, hormonal therapy, small molecule therapy, anti-angiogenic therapy, differentiation therapy, targeted therapy, radioimmunotherapy, epigenetic therapy, and/or biological therapy, including immunotherapy as well as those who have undergone surgery.

In another embodiment, a pharmaceutical composition of the invention is administered to subjects that will, are, or have received hormonal therapy and/or biological therapy, including immunotherapy. Among these subjects are those that have received chemotherapy, small molecule therapy, anti-angiogenic therapy, differentiation therapy, targeted therapy, radioimmunotherapy, epigenetic therapy, and/or radiation therapy as well as those who have undergone surgery.

In certain embodiments, a pharmaceutical composition of the invention is administered to a subject refractory to one or more therapies. In one embodiment, that a cancer is refractory to a therapy means that at least some significant portion of the cancer cells are not killed or their cell division is not arrested. The determination of whether the cancer cells are refractory can be made either in vivo or in vitro by any method known in the art for assaying the effectiveness of a therapy on cancer cells, using the art-accepted meanings of "refractory" in such a context. In various embodiments, a cancer is refractory where the amount of cancer cells has not been significantly reduced, or has increased. In other embodiments, that a cancer is refractory means that at least some significant portion of cancer stem cells are not killed or their cell division arrested. The determination of whether the cancer stem cells are refractory can be made either in vivo or in vitro by any methods known in the art or described herein.

In some embodiments, a pharmaceutical composition of the invention is administered to reverse the resistance to, or increase the sensitivity of cancer cells to certain hormonal, radiation and chemotherapeutic agents thereby resensitizing the cancer cells to one or more of these agents, which can then be administered (or continue to be administered) to treat or manage cancer, including to prevent metastasis. In a specific embodiment, the regimens of the invention are administered to patients with increased levels of the cytokine IL-6, which has been associated with the development of cancer cell resistance to different treatment regimens, such as chemotherapy and hormonal therapy.

In some embodiments, a pharmaceutical composition of the invention is administered to a subject with a mean absolute lymphocyte count of at least approximately 400 cells/mm$^3$, at least 500 cells/mm$^3$, at least approximately 600 cells/mm$^3$, at least approximately 700 cells/mm$^3$, at least approximately 800 cells/mm$^3$, at least approximately 900 cells/mm$^3$, at least approximately 1000 cells/mm$^3$, at least approximately 1100 cells/mm$^3$, at least approximately 1200 cells/mm$^3$. In other embodiments, a prophylactically and/or therapeutically effective regimen of the invention is administered to a subject with a mean absolute lymphocyte count of approximately 400 cells/mm$^3$ to approximately 1200 cells/mm$^3$, approximately 500 cells/mm$^3$ to approximately 1200 cells/mm$^3$, approximately 600 cells/mm$^3$ to approximately 1200 cells/mm$^3$, approximately 700 cells/mm$^3$ to approximately 1200 cells/mm$^3$, approximately 800 cells/mm$^3$ to approximately 1200 cells/mm$^3$, approximately 900 cells/mm$^3$ to approximately 1200 cells/mm$^3$, approximately 1000 cells/mm$^3$ to approximately 1200 cells/mm$^3$. In a more specific embodiment, the regimen results in a mean absolute lymphocyte count of at least approximately 400 cells/mm$^3$.

In some embodiments, a pharmaceutical composition of the invention is administered to a subject that is in remission. In a specific embodiment, the subject has no detectable cancer, i.e., no cancer is detectable using a conventional method described herein (e.g., MRI) or known to one of skill in the art. In another embodiment, a pharmaceutical composition of the invention is administered to a patient that does not have a detectable immune response to diphtheria toxin. In a preferred embodiment, the immune response is detected by ELISA.

5.8.5 Combination Therapies

The present invention also provides methods for preventing, treating, and/or managing cancer, the methods comprising administering to a patient (e.g., a human patient) in need thereof, a prophylactically and/or a therapeutically effective regimen, the regimen comprising administering to the patient a pharmaceutical composition of the invention and one or more additional therapies, said additional therapy not being an antibody or antibody conjugate of the invention. In a specific embodiment, the combination therapies of the invention comprise a pharmaceutical composition in accordance with the invention and at least one other therapy that has the same mechanism of action as said antibody or antibody conjugate. In another specific embodiment, the combination therapies of the invention comprise a pharmaceutical composition identified in accordance with the methods of the invention and at least one other therapy (e.g., prophylactic or therapeutic agent) which has a different mechanism of action than said antibody or antibody conjugate. The pharmaceutical composition of the invention and the additional therapy can be administered separately, concurrently, or sequentially. The combination of agents can act additively or synergistically. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Any therapy (e.g., therapeutic or prophylactic agent) which is useful, has been used, or is currently being used for the prevention, treatment, and/or management of cancer can be used in compositions and methods of the invention. Therapies (e.g., therapeutic or prophylactic agents) include, but are not limited to, peptides, polypeptides, antibodies, conjugates, nucleic acid molecules, small molecules, mimetic agents, synthetic drugs, inorganic molecules, and organic molecules. Non-limiting examples of cancer therapies include chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy. In certain embodiments, a prophylactically and/or therapeutically effective regimen of the invention comprises the administration of a combination of therapies.

Examples of cancer therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; histone deacetylase inhibitors (HDACs) gemcitabine hydrochloride; hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid), letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™ (see U.S. Patent Pub. No. US 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents"); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, ragaglitazar, rosiglitazone, farglitazar, sodelglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit dishevelled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer stem cells includes i) antibodies, antibody fragments, and proteins that are either naked or conjugated to a therapeutic moiety that target certain cell surface targets on cancer stem cells, or ii) small molecules known in the art including ones that can be further optimized (e.g. via chemistry) or identified via a cancer stem cell-based screen (e.g. such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mcl-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) used in combination with a compound of the invention is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) used in combination with a compound of the invention is an anti-angiogenic agent. Non-limiting examples of anti-angiogenic agents include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) used in accordance with the invention is not an anti-angiogenic agent.

In some embodiments, the therapy(ies) used in combination with a compound of the invention is an anti-inflammatory agent. Non-limiting examples of anti-inflammatory agents include any anti-inflammatory agent, including agents useful in therapies for inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., albuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTASONE™), prednisolone (PRELONE™ and PEDIAPRED™), triamcinolone, azulfidine, and inhibitors of eicosanoids (e.g., prostaglandins, thromboxanes, and leukotrienes. Other examples of anti-inflammatory agents can be found, e.g., in U.S. Publication No. 005/0002934 A1 at paragraphs 290-294, which is incorporated by reference in its entirety. In other embodiments, the therapy(ies) used in accordance with the invention is not an anti-inflammatory agent.

In certain embodiments, the therapy(ies) used is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etoposide (VP-16), and teniposide. Mitotic inhibitors include, but are not limited to taxanes (paclitaxel, docetaxel), and the vinca alkaloids (vinblastine, vincristine, and vinorelbine).

The invention includes the use of agents that target cancer stem cells in combination with a compound of the invention. In some embodiments, the agent used is an agent that binds to a marker, e.g., antigen on cancer stem cells. In a specific embodiment, the agent binds to an antigen that is expressed at a greater level on cancer stem cells than on normal stem cells. In a specific embodiment, the agent binds specifically to a cancer stem cell antigen. In other embodiments, the therapy(ies) used in accordance with the invention is an agent that binds to a marker on cancer stem cells. Non-limiting examples of antigens on cancer stem cells that can be used to target cancer stem cells include CD34+/CD38−, CD34+/CD38−/CD123+, CD44+/CD24−, CD133+, CD34+/CD10−/CD19−, CD138−/CD34−/CD19+, CD20+, CD133+/RC2+, CD44+/α2β1hi/C133+, CD47+ and CD96+. In one embodiment, the agent that binds to a marker on cancer stem cells is an antibody. In another embodiment, the agent that binds to a marker on cancer stem cells is a ligand. In certain embodiments, the antibody or ligand is attached directly or indirectly to a therapeutic moiety. Non-limiting examples of therapeutic moieties include, but are not limited to alkylating agents, anti-metabolites, plant alkaloids, cytotoxic agents, chemotherapeutic agents (e.g., a steroid, cytosine arabinoside, fluorouracil, methotrexate, aminopterin, mitomycin C, demecolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, *Pseudomonas* exotoxin, a bacterial endotoxin or the lipid A moiety of a bacterial endotoxin), growth modulators and RNase.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the α-subunit of IL-3R (i.e., the CD123 antigen). In other embodiments, the antibody, antibody-conjugate, antibody fragment, or antibody fragment-conjugate binds to the IL-3R, containing both the α and β subunits. Methods for preparing antibodies to IL-3R and mimetics of antibodies to IL-3R are described in U.S. Pat. No. 6,733,743 B2, which is incorporated herein by reference in its entirety.

In certain embodiments, antibodies or fragments that bind to a marker on cancer stem cells are substantially non-immunogenic in the treated subject. Non-immunogenic antibodies include, but are not limited to, chimerized antibodies, humanized antibodies, and antibodies from the same species as the subject receiving the therapy. Antibodies or fragments that bind to markers in cancer stem cells can be produced using techniques known in the art. See, for example, paragraphs 539-573 of U.S. Publication No. 2005/0002934 A1, which is incorporated by reference in its entirety.

The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to, therapeutic enzymes, chemotherapeutic agents, cytokines, radionuclides, toxins, RNase, and antimetabolites. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds to a cancer stem cell antigen that is not a normal stem cell. In other embodiments, the therapy(ies) is an agent that binds to a marker on cancer stem cells. In one embodiment, the agent that binds to a marker on cancer stem cells is an antibody, an antibody fragment, an antibody conjugated to a therapeutic moiety, or an antibody, or an antibody fragment conjugated to a therapeutic moiety.

In some embodiments, a compound of the invention is used in combination with radiation therapy comprising the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation-based therapy. Non-limiting examples of such therapies include a chemotherapy and radiation therapy as described supra.

Currently available cancer therapies and their dosages, routes of administration and recommended usage are known in the art and have been described in such literature as the Physician's Desk Reference (60th ed., 2006). In accordance with the present invention, the dosages and frequency of administration of chemotherapeutic agents are described supra.

5.9 Methods of Monitoring Cancer Stem Cells

As part of the therapeutically effective regimens of the invention, the cancer stem cell population can be monitored to assess the efficacy of a therapy as well as to determine prognosis of a subject with cancer or the efficacy of a therapeutically effective regimen. In certain embodiments of the therapeutically effective therapies or regimens of the invention, the therapies or regimens result in a stabilization or reduction in the cancer stem cell population in the patient. In one embodiment, the subject undergoing the regimen is monitored to assess whether the regimen has resulted in a stabilization or reduction in the cancer stem cell population in the subject.

In some embodiments, the amount of cancer stem cells in a subject is determined using a technique well-known to one of skill in the art.

In accordance with the invention, cancer stem cells comprise a unique subpopulation (often 0.1-10% or so) of a tumor that, in contrast to the remaining 90% or so of the tumor (i.e., the tumor bulk), are relatively more tumorigenic and relatively more slow-growing or quiescent. Given that conventional therapies and regimens have, in large part, been designed to attack rapidly proliferating cells (i.e., those cancer cells that comprise the tumor bulk), slower growing cancer stem cells may be relatively more resistant than faster growing tumor bulk to conventional therapies and regimens. This would explain another reason for the failure of standard oncology treatment regimens to ensure long-term benefit in most patients with advanced stage cancers. In a specific embodiment, a cancer stem cell(s) is the founder cell of a tumor (i.e., it is the progenitor of cancer cells). In some embodiments, a cancer stem cell(s) has one, two, three, or more or all of the following characteristics or properties: (i) can harbor the ability to initiate a tumor and/or to perpetuate tumor growth, (ii) can be generally relatively less mutated than the bulk of a tumor (e.g. due to slower growth and thus fewer DNA replication-dependent errors, improved DNA repair, and/or epigenetic/non-mutagenic changes contributing to their malignancy), (iii) can have many features of a normal stem cell(s) (e.g., similar cell surface antigen and/or intracellular expression profile, self-renewal programs, multi-drug resistance, an immature phenotype, etc., characteristic of normal stem cells) and may be derived from a normal stem cell(s), (iv) can be potentially responsive to its microenvironment (e.g., the cancer stem cells may be capable of being induced to differentiate and/or divide asymmetrically), (v) can be the source of metastases, (vi) can be slow-growing or quiescent, (vii) can be symmetrically-dividing, (viii) can be tumorigenic (e.g. as determined by NOD/SCID implantation experiments), (ix) can be relatively resistant to traditional therapies (i.e. chemoresistant), and (x) can comprise a subpopulation of a tumor (e.g. relative to the tumor bulk).

In other embodiments, the amount of cancer stem cells in a sample from a subject is determined/assessed using a technique described herein or well-known to one of skill in the art. Such samples include, but are not limited to, biological samples and samples derived from a biological sample. In certain embodiments, in addition to the biological sample itself or in addition to material derived from the biological sample such as cells, the sample used in the methods of this invention comprises added water, salts, glycerin, glucose, an antimicrobial agent, paraffin, a chemical stabilizing agent, heparin, an anticoagulant, or a buffering agent. In certain embodiments, the biological sample is blood, serum, urine, bone marrow or interstitial fluid. In another embodiment, the sample is a tissue sample. In a particular embodiment, the tissue sample is breast, brain, skin, colon, lung, liver, ovarian, pancreatic, prostate, renal, bone or skin tissue. In a specific embodiment, the tissue sample is a biopsy of normal or tumor tissue. The amount of biological sample taken from the subject will vary according to the type of biological sample and the method of detection to be employed. In a particular embodiment, the biological sample is blood, serum, urine, or bone marrow and the amount of blood, serum, urine, or bone marrow taken from the subject is 0.1 ml, 0.5 ml, 1 ml, 5 ml, 8 ml, 10 ml or more. In another embodiment, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

In accordance with the methods of the invention, a sample derived from a biological sample is one in which the biological sample has been subjected to one or more pretreatment steps prior to the detection and/or measurement of the cancer stem cell population in the sample. In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeablization, or homogenization followed by centrifugation, filtration, precipitation, dialysis, or chromatography, or by a combination of such pretreatment steps. In certain embodiments, the sample is pretreated by removing cells other than stem cells or cancer stem cells from the sample, or removing debris from the sample prior to the determination of the amount of cancer stem cells in the sample according to the methods of the invention.

The samples for use in the methods of this invention may be taken from any animal subject, preferably mammal, most preferably a human. The subject from which a sample is obtained and utilized in accordance with the methods of this invention includes, without limitation, an asymptomatic subject, a subject manifesting or exhibiting 1, 2, 3, 4 or more symptoms of cancer, a subject clinically diagnosed as having cancer, a subject predisposed to cancer, a subject suspected of having cancer, a subject undergoing therapy for cancer, a subject that has been medically determined to be free of cancer (e.g., following therapy for the cancer), a subject that is managing cancer, or a subject that has not been diagnosed with cancer. In certain embodiments, the term "has no detectable cancer" as used herein, refers to a subject or subjects in which there is no detectable cancer by conventional methods, e.g. MRI. In other embodiments, the term refers to a subject or subjects free from any disorder.

In certain embodiments, the amount of cancer stem cells in a subject or a sample from a subject assessed prior to therapy or regimen (e.g. at baseline) or at least 1, 2, 4, 6, 7, 8, 10, 12, 14, 15, 16, 18, 20, 30, 60, 90 days, 6 months, 9 months, 12 months, >12 months after the subject begins receiving the therapy or regimen. In certain embodiments, the amount of cancer stem cells is assessed after a certain number of doses (e.g., after 2, 5, 10, 20, 30 or more doses of a therapy). In other embodiments, the amount of cancer stem cells is assessed after 1 week, 2 weeks, 1 month, 2 months, 1 year, 2 years, 3 years, 4 years or more after receiving one or more therapies.

In certain embodiments, a positive or negative control sample is a sample that is obtained or derived from a corresponding tissue or biological fluid or tumor as the sample to be analyzed in accordance with the methods of the invention. This sample may come from the same patient or different persons and at the same or different time points.

For clarity of disclosure, and not by way of limitation, the following pertains to analysis of a blood sample from a patient. However, as one skilled in the art will appreciate, the assays and techniques described herein can be applied to other types of patient samples, including a body fluid (e.g. blood, bone marrow, plasma, urine, bile, ascitic fluid), a tissue sample suspected of containing material derived from a cancer (e.g. a biopsy) or homogenate thereof. The amount of sample to be collected will vary with the particular type of sample and method of determining the amount of cancer stem cells used and will be an amount sufficient to detect the cancer stem cells in the sample.

A sample of blood may be obtained from a patient having different developmental or disease stages. Blood may be drawn from a subject from any part of the body (e.g., a finger, a hand, a wrist, an arm, a leg, a foot, an ankle, a stomach, and a neck) using techniques known to one of skill in the art, in particular methods of phlebotomy known in the art. In a specific embodiment, venous blood is obtained from a subject and utilized in accordance with the methods of the invention. In another embodiment, arterial blood is obtained and utilized in accordance with the methods of the invention. The composition of venous blood varies according to the metabolic needs of the area of the body it is servicing. In contrast, the composition of arterial blood is consistent throughout the body. For routine blood tests, venous blood is generally used.

The amount of blood collected will vary depending upon the site of collection, the amount required for a method of the invention, and the comfort of the subject. In some embodiments, any amount of blood is collected that is sufficient to detect the amount of cancer stem cells. In a specific embodiment, 1 cc or more of blood is collected from a subject.

The amount of cancer stem cells in a sample can be expressed as the percentage of, e.g., overall cells, overall cancer cells or overall stem cells in the sample, or quantitated relative to area (e.g. cells per high power field), or volume (e.g. cells per ml), or architecture (e.g. cells per bone spicule in a bone marrow specimen).

In some embodiments, the sample may be a blood sample, bone marrow sample, or a tissue/tumor biopsy sample, wherein the amount of cancer stem cells per unit of volume (e.g., 1 mL) or other measured unit (e.g., per unit field in the case of a histological analysis) is quantitated. In certain embodiments, the cancer stem cell population is determined as a portion (e.g., a percentage) of the cancerous cells present in the blood or bone marrow or tissue/tumor biopsy sample or as a subset of the cancerous cells present in the blood or bone marrow or tissue/tumor biopsy sample. The cancer stem cell population, in other embodiments, can be determined as a portion (e.g., percentage) of the total cells. In yet other embodiments, the cancer stem cell population is determined as a portion (e.g., a percentage) of the total stem cells present in the blood sample.

In other embodiments, the sample from the patient is a tissue sample (e.g., a biopsy from a subject with or suspected of having cancerous tissue), where the amount of cancer stem cells can be measured, for example, by immunohistochemistry or flow cytometry, or on the basis of the amount of cancer stem cells per unit area, volume, or weight of the tissue. In certain embodiments, the cancer stem cell population (the amount of cancer stem cells) is determined as a portion (e.g., a percentage) of the cancerous cells present in the tissue sample or as a subset of the cancerous cells present in the tissue sample. In yet other embodiments, the cancerous stem cell population (the amount of cancer stem cells) is determined as a portion (e.g., a percentage) of the overall cells or stem cell cells in the tissue sample.

The amount of cancer stem cells in a test sample can be compared with the amount of cancer stem cells in reference sample(s) to assess the efficacy of the regimen. In one embodiment, the reference sample is a sample obtained from the subject undergoing therapy at an earlier time point (e.g., prior to receiving the regimen as a baseline reference sample, or at an earlier time point while receiving the therapy). In this embodiment, the therapy desirably results in a decrease in the amount of cancer stem cells in the test sample as compared with the reference sample. In another embodiment, the reference sample is obtained from a healthy, subject who has no detectable cancer, or from a patient that is in remission for the same type of cancer. In this embodiment, the therapy desirably results in the test sample having an equal amount of cancer stem cells, or less than the amount of cancer stem cells than are detected in the reference sample.

In other embodiments, the cancer stem cell population in a test sample can be compared with a predetermined reference range and/or a previously detected amount of cancer stem cells determined for the subject to gauge the subject's response to the regimens described herein. In a specific embodiment, a stabilization or reduction in the amount of cancer stem cells relative to a predetermined reference range and/or earlier (previously detected) cancer stem cell amount determined for the subject indicates an improvement in the subject's prognosis or a positive response to the regimen, whereas an increase relative to the predetermined reference range and/or earlier cancer stem cell amount indicates the same or worse prognosis, and/or a failure to respond to the regimen. The cancer stem cell amount can be used in conjunction with other measures to assess the prognosis of the subject and/or the efficacy of the regimen. In a specific embodiment, the predetermined reference range is based on the amount of cancer stem cells obtained from a patient or population(s) of patients suffering from the same type of cancer as the patient undergoing the therapy.

Generally, since stem cell antigens can be present on both cancer stem cells and normal stem cells, a sample from the cancer-afflicted patient will have a higher stem cell count than a sample from a healthy, subject who has no detectable cancer due to the presence of the cancer stem cells. The therapy will desirably result in a cancer stem cell count for the test sample (e.g., the sample from the patient undergoing therapy) that decreases and becomes increasingly closer to the stem cell count in a reference sample that is sample from a healthy, subject who has no detectable cancer.

If the reduction in the amount of cancer stem cells is determined to be inadequate upon comparing the amount of cancer stem cells in the sample from the subject undergoing the regimen with the reference sample, then the medical practitioner has a number of possible options to adjust the regimen. For instance, the medical practitioner can then increase either the dosage or intensity of the therapy administered, the frequency of the administration, the duration of administration, combine the therapy with another therapy(ies), change the management altogether including halting therapy, or any combination thereof.

In certain embodiments, the dosage, frequency and/or duration of administration of a therapy is modified as a result of the change in the amount of cancer stem cells detected in or from the treated patient. For example, if a subject receiving therapy for leukemia has a cancer stem cell measurement of 2.5% of his tumor prior to therapy and 5% after 6 weeks of therapy, then the therapy or regimen may be altered or stopped because the increase in the percentage of cancer stem cells indicates that the therapy or regimen is not optimal. Alternatively, if another subject with leukemia has a cancer stem cell measurement of 2.5% of his tumor prior to therapy and 1% after 6 weeks of therapy, then the therapy or regimen may be continued because the decrease in the percentage of cancer stem cells indicates that the therapy or regimen is effective.

The amount of cancer stem cells can be monitored/assessed using standard techniques known to one of skill in the art. Cancer stem cells can be monitored by, e.g., obtaining a sample, such as a tissue/tumor sample, blood sample or a bone marrow sample, from a subject and detecting cancer stem cells in the sample. The amount of cancer stem cells in a sample (which may be expressed as percentages of, e.g., overall cells or overall cancer cells) can be assessed by detecting the expression of antigens on cancer stem cells. Techniques known to those skilled in the art can be used for measuring these activities. Antigen expression can be assayed, for example, by immunoassays including, but not limited to, western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunofluorescence, protein A immunoassays, flow cytometry, and FACS analysis. In such circumstances, the amount of cancer stem cells in a test sample from a subject may be determined by comparing the results to the amount of stem cells in a reference sample (e.g., a sample from a subject who has no detectable cancer) or to a predetermined reference range, or to the patient him/herself at an earlier time point (e.g. prior to, or during therapy).

In a specific embodiment, the cancer stem cell population in a sample from a patient is determined by flow cytometry. This method exploits the differential expression of certain surface markers on cancer stem cells relative to the bulk of the tumor. Labeled antibodies (e.g., fluorescent antibodies) can be used to react with the cells in the sample, and the cells are subsequently sorted by FACS or flow cytometry methods. In some embodiments, a combination of cell surface markers are utilized in order to determine the amount of cancer stem cells in the sample. For example, both positive and negative cell sorting may be used to assess the amount of cancer stem cells in the sample. Cancer stem cells for specific tumor types can be determined by assessing the expression of markers on cancer stem cells. In certain embodiments, the tumors harbor cancer stem cells and their associated markers as set forth in Table 2 below, which provides a non-limiting list of cancer stem cell phenotypes associated with various types of cancer.

TABLE 2

| Tumor | Cancer Stem Cell Phenotype |
|---|---|
| Leukemia (AML) | CD34+/CD38− |
| Breast | CD44+/CD24− |
| Brain | CD133+ |
| Leukemia (ALL) | CD34+/CD10−/CD19− |
| Ovarian | CD44+/CD24− |
| Multiple Myeloma | CD138−/CD34−/CD19+ |
| Chronic myelogenous leukemia | CD34+/CD38− |
| Melanoma | CD20+ |
| Ependymoma | CD133+/RC2+ |
| Prostate | CD44+/$\alpha_2\beta_1^{hi}$/CD133+ |

Additional cancer stem cell markers include, but are not limited to, CD123, CLL-1, combinations of SLAMs (signaling lymphocyte activation molecule family receptors; see Yilmaz, et al., Hematopoiesis 107: 924-930 (2006)), such as CD150, CD244, and CD48, and those markers disclosed in U.S. Pat. No. 6,004,528 to Bergstein, in pending U.S. patent application Ser. No. 09/468,286, and in U.S. Patent Application Publication Nos. 2006/0083682, 2007/0036800, 2007/0036801, 2007/0036802, 2007/0041984, 2007/0036803, and 2007/0036804, each of which are incorporated herein by reference in their entirety. See, e.g., Table 1 of U.S. Pat. No. 6,004,528 and Tables 1, 2, and 3 of U.S. patent application Ser. No. 09/468,286 and U.S. Patent Application Publication Nos. 2006/0083682, 2007/0036800, 2007/0036801, 2007/0036802, 2007/0041984, 2007/0036803, and 2007/0036804.

In a specific embodiment the cancer stem population in a sample, e.g., a tissue sample, such as a solid tumor biopsy, is determined using immunohistochemistry techniques. This method exploits the differential expression of certain surface markers on cancer stem cells relative to the bulk of the tumor. Labeled antibodies (e.g., fluorescent antibodies) can be used to react with the cells in the sample, and the tissue is subsequently stained. In some embodiments, a combination of certain cell surface markers are utilized in order to determine the amount of cancer stem cells in the sample. Cancer stem cells for specific tumor types can be determined by assessing the expression of certain markers that are specific to cancer stem cells. In certain embodiments, the tumors harbor cancer stem cells and their associated markers as set forth in Table 2 above.

Suitable cancer stem cell antigens may be identified: (i) through publicly available information, such as published and unpublished expression profiles including cell surface antigens of cancer stem cells of a particular tumor type or adult stem cells for a particular tissue type (e.g. Table 2), and/or (ii) by cloning cancer stem cells or adult stem cells of a particular tumor or tissue type, respectively, in order to determine their expression profiles and complement of cell surface antigens. Cloning of normal stem cells is a technique routinely employed in the art (Uchida, et al., Curr Opin Immunol, 5:177-184 (1993)). In fact, this same technique is used to identify normal stem cells and cancer stem cells. Moreover, assumption that a proportion of normal stem cell gene products, e.g. cell surface antigens, will also be present on cancer stem cells derived from the same tissue type has proven an effective way to identify cancer stem cell gene products and cancer stem cells. For example, knowledge that the normal hematopoietic stem cell was CD34+/CD38− resulted in the determination that acute myeloid leukemia (AML) stem cells is similarly CD34+/CD38−. This indeed was confirmed by standard stem cell cloning techniques (See Bonnet, et al., Nat Med 3:730-737 (1997)). Brain cancer stem cells were similarly isolated using a marker of normal (brain) stem cells, in this case CD133 (See Singh, et al., Nature 432(7015):396-401 (2004)).

In certain embodiments using flow cytometry of a sample, the Hoechst dye protocol can be used to identify cancer stem cells in tumors. Briefly, two Hoechst dyes of different colors (typically red and blue) are incubated with tumor cells. The cancer stem cells, in comparison with bulk cancer cells, over-express dye efflux pumps on their surface that allow these cells to pump the dye back out of the cell. Bulk tumor cells largely have fewer of these pumps, and are therefore relatively positive for the dye, which can be detected by flow cytometry. Typically a gradient of dye positive ("dye$^+$") vs. dye negative ("dye$^−$") cells emerges when the entire population of cells is observed. Cancer stem cells are contained in the dye$^−$ or dye low (dye$^{low}$) population. For an example of the use of the Hoechst dye protocol to characterize a stem cell or cancer stem cell population see Goodell, et al., Blood, 98(4): 1166-1173 (2001) and Kondo, et al., Proc Natl Acad Sci USA 101:781-786 (2004). In this way, flow cytometry could be used to measure cancer stem cell amount pre- and post-therapy to assess the change in cancer stem cell amount arising from a given therapy or regimen.

In other embodiments using flow cytometry of a sample, the cells in the sample may be treated with a substrate for aldehyde dehydogenase that becomes fluorescent when catalyzed by this enzyme. For instance, the sample can be treated with BODIPY®—aminoacetaldehyde which is commercially available from StemCell Technologies Inc. as Aldefluor®. Cancer stem cells express high levels of aldehyde dehydrogenase relative to bulk cancer cells and therefore become brightly fluorescent upon reaction with the substrate. The cancer stem cells, which become fluorescent in this type of experiment, can then be detected and counted using a standard flow cytometer. In this way, flow cytometry could be used to measure cancer stem cell amount pre- and post-therapy to assess the change in cancer stem cell amount arising from a given therapy or regimen.

In other embodiments, a sample (e.g., a tumor or normal tissue sample, blood sample or bone marrow sample) obtained from the patient is cultured in in vitro systems to assess the cancer stem cell population or amount of cancer stem cells. For example, tumor samples can be cultured on soft agar, and the amount of cancer stem cells can be correlated to the ability of the sample to generate colonies of cells that can be visually counted. Colony formation is considered a surrogate measure of stem cell content, and thus, can be used to quantitate the amount of cancer stem cells. For instance, with hematological cancers, colony-forming assays include colony forming cell (CFC) assays, long-term culture initiating cell (LTC-IC) assays, and suspension culture initiating cell (SC-IC) assays. In this way, the colony-forming or related assay could be used to measure cancer stem cell amount pre- and post-therapy to assess the change in cancer stem cell amount arising from a given therapy or regimen.

In other embodiments, sphere formation is measured to determine the amount of cancer stem cells in a sample (e.g., cancer stem cells form three-dimensional clusters of cells, called spheres) in appropriate media that is conducive to forming spheres. Spheres can be quantitated to provide a measure of cancer stem cells. See Singh, et al., Cancer Res 63: 5821-5828 (2003). Secondary spheres can also be measured. Secondary spheres are generated when the spheres that form from the patient sample are broken apart, and then allowed to reform. In this way, the sphere-forming assay could be used to measure cancer stem cell amount pre- and post-therapy to assess the change in cancer stem cell amount arising from a given therapy or regimen.

In other embodiments, the amount of cancer stem cells in a sample can be determined with a cobblestone assay. Cancer stem cells from certain hematological cancers form "cobblestone areas" (CAs) when added to a culture containing a monolayer of bone marrow stromal cells. For instance, the amount of cancer stem cells from a leukemia sample can be assessed by this technique. The tumor samples are added to the monolayer of bone marrow stromal cells. The leukemia cancer stem cells, more so than the bulk leukemia cells, have the ability to migrate under the stromal layer and seed the formation of a colony of cells which can be seen visually under phase contrast microscopy in approximately 10-14 days as CAs. The number of CAs in the culture is a reflection of the leukemia cancer stem cell content of the tumor sample, and is considered a surrogate measure of the amount of stem cells capable of engrafting the bone marrow of immunodeficient mice. This assay can also be modified so that the CAs can be quantitated using biochemical labels of proliferating cells instead of manual counting, in order to increase the throughput of the assay. See Chung, et al., Blood 105(1):77-84 (2005). In this way, the cobblestone assay could be used to measure cancer stem cell amount pre- and post-therapy to assess the change in cancer stem cell amount arising from a given therapy or regimen.

In other embodiments, a sample (e.g., a tumor or normal tissue sample, blood sample or bone marrow sample) obtained from the patient is analyzed in in vivo systems to determine the cancer stem cell population or amount of cancer stem cells. In certain embodiments, for example, in vivo engraftment is used to quantitate the amount of cancer stem cells in a sample. In vivo engraftment involves implantation of a human specimen with the readout being the formation of tumors in an animal such as in immunocompromised or immunodeficient mice (such as NOD/SCID mice). Typically, the patient sample is cultured or manipulated in vitro and then injected into the mice. In these assays, mice can be injected with a decreasing amount of cells from patient samples, and the frequency of tumor formation can be plotted vs. the amount of cells injected to determine the amount of cancer stem cells in the sample. Alternatively, the rate of growth of the resulting tumor can be measured, with larger or more rapidly advancing tumors indicating a higher cancer stem cell amount in the patient sample. In this way, an in vivo engraftment model/assay could be used to measure cancer stem cell amount pre- and post-therapy to assess the change in cancer stem cell amount arising from a given therapy or regimen.

In certain in vivo techniques, an imaging agent, or diagnostic moiety, is used which binds to molecules on cancer cells or cancer stem cells, e.g., cancer cell or cancer stem cell surface antigens. For instance, a fluorescent tag, radionuclide, heavy metal, or photon-emitter is attached to an antibody (including an antibody fragment) that binds to a cancer stem cell surface antigen. Exemplary cancer stem cell surface antigens are listed above in Table 2. The medical practitioner can infuse the labeled antibody into the patient either prior to, during, or following treatment, and then the practitioner can place the patient into a total body scanner/developer which can detect the attached label (e.g., fluorescent tag, radionuclide, heavy metal, photon-emitter). The scanner/developer (e.g., CT, MRI, or other scanner, e.g. detector of fluorescent label, that can detect the label) records the presence, amount/quantity, and bodily location of the bound antibody. In this manner, the mapping and quantitation of tag (e.g. fluorescence, radioactivity, etc.) in patterns (i.e., different from patterns of normal stem cells within a tissue) within a tissue or tissues indicates the treatment efficacy within the patient's body when compared to a reference control such as the same patient at an earlier time point or a patient or healthy individual who has no detectable cancer. For example, a large signal (relative to a reference range or a prior treatment date, or prior to treatment) at a particular location indicates the presence of cancer stem cells. If this signal is increased relative to a prior date it suggests a worsening of the disease and failure of therapy or regimen. Alternatively, a signal decrease indicates that the therapy or regimen has been effective.

In a specific embodiment, the amount of cancer stem cells is detected in vivo in a subject according to a method comprising the steps of: (a) administering to the subject an effective amount of a labeled cancer stem cell marker binding agent that binds to a cell surface marker found on the cancer stem cells, and (b) detecting the labeled agent in the subject following a time interval sufficient to allow the labeled agent to concentrate at sites in the subject where the cancer stem cell surface marker is expressed. In accordance with this embodiment, the cancer stem cell surface marker-binding agent is administered to the subject according to any suitable method in the art, for example, parenterally (such as intravenously), or intraperitoneally. In accordance with this embodiment, the effective amount of the agent is the amount which permits the detection of the agent in the subject. This amount will vary according to the particular subject, the label used, and the detection method employed. For example, it is understood in the art that the size of the subject and the imaging system used will determine the amount of labeled agent needed to detect the agent in a subject using an imaging means. In the case of a radiolabeled agent for a human subject, the amount of labeled agent administered is measured in terms of radioactivity, for example from about 5 to 20 millicuries of $^{99}$Tc. The time interval following the administration of the labeled agent which is sufficient to allow the labeled agent to concentrate at sites in the subject where the cancer stem cell surface marker is expressed will vary depending on several factors, for example, the type of label used, the mode of administration, and the part of the subject's body that is imaged. In a particular embodiment, the time interval that is sufficient is 6 to 48 hours, 6 to 24 hours, or 6 to 12 hours. In another embodiment the time interval is 5 to 20 days or 5 to 10 days. The presence of the labeled cancer stem cell surface marker-binding agent can be detected in the subject using imaging means known in the art. In general, the imaging means employed depend upon the type of label used. Skilled artisans will be able to determine the appropriate means for detecting a particular label. Methods and devices that may be used include, but are not limited to, computed tomography (CT), whole body scan such as position emission tomography (PET), magnetic resonance imaging (MRI), and sonography. In a specific embodiment, the cancer stem cell surface marker-binding agent is labeled with a radioisotope and is detected in the patient using a radiation responsive surgical instrument (Thurston, et al., U.S. Pat. No. 5,441,050). In another embodiment, the cancer stem cell surface marker-binding agent is labeled with a fluorescent compound and is detected in the patient using a fluorescence responsive scanning instrument. In another embodiment, the cancer stem cell surface marker-binding agent is labeled with a positron emitting metal and is detected in the patient using positron emission-tomography. In yet another embodiment, the cancer stem cell surface marker-binding agent is labeled with a paramagnetic label and is detected in a patient using magnetic resonance imaging (MRI).

Any in vitro or in vivo (ex vivo) assays known to those skilled in the art that can detect and/or quantify cancer stem cells can be used to monitor cancer stem cells in order to evaluate the prophylactic and/or therapeutic utility of a cancer therapy or regimen disclosed herein for cancer or one or more symptoms thereof, or these assays can be used to assess the prognosis of a patient. The results of these assays then may be used to possibly maintain or alter the cancer therapy or regimen.

The amount of cancer stem cells in a specimen can be compared to a predetermined reference range and/or an earlier amount of cancer stem cells previously determined for the subject (either prior to, or during therapy) in order to gauge the subject's response to the treatment regimens described herein. In a specific embodiment, a stabilization or reduction in the amount of cancer stem cells relative to a predetermined reference range and/or earlier cancer stem cell amount previously determined for the subject (prior to, during and/or after therapy) indicates that the therapy or regimen was effective and thus possibly an improvement in the subject's prognosis, whereas an increase relative to the predetermined reference range and/or cancer stem cell amount detected at an earlier time point indicates that the therapy or regimen was ineffective and thus possibly the same or a worsening in the subject's prognosis. The cancer stem cell amount can be used with other standard measures of cancer to assess the prognosis of the subject and/or efficacy of the therapy or regimen: such as response rate, durability of response, relapse-free survival, disease-free survival, progression-free survival, and overall survival. In certain embodiments, the dosage, frequency and/or duration of administration of a therapy is modified as a result of the determination of the amount or change in relative amount of cancer stem cells at various time points which may include prior to, during, and/or following therapy.

The present invention also relates to methods for determining that a cancer therapy or regimen is effective at targeting and/or impairing cancer stem cells by virtue of monitoring cancer stem cells over time and detecting a stabilization or decrease in the amount of cancer stem cells during and/or following the course of the cancer therapy or regimen.

In a certain embodiment, a therapy or regimen may be marketed as an anti-cancer stem cell therapy or regimen based on the determination that a therapy or regimen is effective at targeting and/or impairing cancer stem cells by virtue of having monitored or detected a stabilization or decrease in the amount of cancer stem cells during therapy.

5.10 Methods of Monitoring Cancer Cells

As part of the therapeutically effective regimens of the invention, the amount of cancer cells (alone or in combination with the amount of cancer stem cells) can be monitored/assessed using standard techniques known to one of skill in the art. In certain embodiments of the therapeutically effective regimens of the invention, the regimens result in a stabilization or reduction in the amount (expressed, e.g., as a percentage) of cancer cells in the subject. In one embodiment, the subject undergoing the regimen is monitored to determine whether the regimen has resulted in a stabilization or reduction in the amount (expressed, e.g., as a percentage) of cancer cells in the subject.

In some embodiments, the amount of cancer cells is assessed in a subject using techniques described herein or known to one of skill in the art. In other embodiments, the amount of cancer cells is detected in a sample. Such samples include, but are not limited to, biological samples and samples derived from a biological sample. In certain embodiments, in addition to the biological sample itself or in addition to material derived from the biological sample such as cells, the sample used in the methods of this invention comprises added water, salts, glycerin, glucose, an antimicrobial agent, paraffin, a chemical stabilizing agent, heparin, an anticoagulant, or a buffering agent. In certain embodiments, the biological sample is blood, serum, urine, bone marrow or interstitial fluid. In another embodiment, the sample is a tissue sample. In a particular embodiment, the tissue sample is breast, colon, lung, liver, ovarian, pancreatic, prostate, renal, bone or skin tissue. In a specific embodiment, the tissue sample is a biopsy, including a tumor biopsy. The amount of biological sample taken from the subject will vary according to the type of biological sample and the method of detection to be employed. In a particular embodiment, the biological sample is blood, serum, or urine and the amount of blood, serum, or urine taken from the subject is 0.1 ml, 0.5 ml, 1 ml, 5 ml, 10 ml or more. In another embodiment, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

In accordance with the methods of the invention, a sample derived from a biological sample is one in which the biological sample has been subjected to one or more pretreatment steps prior to the detection and/or measurement of the cancer cell population in the sample. In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeablization, or homogenization followed by centrifugation, filtration, precipitation, dialysis, or chromatography, or by a combination of such pretreatment steps. In certain embodiments, the sample is pretreated by removing cells other than cancer cells from the sample, or removing debris from the sample prior to the determination of the amount of cancer cells in the sample according to the methods of the invention.

The samples for use in the methods of this invention may be taken from any animal subject, preferably a mammal, most preferably a human. The subject from which a sample is obtained and utilized in accordance with the methods of this invention includes, without limitation, an asymptomatic subject, a subject manifesting or exhibiting 1, 2, 3, 4 or more symptoms of cancer, a subject clinically diagnosed as having cancer, a subject predisposed to cancer, a subject suspected of having cancer, a subject undergoing therapy for cancer, a subject that has been medically determined to be free of cancer (e.g., following therapy for the cancer), a subject that is managing cancer, or a subject that has not been diagnosed with cancer.

In certain embodiments, the amount of cancer cells is assessed in a subject or a sample from a subject at least 1, 2, 4, 6, 8, 10, 12, 14, 15, 16, 18, 20, or 30, 60, 90 days 6 months, 9 months, 12 months, >12 months after the subject begins receiving the regimen. In certain embodiments, the amount of cancer cells is assessed after a number of doses (e.g., after 1, 2, 5, 10, 20, 30 or more doses of a therapy). In other embodiments, the amount of cancer cells is assessed after 2 weeks, 1 month, 2 months, 1 year, 2 years, 3 years, 4 years or more after receiving one or more therapies.

The amount of cancer cells in a sample can be expressed as the percentage of, e.g., overall cells in the sample. In some embodiments, the sample is a blood sample or bone marrow sample, wherein the amount of cancer cells per unit of volume (e.g., 1 mL) or other measured unit (e.g., per unit field in the case of a histological analysis) is quantitated. The cancer cell population, in certain embodiments, can be determined as a percentage of the total blood cells.

In other embodiments, the sample from the patient is a tissue sample (e.g., a biopsy from a subject with or suspected or having cancerous tissue), where the amount of cancer cells can be measured, for example, by immunohistochemistry or on the basis of the amount of cancer cells per unit weight of the tissue.

The amount of cancer cells in the test sample can be compared with the amount of cancer cells measured in a reference sample(s) to assess the efficacy of the regimen. In one embodiment, the reference sample is a sample from the subject undergoing therapy, at an earlier time point (e.g., prior to receiving the regimen as a baseline reference sample, or at an earlier time point while receiving the therapy). In this embodiment, the therapy desirably results in a decrease in the amount of cancer cells in the test sample as compared with the reference sample. In another embodiment, the reference sample is obtained from a healthy, subject who has no detectable cancer, or from a patient that is in remission for the same type of cancer. In this embodiment, the therapy desirably results in the test sample having an equal amount of cancer cells as detected in the reference sample (e.g., no detectable cancer cells).

If the reduction in the amount of cancer cells is judged too small, then the medical practitioner has a number of options to adjust the regimen. For instance, the medical practitioner can then either increase the dosage of the therapy administered, the frequency of the administration, the duration of administration, combine the therapy with another therapy(ies), halt the therapy, or any combination thereof.

The amount of cancer cells can be monitored/assessed using standard techniques known to one of skill in the art. Cancer cells can be monitored by, e.g., obtaining a sample, such as a tumor sample, blood sample or bone marrow sample, from a subject and detecting cancer cells in the sample. The amount of cancer cells in a sample (which may be expressed as a percentage) can be assessed by detecting the expression of antigens on cancer cells and/or by detecting the proliferation of cancer cells. Techniques known to those of skilled in the art can be used for measuring these activities. For example, cellular proliferation can be assayed by 3H-thymidine incorporation assays and trypan blue cell counts. Antigen expression can be assayed, for example, by immunoassays including, but are not limited to western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, fluorescence-activated cell sorter (FACS) analysis, flow cytometry and immunofluorescence.

The amount of cancer cells can be compared to a predetermined reference range and/or an earlier amount of cancer cells determined for the subject to gauge the subject's response to the regimens described herein. In a specific embodiment, a reduction in the amount of cancer cells relative to a predetermined reference range and/or earlier cancer cell amount determined for the subject indicate an improvement in the subject's prognosis or response to a therapy, whereas an increase relative to the predetermined reference range and/or earlier cancer cell numbers indicates the same or worse prognosis, or failure to respond to a therapy. In certain embodiments, the dosage, frequency and/or duration of administration of a therapy is modified as a result of the change in the amount of cancer cells.

In some embodiments, the cancer cell population can be monitored/assessed using gross measurements of the cancer cell population. For example, in some embodiments, the cancer cell population is determined using imaging methods such as computed tomography (CT), magnetic resonance imaging (MRI), ultrasound, X-ray imaging, mammography, radionuclide imaging, PET scan, palpitation, direct measurement (e.g. with a ruler) or bone scans.

In embodiments of the invention comprising treatment of solid tumors, the bulk size of the tumor may provide an estimate of the cancer cell population. A number of known methods can be used to assess the bulk size of the tumor. Non-limiting examples of such methods include imaging methods (e.g., computed tomography (CT), magnetic resonance imaging (MRI), PET scans, palpitation, direct measurement (e.g. with a ruler), ultrasound, X-ray imaging, mammography, bone scans and radioisotope imaging), visual methods (e.g., colonoscopy, bronchoscopy, endoscopy), physical examination (e.g., prostate examination, breast examination, lymph nodes examination, abdominal examination, general palpation), blood tests (e.g., prostate specific antigen (PSA) test, carcinoembryonic antigen (CEA) test, cancer antigen (CA)-125 test, alpha-fetoprotein (AFP)), bone marrow analyses (e.g., in cases of hematological malignancies), histopathology, cytology and flow cytometry.

In some embodiments, the bulk tumor size can be measured by assessments based on the size of tumor lesions determined from imaging methods. In specific embodiments, the assessments are performed in accordance with the Response Evaluation Criteria In Solid Tumors (RECIST) Guidelines, which are set forth in Therasse, et al., J Nat Canc Inst 92(3), 205-216 (2000). For instance, in specific embodiments, lesions in the subject that are representative of bulk tumor size are selected so that they are at least=20 mm in their longest diameter at baseline (prior to treatment) when conventional imaging techniques are used (e.g., conventional CT scan, MRI or x-ray) and lesions that are at least =10 mm in their longest diameter at baseline should be selected when spiral CT scanning is used.

5.11 Methods of Monitoring Lymphocyte Cell Count, Neutrophil Cell Count, Platelet Count and Hemoglobin As part of the prophylactically and/or therapeutically effective regimens of the invention, peripheral blood lymphocyte counts can be monitored/assessed using standard techniques known to one of skill in the art. Peripheral blood lymphocyte counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in a subject can be determined by, e.g., separating the lymphocytes from other components of peripheral blood such as plasma using, e.g., Ficoll-Hypaque (Pharmacia) gradient centrifugation. Labeling the T-cells with an antibody directed to a T-cell antigen such as CD3, CD4, and CD8 which is conjugated to a FACS detectable agent, such as FITC or phycoerythrin, and measuring the amount of T-cells by FACS. Further, the effect on a particular subset of T cells (e.g., CD2+, CD4+, CD8+, CD45+, CD45RO+, CD45RA+, or CD8+RA+) or NK cells can be determined using standard techniques known to one of skill in the art, such as FACS.

The subject's absolute neutrophil count (ANC) can be monitored/assessed using standard techniques known to one of skill in the art. In some embodiments, the regimen includes monitoring the patient's ANC in order to avoid the risk of the patient developing neutropenia.

The ANC can be calculated from measurements of the total number of white blood cells (WBC) and the numbers of neutrophils and bands (immature neutrophils). The ANC can be determined manually by trained medical technologists or by automated ANC results obtained from automated hematology analyzers.

The subject's platelet count (PLT) can be monitored/assessed using standard techniques known to one of skill in the art. In some embodiments, the regimen includes monitoring the patient's platelet count in order to avoid the risk of the patient developing thrombocytopenia or becoming blood transfusion dependent. Transfusions can be given as determined by the physician.

The subject's hemoglobin (Hgb) can be monitored/assessed using standard techniques known to one of skill in the art. In some embodiments, the regimen includes monitoring the patient's hemoglobin in order to avoid the risk of the patient developing anemia or becoming transfusion dependent. Transfusions or growth factors (e.g. erythropoietin) can be given as determined by the physician.

5.12 Biological Assays

5.12.1 In Vitro Assays

Antibodies and antibody conjugates of the invention may be characterized in a variety of ways well-known to one of skill in the art. In particular, antibodies or conjugates of the invention may be assayed for the ability to bind to the IL3R alpha chain. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310) (each of these references is incorporated herein in its entirety by reference). Antibodies or conjugates that have been identified to bind to the IL3R alpha chain or a fragment thereof can then be assayed for their specificity and affinity for the IL3R alpha chain.

The antibodies or conjugates may be assayed for specific binding to the IL3R alpha chain and cross-reactivity with other antigens by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 MaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody or conjugate of interest to the cell lysate, incubating for a period of time (e.g., 1 to 4 hours) at 40 C, adding protein A and/or protein G sepharose beads to the cell lysate, incubating for about an hour or more at 40 C, washing the beads in lysis buffer and resuspending the beads in SDS/sample buffer. The ability of the antibody or conjugate of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (e.g., the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of an antibody of the present invention for the IL3R alpha chain and the binding off-rates can be determined from the data by scatchard plot analysis. Competition with a second antibody can also be determined using radioimmunoassays. In this case, the IL3R alpha chain is incubated with an antibody of the present invention conjugated to a labeled compound (e.g., $^3$H or $^{125}$I) in the presence of increasing amounts of an unlabeled second antibody.

In a preferred embodiment, BIAcore kinetic analysis is used to determine the binding on and off rates of antibodies or conjugates to the IL3R alpha chain. BIAcore kinetic analysis comprises analyzing the binding and dissociation of the IL3R alpha chain from chips with immobilized antibodies or conjugates on their surface.

The antibodies, conjugates, pharmaceutical compositions and regimens of the invention can be tested in vitro and/or in vivo for their ability to reduce the quantity, number, amount or percentage of cancer cells and/or cancer stem cells, or inhibit their proliferation. The ability of a conjugate or a regimen of the invention to reduce the quantity, number, amount or percentage of cancer cells, cancer stem cells and/or immune cells (e.g., lymphocytes) or inhibit their proliferation can be assessed by: detecting the expression of antigens on cancer cells, cancer stem cells, and immune cells; detecting the proliferation or viability of cancer cells, cancer stem cells and immune cells; detecting the effector function of cancer cells and cancer stem cells. Techniques known to those of skilled in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, flow cytometry and FACS analysis.

An antibody, antibody conjugate, pharmaceutical composition, or regimen of the invention is preferably tested in vitro and then in vivo for the desired therapeutic or prophylactic activity prior to use in humans. For example, assays which can be used to determine whether administration of a specific antibody or antibody conjugate is indicated include cell culture assays in which a patient tissue sample (e.g., a cancer cell or cancer stem cell) is grown in culture and exposed to, or otherwise contacted with, an antibody or antibody conjugate of the invention, and the effect of such antibody or antibody conjugate upon the tissue sample is observed. The tissue sample can be obtained by biopsy from the patient. This test allows the identification of the therapeutically most effective therapy (e.g., prophylactic or therapeutic agent) for each individual patient.

Determination of cell viability using the XTT assay: In some cases, CD34+ cells are isolated from human cord blood using magnetic beads coated with anti-CD34 antibody. Isolated cells are then counted and aliquoted into 96-well plates and then incubated in the presence of varying concentrations of an antibody or antibody conjugate of the invention. Cell viability it measured by the addition of the XTT colorimetric reagent. Viability is determined by the absorbance of treated cultures at approximately 450-500 nm compared to untreated cultures. In other cases, the cells used in the assay may be a leukemia cell line, such as MV4; 11. The assay can also be used to determine the time course of cell killing by various compounds by performing the XTT assay on cultures that are incubated with the antibody or antibody conjugate for varying periods of time.

Cobblestone assay: The cobblestone area-forming cell (CAFC) assay exploits a reproducible visual end point for the quantitation of cancer stem cells. Leukemia samples are added to adherent cultures of stromal cells, some embodiments MS-5 stromal cells. The cancer stem cells in the culture will migrate below the MS-5 stromal cells and form a colony of cells called a cobblestone that can be visual quantitated. To test the effect of an antibody or antibody conjugate of the invention on the cancer stem cell population using this assay, cells are first cultured in the presence of the drug. In some embodiments the cells are cultured for 16 hours. After this incubation, the cells are added to the stromal cultures. A reduction in the cobblestone area formation in cultures that were treated with the drug compared to the untreated cells represents cancer stem cell activity for the drug.

5.12.2 In Vivo Assays

The antibodies, antibody conjugates, pharmaceutical compositions, and regimens of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapeutic modalities (e.g., prophylactic and/or therapeutic agents), whether such therapeutic modalities are administered separately or as an admixture, and the frequency of administration of the therapeutic modalities.

Animal models for cancer can be used to assess the efficacy of an antibody, antibody conjugate, a combination therapy or pharmaceutical composition of the invention. Examples of animal models for lung cancer include, but are not limited to, lung cancer animal models described by Zhang & Roth (1994, In Vivo 8(5):755-69) and a transgenic mouse model with disrupted p53 function (see, e.g., Morris et al. *J. La. State Med. Soc.* 1998, 150(4):179-85). An example of an animal model for breast cancer includes, but is not limited to, a transgenic mouse that overexpresses cyclin D1 (see, e.g., Hosokawa et al., *Transgenic Res.* 2001, 10(5), 471-8. An example of an animal model for colon cancer includes, but is not limited to, a TCR b and p53 double knockout mouse (see, e.g., Kado et al., *Cancer Res.* 2001, 61(6):2395-8). Examples of animal models for pancreatic cancer include, but are not limited to, a metastatic model of PancO2 murine pancreatic adenocarcinoma (see, e.g., Wang et al., *Int. J. Pancreatol.* 2001, 29(1):37-46) and nu-nu mice generated in subcutaneous pancreatic tumors (see, e.g., Ghaneh et al., *Gene Ther.* 2001, 8(3):199-208). Examples of animal models for non-Hodgkin's lymphoma include, but are not limited to, a severe combined immunodeficiency ("SCID") mouse (see, e.g., Bryant et al., *Lab Invest.* 2000, 80(4), 553-73) and an IgHmu-HOX11 transgenic mouse (see, e.g., Hough et al., *Proc. Natl. Acad. Sci. USA* 1998, 95(23), 13853-8. An example of an animal model for esophageal cancer includes, but is not limited to, a mouse transgenic for the human papillomavirus type 16 E7 oncogene (see, e.g., Herber et al., *J. Virol.* 1996, 70(3):1873-81). Examples of animal models for colorectal carcinomas include, but are not limited to, Apc mouse models (see, e.g., Fodde & Smits, *Trends Mol. Med.* 2001, 7(8):369-73 and Kuraguchi et al., Oncogene 2000, 19(50), 5755-63).

In some embodiments of the invention, the efficacy of the therapeutic regimen in reducing the quantity, number, amount or percentage of cancer stem cells in animals (including humans) undergoing treatment can be evaluated using in vivo techniques. In these embodiments, an imaging agent is used which binds to biological moieties on cancer stem cells, e.g., cancer stem cell surface antigens. For instance, a fluorescent tag or radionuclide is covalently attached to an antibody that binds to a cancer stem cell surface antigen. The medical practitioner can infuse the labeled antibody into the patient either untreated or undergoing treatment, and then the practitioner can place the patient into a total body scanner/developer which can detect the attached label (e.g., fluorescent tag or radionuclide). The scanner/developer (e.g., CT or MRI scanner) records the presence and bodily location of the bound antibody. In this manner, the mapping and quantitation of tag (e.g. fluorescence, radioactivity) in patterns (i.e., different from patterns of normal stem cells within a tissue) within a tissue or tissues indicates the treatment efficacy within the patient's body. For example, a large signal (relative to a reference range or a prior treatment date) at a particular location indicates the presence of cancer stem cells. If this signal is increased relative to a prior treatment date it suggests a worsening of the disease and failure of therapy. Alternatively, a signal decrease indicates that therapy is working.

Similarly, in some embodiments of the invention, the efficacy of the therapeutic regimen in reducing the quantity, number, amount or percentage of cancer cells in animals (including humans) undergoing treatment can be evaluated using in vivo techniques. In one embodiment, the medical practitioner performs the imaging technique with labeled molecule that binds the surface of a cancer cell, e.g., a cancer cell surface antigen. In this manner, the mapping and quantitation of tag (e.g., fluorescence, radioactivity) in patterns within a tissue or tissues indicates the treatment efficacy within the body of the patient undergoing treatment.

In a specific embodiment, the amount of cancer stem cells is detected in vivo in a subject according to a method comprising the steps of: (a) administering to the subject an effective amount of a labeled cancer stem cell marker binding agent that binds to a cell surface marker found on the cancer stem cells, and (b) detecting the labeled agent in the subject following a time interval sufficient to allow the labeled agent to concentrate at sites in the subject where the cancer stem cell surface marker is expressed. In accordance with this embodiment, the cancer stem cell surface marker-binding agent is administered to the subject according to any suitable method in the art, for example, parenterally (e.g. intravenously), or intraperitoneally. In accordance with this embodiment, the effective amount of the agent is the amount which permits the detection of the agent in the subject. This amount will vary according to the particular subject, the label used, and the detection method employed. For example, it is understood in the art that the size of the subject and the imaging system used will determine the amount of labeled agent needed to detect the agent in a subject using imaging. In the case of a radiolabeled agent for a human subject, the amount of labeled agent administered is measured in terms of radioactivity, for example from about 5 to 20 millicuries of 99Tc. The time interval following the administration of the labeled agent which is sufficient to allow the labeled agent to concentrate at sites in the subject where the cancer stem cell surface marker is expressed will vary depending on several factors, for example, the type of label used, the mode of administration, and the part of the subject's body that is imaged. In a particular embodiment, the time interval that is sufficient is 6 to 48 hours, 6 to 24 hours, or 6 to 12 hours. In another embodiment the time interval is 5 to 20 days or 5 to 10 days. The presence of the labeled cancer stem cell surface marker-binding agent can be detected in the subject using imaging means known in the art. In general, the imaging means employed depend upon the type of label used. Skilled artisans will be able to determine the appropriate means for detecting a particular label. Methods and devices that may be used include, but are not limited to, computed tomography (CT), whole body scan such as position emission tomography (PET), magnetic resonance imaging (MRI), fluorescence, chemiluminescence, and sonography. In a specific embodiment, the cancer stem cell surface marker-binding agent is labeled with a radioisotope and is detected in the patient using a radiation responsive surgical instrument (Thurston et al., U.S. Pat. No. 5,441,050). In another embodiment, the cancer stem cell surface marker-binding agent is labeled with a fluorescent compound and is detected in the patient using a fluorescence responsive scanning instrument. In another embodiment, the cancer stem cell surface marker-binding agent is labeled with a positron emitting metal and is detected in the patient using positron emission-tomography. In yet another embodiment, the cancer stem cell surface marker-binding agent is labeled with a paramagnetic label and is detected in a patient using magnetic resonance imaging (MRI).

Further, any assays known to those skilled in the art can be used to evaluate the prophylactic and/or therapeutic utility of an antibody, antibody conjugate or pharmaceutical composition disclosed herein for cancer or one or more symptoms thereof.

5.12.3 Assessing Toxicity

The toxicity and/or efficacy of antibodies, antibody conjugates, pharmaceutical compositions, and regimens of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic regimens that exhibit large therapeutic indices are preferred. While therapeutic regimens that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the therapies for use in humans. The dosage of such agents lies preferably within a range of circulating concentrations that include the $ED_{50}$ with little or no toxicity to normal tissues. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the $IC_{50}$ (i.e., the concentration of the test antibody or test antibody conjugate that achieves a half-maximal inhibition of symptoms) as determined in cell culture. Such information can be used to more accurately determine useful doses in humans. Levels of antibodies or antibody conjugates in plasma may be measured, for example, by high performance liquid chromatography.

5.13 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. The pharmaceutical product may contain, for example, a conjugate of the invention in a unit dosage form in a first container, and in a second container, sterile water for injection. Alternatively, the unit dosage form may be a solid suitable for oral, transdermal, intranasal, or topical delivery.

In a specific embodiment, the unit dosage form is suitable for intravenous, intramuscular, intranasal, oral, topical or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disorder in question. In other words, the article of manufacture includes instruction means indicating or suggesting a dosing regimen including, but not limited to, actual doses, monitoring procedures, cancer cell counts, cancer stem cell counts, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises an antibody conjugate of the invention, and wherein said packaging material includes instruction means which indicate that said antibody conjugate can be used to prevent, manage, treat, and/or ameliorate one or more symptoms associated with cancer, or one or more symptoms thereof by administering specific doses and using specific dosing regimens as described herein.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises antibody of the invention, and wherein said packaging material includes instruction means which indicate that said antibody can be used to prevent, manage, treat, and/or ameliorate one or more symptoms associated with cancer, or one or more symptoms thereof by administering specific doses and using specific dosing regimens as described herein.

In specific embodiments, the article of manufacture include labeled antibodies that selectively or bind to stem cells, and preferably, that selectively or bind to cancer stem cells. As such, the article contains a method to adjust the dosages used in the therapeutic regimens, and to monitor the efficacy of the therapeutic regimen.

5.14 Bone Marrow Purging

The present invention provides a method for purging bone marrow or peripheral blood prior to autologous stem cell transplant, comprising contacting ex vivo bone marrow or peripheral blood obtained from a human with a composition comprising an amount of an antibody conjugate of the invention for a time sufficient to purge the bone marrow or peripheral blood of cells expressing an alpha subunit of the IL-3 receptor alpha subunit. In certain embodiments of the invention, the antibodies and antibody conjugates (including those described in Section 5.3 and 5.4, infra) can be used to purge the bone marrow or peripheral blood. In an aspect of this embodiment, the number of bone marrow or peripheral blood cells expressing an alpha subunit of the IL-3 receptor alpha subunit after contacting with a conjugate of the invention is decreased by at least 75%, 80%, 90%, 95%, or by at least 99% relative to a negative control.

The present invention provides a method for performing an autologous bone marrow or peripheral blood stem cell transplant, comprising administering to a human an amount of purged bone marrow or peripheral blood effective to reconstitute hematopoietic function in said human, wherein said purged bone marrow or peripheral blood is bone marrow or peripheral blood obtained from said human previously contacted with an amount of an antibody conjugate of the invention for a time sufficient to purge the bone marrow or peripheral blood of cells expressing an alpha subunit of the IL-3 receptor alpha subunit. Further, the present invention provides a composition comprising purged bone marrow or peripheral blood, wherein said purged bone marrow or peripheral blood is bone marrow or peripheral blood obtained from a human and contacted ex vivo with an amount of an antibody conjugate of the invention for a time sufficient to purge the bone marrow or peripheral blood of cells expressing an alpha subunit of the IL-3 receptor alpha subunit. In one aspect, the composition can further comprise a pharmaceutically acceptable carrier.

6. EXAMPLE

The following example is illustrative, and should not be viewed as limiting the scope of the present invention. Reasonable variations, such as those that occur to a reasonable artisan, can be made herein without departing from the scope of the present invention

6.1 Materials and Methods

Cells

Hybridoma cells of the monoclonal antibodies 26292, 32701, and 32716 were obtained from StemLine Therapeutics, Inc. (New York, N.Y.) and grown in DMEM medium with 10% FBS. TF-1 was obtained from American Type Culture Collection (ATCC) and grown in RPMI 1640 medium with 10% FBS and 2 ng/ml GM-CSF. Molm-13 and Molm-14 were provided by Dr. Robert J. Arceci (Kimmel Comprehensive Cancer Center, Johns Hopkins University)

and grown in RPMI 1640 medium with 10% FBS. ML-1 was obtained from the National Cancer Institute and grown in IMDM with 10% FBS. U937 was grown in RPMI 1640 medium with 10% FBS.

Construction and Purification of scFv-PE38 Immunotoxin

Total cellular RNA was isolated from hybridoma cells using the Qiagen RNeasy mini kit. $V_H$ and $V_L$ cDNAs of the monoclonal antibodies were obtained by a RACE method using SMART RACE cDNA amplification kit (Clontech) as described in Pastan I, Beers R, Bera T K. Recombinant immunotoxins in the treatment of cancer. *Methods Mol Biol* 2004; 248:503-18. The prepared cDNAs were used as the template for PCR reactions for $V_H$ and $V_L$. The PCR products were cloned into the pCR4®-TOPO® vector using the TOPO TA cloning kit (Invitrogen). Five independent clones for each chain were sequenced to exclude the possibility of PCR error. The obtained sequences were confirmed again by comparing sequences in GenBank. Then the $V_H$ and $V_L$ were assembled into a single chain Fv (scFv) and fused to PE38. The expression and purification of scFv-PE38 was conducted as described in Pastan et al, above. 26292(Fv)-PE38-KDEL was constructed by replacing the PE38 portion from the expression plasmid with PE38 containing KDEL at the carboxyl terminus in the expression plasmid. See Kreitman R J, Margulies I, Stetler-Stevenson M, et al. Cytotoxic activity of disulfide-stabilized recombinant immunotoxin RFB4(dsFv)-PE38 (BL22) toward fresh malignant cells from patients with B-cell leukemias. *Clin Cancer Res* 2000; 6:1476-87.

FACS Analysis

FACS analysis was performed to measure the binding of the monoclonal antibodies or immunotoxins to CD123 expressing cells. For screening monoclonal antibodies with good binding affinity, $2.5 \times 10^5$ TF-1 cells were incubated with 0.5 µg/ml of the anti-CD123 monoclonal antibodies or MOPC 21 isotype control IgG$_1$ (Sigma) in 200 µl of PBS containing 5% FBS and 0.1% sodium azide. After incubation for 1 hour at 4° C., the cells were washed twice with the same buffer and incubated with R-PE labeled goat F(ab')$_2$ anti-mouse IgG (BioSource). After washing, the cells were suspended in 0.5 ml of the buffer, and the fluorescence associated with the live cells was measured using a FACSCalibur instrument (BD Biosciences).

For cell staining using immunotoxins, $2.5 \times 10^5$ cells were incubated with different concentrations of immunotoxins for 1 hour at 4° C., followed by a rabbit anti-PE38 polyclonal antibody. The PE38 was detected with R-PE-labeled goat F(ab')$_2$ anti-rabbit IgG (BioSource). For sequential binding in competition assays, the first immunotoxin was incubated with TF-1 for 1 hour, followed by the second immunotoxin for an additional hour.

To evaluate CD123 expression on various leukemia cell lines, $2.5 \times 10^5$ cells were incubated with 10 µg/ml of R-PE labeled 9F5 (BD Pharmingen) or R-PE labeled isotype control IgG$_1$ (Sigma) for 1 hour at 4° C. QuantiBRITE PE Beads (BD Biosciences) was used as a PE fluorescence standard. See Pannu K K, Joe E T, Iyer S B. Performance evaluation of QuantiBRITE phycoerythrin beads. *Cytometry* 2001; 45:250-8.

Cytotoxicity Assay

Cytotoxicity on cell lines was measured by cell viability assay. Cells were seeded into 96 well plates at a concentration of $2 \times 10^4$ cells/well. Serial dilutions of immunotoxins in 0.2% human serum albumin (HSA) were added to the cells, resulting in final concentrations ranging from 0.1 to 1000 ng/ml in 150 µl. After incubation for 48 hours, 10 µl of WST-8 (Dojindo Molecular Technologies) was added to each well, and the incubation was carried out for 4 hours at 37° C. The absorbance of the sample at 450 nm was measured with a reference wavelength of 650 nm. Cytotoxicity is defined by IC$_{50}$, 50% inhibition of cell viability, which is midway between the level of viability in the absence of toxin and that in the presence of 10 µg/ml of cycloheximide. All experiments were performed in triplicate. For stability assays, 200 ng/ml of 26292(Fv)-PE38 in HSA was incubated at 4° C. or 37° C. for varying times before evaluation in the cytotoxicity assay.

6.2 Results

Screening Antibodies with High Affinity CD123

Seven anti-CD123 monoclonal antibodies were analyzed by flow cytometry for their binding to CD123 on the surface of TF-1, a CD123-expressing leukemia cell line. In these studies, a concentration of 0.5 µg/ml (~3 nM) was used, to distinguish between high and low binders. As shown in FIG. 6A, monoclonal antibodies 26292, 32701, and 32716 had the highest fluorescence intensity and were the best binders in the panel.

Total RNA from the hybridoma cells (26292, 32701, and 32716) was prepared and used for cDNA amplification to clone the heavy and light chain Fvs. After sequencing confirmation, the Fvs of the $V_H$ and $V_L$ were linked together and cloned into an expression vector to construct the scFv-PE38 recombinant immunotoxin ($V_H$-linker-$V_L$-PE38) as described in Pastan et al above. Each immunotoxin was expressed in *E. coli* and purified to near 95% homogeneity as indicated by SDS-PAGE analysis (FIG. 6B). The yields ranged from 2%-5% based on the amount of inclusion body protein used as the starting material.

Binding Ability, Cytotoxic Activity and Stability of Anti-CD123 Immunotoxins

Purified immunotoxins were incubated with TF-1 to test their binding to CD123 by flow cytometry (FIG. 7A). SS1P, an immunotoxin targeting (see Hassan R, Bera T, Pastan I. Mesothelin: a new target for immunotherapy. *Clin Cancer Res* 2004; 10:3937-42), which is not expressed on the surface of TF-1, was used as a negative control. After subtracting the background SS1P value, the median fluorescence intensities (MFIs) of 26292(Fv)-PE38, 32701(Fv)-PE38, and 32716(Fv)-PE38 were 39.7, 18.9, and 33.5, respectively, indicating that 26292(Fv)-PE38, 32701(Fv)-PE38, and 32716(Fv)-PE38 bind specifically to TF-1. The apparent affinities of 26292(Fv)-PE38, 32701(Fv)-PE38, and 32716(Fv)-PE38 on TF-1 determined by flow cytometry were 3.5 nM, 8.2 nM and 1.4 nM, respectively, showing that these immunotoxins can bind TF-1 with high affinities. Typical data with immunotoxin 26292(Fv)-PE38 is shown in FIG. 7B.

Cytotoxicity of these immunotoxins was tested on TF-1 (FIG. 7C). 26292(Fv)-PE38 had the best activity with an IC$_{50}$=200 ng/ml. The average IC$_{50}$s from nine independent assays was 185 ng/ml. 32701(Fv)-PE38 and 32716(Fv)-PE38 had lower activity and did not reach an IC$_{50}$ at 1000 ng/ml, where a 25% decrease in cell viability was observed. Because 26292(Fv)-PE38 and 32716(Fv)-PE38 had similar binding abilities for CD123 (FIG. 7A and affinity data), it was surprising to find that their cytotoxic activities were so different. The possibility that these immunotoxins bound to different epitopes on CD123, which affected their ability to kill cells, was tested: Competition assays, in which cells were incubated with an excess of one immunotoxin followed by an excess of the second, were carried out. If two immunotoxins bound to an overlapping epitope, the fluorescence signal from the combination would be close to that of a single immunotoxin, whereas if two immunotoxins bound to different epitopes, the fluorescence signal from the combination would be close to the sum of two individual values.

The results of these experiments are shown in Table 3. When immunotoxins 32701(Fv)-PE38 and 32716(Fv)-PE38 were combined sequentially, the fluorescent signal was close to that of the first immunotoxin added. In contrast, when 26292(Fv)-PE38 was combined with either 32701(Fv)-PE38 or 32716(Fv)-PE38, the fluorescence was close to the sum of the two individual immunotoxins. These data indicate that immunotoxins 32701(Fv)-PE38 and 32716(Fv)-PE38 bind to an overlapping epitope on CD123, whereas 26292(Fv)-PE38 binds to a different epitope. Similar results using monoclonal antibodies instead of immunotoxins were obtained (data not shown).

To be useful in therapy, an immunotoxin must be stable for several hours at 37° C. in the circulation. Several single chain immunotoxins have been found to be unstable at 37° C. and disulfide bonded variants have been produced to overcome this difficulty. See Reiter Y, Brinkmann U, Lee B, et al. Engineering antibody Fv fragments for cancer detection and therapy: disulfide-stabilized Fv fragments. Nat Biotechnol 1996; 14:1239-45. To assess the stability of the most active immunotoxin, 26292(Fv)-PE38 was incubated at 37° C. or 4° C. for 1, 3, and 6 hours (FIG. 7D). After incubation at 37° C. for 6 hours, there was no change in the activity of 26292(Fv)-PE38, showing that this immunotoxin is stable at a physiological temperature.

TABLE 3

Competition binding assay

| 1$^{st}$ IT[1] | 2$^{nd}$ IT | MFT[2] observed (Mean + S.D.) | MFI-1$^{st}$ IT if two ITs have competition | MFT = 1$^{st}$ + 2$^{nd}$ if two ITs have no competition |
|---|---|---|---|---|
| 26292 | / | 71.2 + 5.3 | / | / |
| 32701 | / | 17.2 + 5.3 | / | / |
| 32716 | / | 50.6 + 0.7 | / | / |
| 32701 | 32716 | 28.8 + 3.5 | 17.2 | 67.8 |
| 32701 | 26292 | 84.8 + 3.0 | 17.2 | 88.4 |
| 32716 | 32701 | 50.3 + 1.8 | 50.6 | 67.8 |
| 32716 | 26292 | 95.4 + 2.0 | 50.6 | 121.8 |

60 nM of immunotoxin were added to TF-1 either alone or Sequentially by another immunotoxin as indicated. Data are from Three independent assays.
[1]IT, immunotoxin
[2]MFI, median fluorescence intensities CD123 Expression and Cytotoxicity of 26292 on Leukemia Cell Lines It is well established that antigen density on the cell surface of target cells plays an important role in the sensitivity of cells to immunotoxins. See Alexander R L, Kucera G L, Klein B, et al. In vitro interleukin-3 binding to leukemia cells predicts cytotoxicity of a diphtheria toxin/IL-3 fusion protein. Bioconjug Chem 2000; 11:564-8; Alexander R L, Ramage J, Kucera G L, et al. High affinity IL-3 receptor alpha subunit expression on blasts from patients with acute myelogenous leukemia correlates with cytotoxicity of a diphtheria toxin/IL-3 fusion protein. Leuk Res 2001; 25:875-81; and Kreitman R J, Margulies I, Stetler-Stevenson M, et al. Cytotoxic activity of disulfide-stabilized recombinant immunotoxin RFB4(dsFv)-PE38 (BL22) toward fresh malignant cells from patients with B-cell leukemias. Clin Cancer Res 2000; 6:1476-87. Therefore, CD123 expression levels on several AML cell lines was assessed by flow cytometry using QuantiBRITE standard PE beads (FIG. 8). For TF-1, 6900 CD123 sites were detected per cell, 9900 on Molm-13, 13900 on Molm-14, and 1900 on ML-1 were detected. No expression on U937 was detected.

Because these cell lines all had low to moderate CD123 expression, a more active derivative of 26292(Fv)-PE38 was produced by replacing the REDLK sequence at its carboxyl terminus with KDEL. The mutation of REDLK to KDEL has been reported to improve the cytotoxicity of immunotoxins toward a variety of antigens. See Kreitman R J, Margulies I, Stetler-Stevenson M, et al. Cytotoxic activity of disulfide-stabilized recombinant immunotoxin RFB4(dsFv)-PE38 (BL22) toward fresh malignant cells from patients with B-cell leukemias. Clin Cancer Res 2000; 6:1476-87; Kreitman R J, Pastan I. Importance of the glutamate residue of KDEL in increasing the cytotoxicity of Pseudomonas exotoxin derivatives and for increased binding to the KDEL receptor. Biochem J 1995; 307:29-37; and Seetharam S, Chaudhary V K, FitzGerald D, et al. Increased cytotoxic activity of Pseudomonas exotoxin and two chimeric toxins ending in KDEL. J Biol Chem 1991; 266:17376-81. The cytotoxicity of 26292(Fv)-PE38 and 26292(Fv)-PE38-KDEL was determined on these cell lines (FIG. 9). HB21 (Fv)-PE40, an immunotoxin targeting the transferrin receptor (highly expressed on most cancer cells; see Batra J K, Fitzgerald D J, Chaudhary V K, et al. Single-chain immunotoxins directed at the human transferrin receptor containing Pseudomonas exotoxin A or diphtheria toxin: anti-TFR (Fv)-PE40 and DT388-anti-TFR(Fv). Mol Cell Biol 1991; 11:2200-5), was used as a positive control to be sure the cells were sensitive to PE-based immunotoxins. Results of these assays are summarized in Table 4.

TABLE 4

Summary of CD123 expression on AML cell lines and cytotoxicity of 26292 immunotoxin

| | | IC$_{50}$ (ng/ml) | | |
|---|---|---|---|---|
| AML cell lines | CD123 sites per cell | 26292(Fv)-PE38 | 26292(Fv)-PE38-KDEL | HB21(Fv)-PE40 |
| TF-1 | 6,900 | 200 | 38 | 2.2 |
| Molm-13 | 9,900 | 200 | 30 | 20 |
| Molm-14 | 13,900 | >1,000 | 200 | 60 |
| ML-1 | 1,900 | >1,000 | 1,000 | 5.2 |
| U937 | 0 | >1,000 | 1,000 | 0.9 |

For all of the cell lines expressing CD123, the activity of the immunotoxin was increased using the mutant immunotoxin containing KDEL; in U937, with no immunotoxin. In two of three cell lines with moderate CD123 expression (TF-1 and Molm-13), the KDEL variant was more active with IC$_{50}$s falling from 200 ng/ml to 38 and 30 ng/ml, respectively. Molm-14 was less sensitive to the immunotoxins against CD123. The ML-1 cell line had very low CD123 expression and was resistant to the immunotoxin targeting CD123.

This example has described the production of three IL3Rα-cytotoxin conjugates that target IL3Rα and their activities on IL3Rα-expressing cell lines.

7. EQUIVALENTS

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

I claim:

1. A nucleic acid that encodes a single chain fragment variable (scFv) region of an antibody that binds CD123, wherein said nucleic acid comprises nucleotide sequences that encode the complementarity determining regions (CDRs) of the variable heavy (VH) domain and the variable light (VL) domain of said antibody, and wherein said CDRs comprise the VH domain CDR1 presented in SEQ ID NO: 33, the VH domain CDR2 presented in SEQ ID NO: 34, the VH domain CDR3 presented in SEQ ID NO: 35, the VL domain CDR1 presented in SEQ ID NO: 38, the VL domain CDR2 presented in SEQ ID NO: 39, and the VL domain CDR3 presented in SEQ ID NO: 40.

2. The nucleic acid of claim 1, wherein said nucleotide sequence that encodes the CDRs of the VH domain of said antibody comprises SEQ ID NO: 31.

3. The nucleic acid of claim 1, wherein said nucleotide sequence that encodes the CDRs of the VL domain of said antibody comprises SEQ ID NO: 36.

4. The nucleic acid of claim 1, wherein said nucleotide sequence that encodes the CDRs of the VH domain of said antibody comprises SEQ ID NO: 31 and wherein said nucleotide sequence that encodes the CDRs of the VL domain of said antibody comprises SEQ ID NO: 36.

5. The nucleic acid of claim 1, wherein said nucleic acid encodes a fusion protein, said fusion protein comprising said anti-CD123 scFv antibody region and a second protein.

6. An expression vector comprising the nucleic acid of claim 5.

7. The expression vector of claim 6, wherein said expression vector is a viral vector.

8. An isolated mammalian cell comprising the expression vector of claim 6.

9. An isolated mammalian cell engineered to express the nucleic acid of claim 5.

10. The mammalian cell of claim 9, wherein said mammalian cell is a human cell.

11. The nucleic acid of claim 5, wherein said second protein is *Pseudomonas* exotoxin A.

12. The nucleic acid of claim 5, wherein said second protein is abrin, ricin A, cholera toxin, diphtheria toxin, tumor necrosis factor, α-interferon, nerve growth factor, platelet derived growth factor, tissue plasminogen activator, an apoptotic agent, a thrombotic agent, an anti-angiogenic agent, angiostatin, endostatin, a lymphokine, interleukin-1, interleukin-2, interleukin-6, granulocyte macrophage colony stimulating factor, and granulocyte colony stimulating factor, or a growth factor.

13. An expression vector comprising the nucleic acid of claim 1.

14. The expression vector of claim 13, wherein said expression vector is a viral vector.

15. An isolated mammalian cell comprising the expression vector of claim 13.

16. An isolated mammalian cell engineered to express the nucleic acid of claim 1.

17. The mammalian cell of claim 16, wherein said mammalian cell is a human cell.

18. A nucleic acid that encodes an anti-CD123 single chain fragment variable (scFv) antibody region, wherein said nucleic acid comprises SEQ ID NO: 31 and SEQ ID NO: 36.

19. The nucleic acid of claim 18, wherein said nucleic acid encodes a fusion protein, said fusion protein comprising said anti-CD123 scFv antibody region and a second protein.

20. An expression vector comprising the nucleic acid of claim 19.

21. The expression vector of claim 20, wherein said expression vector is a viral vector.

22. An isolated mammalian cell comprising the expression vector of claim 20.

23. An isolated mammalian cell engineered to express the nucleic acid of claim 19.

24. The mammalian cell of claim 23, wherein said mammalian cell is a human cell.

25. The nucleic acid of claim 19, wherein said second protein is *Pseudomonas* exotoxin A.

26. The nucleic acid of claim 19, wherein said second protein is abrin, ricin A, cholera toxin, diphtheria toxin, tumor necrosis factor, α-interferon, nerve growth factor, platelet derived growth factor, tissue plasminogen activator, an apoptotic agent, a thrombotic agent, an anti-angiogenic agent, angiostatin, endostatin, a lymphokine, interleukin-1, interleukin-2, interleukin-6, granulocyte macrophage colony stimulating factor, and granulocyte colony stimulating factor, or a growth factor.

27. An expression vector comprising the nucleic acid of claim 18.

28. The expression vector of claim 27, wherein said expression vector is a viral vector.

29. An isolated mammalian cell comprising the expression vector of claim 27.

30. An isolated mammalian cell engineered to express the nucleic acid of claim 18.

31. The mammalian cell of claim 30, wherein said mammalian cell is a human cell.

32. A nucleic acid that encodes the variable heavy (VH) domain of monoclonal antibody 32716, wherein said VH domain comprises SEQ ID NO: 32.

33. The nucleic acid of claim 32, wherein said nucleic acid comprises SEQ ID NO: 31.

34. The nucleic acid of claim 33, wherein said nucleic acid further comprises a nucleic acid sequence that encodes the variable light (VL) domain of monoclonal antibody 32716, wherein said VL domain comprises SEQ ID NO: 37.

35. The nucleic acid of claim 34, wherein said nucleic acid sequence that encodes the VL domain of monoclonal antibody 32716 comprises SEQ ID NO: 36.

36. A nucleic acid that encodes the variable light (VL) domain of monoclonal antibody 32716, wherein said VL domain comprises SEQ ID NO: 37.

37. The nucleic acid of claim 36, wherein said nucleic acid comprises SEQ ID NO: 36.

* * * * *

SEQUENCE LISTING

```
<160> NUMBER OF SEQ ID NOS: 42

<210> SEQ ID NO 1
<211> LENGTH: 354
<212> TYPE: DNA
<213> ORGANISM: Artificial Sequence
<220> FEATURE:
<223> OTHER INFORMATION: 26292 VH

<400> SEQUENCE: 1
cagatccagt tggtgcagtc tggacctgag ctgaagaagc ctggagagac agtcaagatc      60
tcctgcaaga cttctggata tgtcttcaca aactatgaa tgaactgggt gaaacaggct     120
ccaggaaagg gtttcaagtg gatgggctgg atgaacacca acactggaga gccaacatct     180
cttgaagact tcaagggacg gtttgccttc tctttggaaa cctctgccag cactgcctat     240
ttgcagatca acaacctcaa aaatgacgac acggctacat atttctgtgc aagatcgggg     300
ggttacgacc ccatggacta ctggggtcaa ggaacctcag tcaccgtctc ctca           354

<210> SEQ ID NO 2
<211> LENGTH: 115
<212> TYPE: PRT
<213> ORGANISM: Artificial Sequence
<220> FEATURE:
<223> OTHER INFORMATION: 26292 VH

<400> SEQUENCE: 2

Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Thr Phe Thr Ser Tyr
                20                  25                  30

Trp Met Asn Trp Val Lys Gln Arg Pro Asp Gln Gly Leu Glu Trp Ile
            35                  40                  45

Gly Arg Ile Asp Pro Tyr Asp Ser Glu Thr His Tyr Asn Gln Lys Phe
        50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
                100                 105                 110

Val Ser Ser
        115

<210> SEQ ID NO 3
<211> LENGTH: 5
<212> TYPE: PRT
<213> ORGANISM: Artificial Sequence
<220> FEATURE:
<223> OTHER INFORMATION: 26292 VH CDR1

<400> SEQUENCE: 3
```

Ser Tyr Trp Met Asn
1               5

<210> SEQ ID NO 4
<211> LENGTH: 18
<212> TYPE: PRT
<213> ORGANISM: Artificial Sequence
<220> FEATURE:
<223> OTHER INFORMATION: 26292 VH CDR2

<400> SEQUENCE: 4

Gly Arg Ile Asp Pro Tyr Asp Ser Glu Thr His Tyr Asn Gln Lys Phe
1               5                   10                  15

Lys Asp

<210> SEQ ID NO 5
<211> LENGTH: 6
<212> TYPE: PRT
<213> ORGANISM: Artificial Sequence
<220> FEATURE:
<223> OTHER INFORMATION: 26292 VH CDR3

<400> SEQUENCE: 5

Gly Asn Trp Asp Asp Tyr
1               5

<210> SEQ ID NO 6
<211> LENGTH: 321
<212> TYPE: DNA
<213> ORGANISM: Artificial Sequence
<220> FEATURE:
<223> OTHER INFORMATION: 26292 VL

<400> SEQUENCE: 6
gatgtccaga taacccagtc tccatcttat cttgctgcat ctcctggaga aaccattact      60
attaattgca gggcaagtaa gagcattagc aaagatttag cctggtatca agagaaacct     120
gggaaaacta ataagcttct tatctactct ggatccactt tgcaatctgg aattccatca     180
aggttcagtg gcagtggatc tggtacagat ttcactctca ccattagtag cctggagcct     240
gaagattttg caatgtatta ttgtcaacaa cataataaat atccgtacac gttcggaggg     300
gggaccaagc tggaaataaa a                                                321

<210> SEQ ID NO 7
<211> LENGTH: 107
<212> TYPE: PRT
<213> ORGANISM: Artificial Sequence
<220> FEATURE:
<223> OTHER INFORMATION: 26292 VL

<400> SEQUENCE: 7

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys
            100                 105

<210> SEQ ID NO 8
<211> LENGTH: 11
<212> TYPE: PRT
<213> ORGANISM: Artificial Sequence
<220> FEATURE:
<223> OTHER INFORMATION: 26292 VL CDR1

<400> SEQUENCE: 8

Arg Ala Ser Lys Ser Ile Ser Lys Asp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: 26292 VL CDR2

<400> SEQUENCE: 9

Ser Gly Ser Thr Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: 26292 VL CDR3

<400> SEQUENCE: 10

Gln Gln His Asn Lys Tyr Pro Tyr Thr
1               5

<210> SEQ ID NO 11
<211> LENGTH: 354
<212> TYPE: DNA
<213> ORGANISM: Artificial Sequence
<220> FEATURE:
<223> OTHER INFORMATION: 32703 VH

<400> SEQUENCE: 11
caggtccaac tgcagcagcc tggggctgaa cttgtgaagc ctggggctcc agtgaagctg      60
tcctgcaagg cttctggcta caccttcacc aactactgga tgaactggat taaacagagg     120
cctggacgag gcctcgagtg gattggaagg attgatccct ccgatagtga agtcactac     180 aatcaaaagt tcaaggacaa ggccacactg actgttgaca atcctccaa tacagcctac     240 atccaactca gcagtctgac atctgaggac tctgcggtct attactgtgc aagatatgat     300
tacgacgata ctatggacta ctggggtcaa ggaacctcag tcaccgtctc ctca           354

<210> SEQ ID NO 12
<211> LENGTH: 118
<212> TYPE: PRT
<213> ORGANISM: Artificial Sequence
<220> FEATURE:
<223> OTHER INFORMATION: 32703 VH

<400> SEQUENCE: 12

Gln Val Gln Leu Gln Gln Pro Gly Ala Glu Leu Val Lys Pro Gly Ala
1               5                   10                  15

```
Pro Val Lys Leu Ser Cys Lys Ala Ser Gly Tyr Thr Phe Thr Asn Tyr
            20                  25                  30

Trp Met Asn Trp Ile Lys Gln Arg Pro Gly Arg Gly Leu Glu Trp Ile
        35                  40                  45

Gly Arg Ile Asp Pro Ser Asp Ser Glu Ser His Tyr Asn Gln Lys Phe
    50                  55                  60

Lys Asp Lys Ala Thr Leu Thr Val Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Tyr Asp Tyr Asp Asp Thr Met Asp Tyr Trp Gly Gln Gly Thr
            100                 105                 110

Ser Val Thr Val Ser Ser
        115
```

<210> SEQ ID NO 13
<211> LENGTH: 5
<212> TYPE: PRT
<213> ORGANISM: Artificial Sequence
<220> FEATURE:
<223> OTHER INFORMATION: 32703 VH CDR1

<400> SEQUENCE: 13

```
Asn Tyr Trp Met Asn
1               5
```

<210> SEQ ID NO 14
<211> LENGTH: 17
<212> TYPE: PRT
<213> ORGANISM: Artificial Sequence
<220> FEATURE:
<223> OTHER INFORMATION: 32703 VH CDR2

<400> SEQUENCE: 14

```
Arg Ile Asp Pro Ser Asp Ser Glu Ser His Tyr Asn Gln Lys Phe Lys
1               5                   10                  15

Asp
```

<210> SEQ ID NO 15
<211> LENGTH: 9
<212> TYPE: PRT
<213> ORGANISM: Artificial Sequence
<220> FEATURE:
<223> OTHER INFORMATION: 32703 VH CDR3

<400> SEQUENCE: 15

```
Tyr Asp Tyr Asp Asp Thr Met Asp Tyr
1               5
```

<210> SEQ ID NO 16
<211> LENGTH: 336
<212> TYPE: DNA
<213> ORGANISM: Artificial Sequence
<220> FEATURE:
<223> OTHER INFORMATION: 32703 VL

<400> SEQUENCE: 16

```
gatattgtga tgactcaggc tgcaccctct gtccctgtca ctcctggaga gtccgtatcc      60
atctcctgca ggtctaataa gagtctcctg catagtaatg caacactta cttgtattgg     120 ttcctgcaga ggccaggcca gtctcctcag ctcctgatat atcggatgtc caaccttgcc    180
```

```
tcaggagtcc cagacaggtt cagtggcagt gggtcaggaa ctgctttcac actgagaatc    240
agtagagtgg aggctgagga tgtgggtgtt tattactgta tgcaacatct agaatatccg    300
tacacgttcg gagggggac caagctggaa ataaaa                               336
```

```
<210> SEQ ID NO 17
<211> LENGTH: 112
<212> TYPE: PRT
<213> ORGANISM: Artificial Sequence
<220> FEATURE:
<223> OTHER INFORMATION: 32703 VL

<400> SEQUENCE: 17
```

Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

```
<210> SEQ ID NO 18
<211> LENGTH: 16
<212> TYPE: PRT
<213> ORGANISM: Artificial Sequence
<220> FEATURE:
<223> OTHER INFORMATION: 32703 VL CDR1

<400> SEQUENCE: 18
```

Arg Ser Asn Lys Ser Leu Leu His Ser Asn Gly Asn Thr Tyr Leu Tyr
1               5                   10                  15

```
<210> SEQ ID NO 19
<211> LENGTH: 7
<212> TYPE: PRT
<213> ORGANISM: Artificial Sequence
<220> FEATURE:
<223> OTHER INFORMATION: 32703 VL CDR2

<400> SEQUENCE: 19
```

Arg Met Ser Asn Leu Ala Ser
1               5

```
<210> SEQ ID NO 20
<211> LENGTH: 9
<212> TYPE: PRT
<213> ORGANISM: Artificial Sequence
<220> FEATURE:
<223> OTHER INFORMATION: 32703 VL CDR3

<400> SEQUENCE: 20
```

Met Gln His Leu Glu Tyr Pro Tyr Thr
1               5

```
<210> SEQ ID NO 21
<211> LENGTH: 354
```

<212> TYPE: DNA
<213> ORGANISM: Artificial Sequence
<220> FEATURE:
<223> OTHER INFORMATION: 32701 VH

<400> SEQUENCE: 21

```
cagatccagt tggtgcagtc tggacctgag ctgaagaagc ctggagagac agtcaagatc      60
tcctgcaaga cttctggata tgtcttcaca aactatggaa tgaactgggt gaaacaggct     120
ccaggaaagg gtttcaagtg gatgggctgg atgaacacca acactggaga gccaacatct     180
cttgaagact tcaagggacg gtttgccttc tctttggaaa cctctgccag cactgcctat     240
ttgcagatca acaacctcaa aaatgacgac acggctacat atttctgtgc aagatcgggg     300
ggttacgacc ccatggacta ctggggtcaa ggaacctcag tcaccgtctc ctca           354
```

<210> SEQ ID NO 22
<211> LENGTH: 118
<212> TYPE: PRT
<213> ORGANISM: Artificial Sequence
<220> FEATURE:
<223> OTHER INFORMATION: 32701 VH

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Val Phe Thr Asn Tyr
            20                  25                  30

Gly Met Asn Trp Val Lys Gln Ala Pro Gly Lys Gly Phe Lys Trp Met
        35                  40                  45

Gly Trp Met Asn Thr Asn Thr Gly Glu Pro Thr Ser Leu Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Asp Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser
        115

<210> SEQ ID NO 23
<211> LENGTH: 5
<212> TYPE: PRT
<213> ORGANISM: Artificial Sequence
<220> FEATURE:
<223> OTHER INFORMATION: 32701 VH CDR1

<400> SEQUENCE: 23

Asn Tyr Gly Met Asn
1               5

<210> SEQ ID NO 24
<211> LENGTH: 17
<212> TYPE: PRT
<213> ORGANISM: Artificial Sequence
<220> FEATURE:
<223> OTHER INFORMATION: 32701 VH CDR2

<400> SEQUENCE: 24

Trp Met Asn Thr Asn Thr Gly Glu Pro Thr Ser Leu Glu Asp Phe Lys
1               5                   10                  15

Gly

<210> SEQ ID NO 25
<211> LENGTH: 9
<212> TYPE: PRT
<213> ORGANISM: Artificial Sequence
<220> FEATURE:
<223> OTHER INFORMATION: 32701 VH CDR3

<400> SEQUENCE: 25

Ser Gly Gly Tyr Asp Pro Met Asp Tyr
 1               5

<210> SEQ ID NO 26
<211> LENGTH: 333
<212> TYPE: DNA
<213> ORGANISM: Artificial Sequence
<220> FEATURE:
<223> OTHER INFORMATION: 32701 VL

<400> SEQUENCE: 26
gacattgtgc tgacccaatc tccagcttct ttggctgtgt ctccagggca gagggccacc      60
atatcctgca gagccagtga aagtgttgat aattatggca atactttat gcactggtac      120 cagcagaaac caggacagcc acccaaactc ctcatctatc gtgcatccaa cctagaatct     180
gggatccctg ccaggttcag tggcagtgac tctaggacag acttcaccct caccattaat     240
cctgtggagg ctgatgatgt tgcaacctat tactgtcagc aaagtaaaga ggatcctccc     300
acgttcggtg ctgggactaa gctggagctg aaa                                 333

<210> SEQ ID NO 27
<211> LENGTH: 111
<212> TYPE: PRT
<213> ORGANISM: Artificial Sequence
<220> FEATURE:
<223> OTHER INFORMATION: 32701 VL

<400> SEQUENCE: 27

Asp Ile Val Leu Thr Gln Ser Pro Ala Ser Leu Ala Val Ser Pro Gly
 1               5                  10                  15

Gln Arg Ala Thr Ile Ser Cys Arg Ala Ser Glu Ser Val Asp Asn Tyr
                20                  25                  30

Gly Asn Thr Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Asp Ser Arg Thr Asp Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Asp Pro Pro Thr Phe Gly Ala Gly Thr Lys Leu Glu Leu Lys
                100                 105                 110

<210> SEQ ID NO 28
<211> LENGTH: 15
<212> TYPE: PRT
<213> ORGANISM: Artificial Sequence
<220> FEATURE:
<223> OTHER INFORMATION: 32701 VL CDR1

<400> SEQUENCE: 28

Arg Ala Ser Glu Ser Val Asp Asn Tyr Gly Asn Thr Phe Met His

<210> SEQ ID NO 29
<211> LENGTH: 7
<212> TYPE: PRT
<213> ORGANISM: Artificial Sequence
<220> FEATURE:
<223> OTHER INFORMATION: 32701 VL CDR2

<400> SEQUENCE: 29

Arg Ala Ser Asn Leu Glu Ser
1               5

<210> SEQ ID NO 30
<211> LENGTH: 9
<212> TYPE: PRT
<213> ORGANISM: Artificial Sequence
<220> FEATURE:
<223> OTHER INFORMATION: 32701 VL CDR3

<400> SEQUENCE: 30

Gln Gln Ser Lys Glu Asp Pro Pro Thr
1               5

<210> SEQ ID NO 31
<211> LENGTH: 354
<212> TYPE: DNA
<213> ORGANISM: Artificial Sequence
<220> FEATURE:
<223> OTHER INFORMATION: 32716 VH

<400> SEQUENCE: 31
cagatccagt tggtgcagtc tggacctgag ctgaagaagc ctggagagac agtcaagatc      60
tcctgcaagg cttctgggta tatttcaca aactatggaa tgaactgggt gaagcaggct     120
ccaggaaaga gttttaagtg gatgggctgg ataaacacct acactggaga gtcaacatat     180
agtgctgact caagggacg gtttgccttc tctttggaaa cctctgccag cactgcctat     240
ttgcatatca acgacctcaa aaatgaggac acggctacat atttctgtgc aagatcgggg     300
ggttacgacc ccatggacta ctggggtcaa ggaacctcag tcaccgtctc ctca          354

<210> SEQ ID NO 32
<211> LENGTH: 118
<212> TYPE: PRT
<213> ORGANISM: Artificial Sequence
<220> FEATURE:
<223> OTHER INFORMATION: 32716 VH

<400> SEQUENCE: 32

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr

```
                  100                 105                 110
Ser Val Thr Val Ser Ser
        115

<210> SEQ ID NO 33
<211> LENGTH: 5
<212> TYPE: PRT
<213> ORGANISM: Artificial Sequence
<220> FEATURE:
<223> OTHER INFORMATION: 32716 VH CDR1

<400> SEQUENCE: 33

Asn Tyr Gly Met Asn
 1               5

<210> SEQ ID NO 34
<211> LENGTH: 17
<212> TYPE: PRT
<213> ORGANISM: Artificial Sequence
<220> FEATURE:
<223> OTHER INFORMATION: 32716 VH CDR2

<400> SEQUENCE: 34

Trp Ile Asn Thr Tyr Thr Gly Glu Ser Thr Tyr Ser Ala Asp Phe Lys
 1               5                  10                  15
Gly

<210> SEQ ID NO 35
<211> LENGTH: 9
<212> TYPE: PRT
<213> ORGANISM: Artificial Sequence
<220> FEATURE:
<223> OTHER INFORMATION: 32716 VH CDR3

<400> SEQUENCE: 35

Ser Gly Gly Tyr Asp Pro Met Asp Tyr
 1               5

<210> SEQ ID NO 36
<211> LENGTH: 333
<212> TYPE: DNA
<213> ORGANISM: Artificial Sequence
<220> FEATURE:
<223> OTHER INFORMATION: 32716 VL

<400> SEQUENCE: 36
gacattgtac tgacccaatc tccagcttct ttggctgtgt ctctagggca gagggccacc      60
atatcctgca gagccagtga agtgttgat aattatggca actttttat gcactggtac      120 cagcagaaac aggacagcc acccaaactc ctcatctatc gtgcatccaa cctagaatct      180
gggatccctg ccaggttcag tggcagtggg tctaggacag acttcaccct caccattaat      240
cctgtggagg ctgatgatgt tgcaacctat tactgtcagc aaagtaatga ggatcctccc      300
acgttcggtg ctgggaccaa gctggagctg aaa                                  333

<210> SEQ ID NO 37
<211> LENGTH: 111
<212> TYPE: PRT
<213> ORGANISM: Artificial Sequence
<220> FEATURE:
<223> OTHER INFORMATION: 32716 VL

<400> SEQUENCE: 37

Asp Ile Val Leu Thr Gln Ser Pro Ala Ser Leu Ala Val Ser Leu Gly
```

```
                1               5                  10                 15
            Gln Arg Ala Thr Ile Ser Cys Arg Ala Ser Glu Ser Val Asp Asn Tyr
                            20                  25                  30

Gly Asn Thr Phe Met His Trp Tyr Gln Gln Lys Pro Gly Gln Pro Pro
                        35                  40                  45

Lys Leu Leu Ile Tyr Arg Ala Ser Asn Leu Glu Ser Gly Ile Pro Ala
                    50                  55                  60

Arg Phe Ser Gly Ser Gly Ser Arg Thr Asp Phe Thr Leu Thr Ile Asn
            65                  70                  75                  80

Pro Val Glu Ala Asp Asp Val Ala Thr Tyr Tyr Cys Gln Gln Ser Asn
                                85                  90                  95

Glu Asp Pro Pro Thr Phe Gly Ala Gly Thr Lys Leu Glu Leu Lys
                            100                 105                 110

<210> SEQ ID NO 38
<211> LENGTH: 15
<212> TYPE: PRT
<213> ORGANISM: Artificial Sequence
<220> FEATURE:
<223> OTHER INFORMATION: 32716 VL CDR1

<400> SEQUENCE: 38

Arg Ala Ser Glu Ser Val Asp Asn Tyr Gly Asn Thr Phe Met His
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: 32716 VL CDR2

<400> SEQUENCE: 39

Arg Ala Ser Asn Leu Glu Ser
1               5

<210> SEQ ID NO 40
<211> LENGTH: 9
<212> TYPE: PRT
<213> ORGANISM: Artificial Sequence
<220> FEATURE:
<223> OTHER INFORMATION: 32716 VL CDR3

<400> SEQUENCE: 40

Gln Gln Ser Asn Glu Asp Pro Pro Thr
1               5

<210> SEQ ID NO 41
<211> LENGTH: 115
<212> TYPE: PRT
<213> ORGANISM: Artificial Sequence
<220> FEATURE:
<223> OTHER INFORMATION: VH of the germline sequence (Fig. 5A)

<400> SEQUENCE: 41

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Met Asp Trp Val Lys Gln Arg Pro Gly Gln Gly Leu Glu Trp Ile
            35                  40                  45

Gly Asn Ile Tyr Pro Ser Asp Ser Glu Thr His Tyr Asn Gln Lys Phe
```

```
                50                  55                  60
Lys Asp Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Asn Trp Asp Asp Tyr Trp Gly Gln Gly Thr Thr Leu Thr
                100                 105                 110

Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: VL of the germline sequence (Fig. 5B)

<400> SEQUENCE: 42

Asp Val Gln Ile Thr Gln Ser Pro Ser Tyr Leu Ala Ala Ser Pro Gly
  1               5                  10                  15

Glu Thr Ile Thr Ile Asn Cys Arg Ala Ser Lys Ser Ile Ser Lys Tyr
                 20                  25                  30

Leu Ala Trp Tyr Gln Glu Lys Pro Gly Lys Thr Asn Lys Leu Leu Ile
             35                  40                  45

Tyr Ser Gly Ser Thr Leu Gln Ser Gly Ile Pro Ser Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Tyr
                 85                  90                  95

Thr Phe Gly Gly Gly Thr Lys Leu Glu Ile Lys
                100                 105
```